US008877175B2

(12) United States Patent
Pearlman et al.

(10) Patent No.: US 8,877,175 B2
(45) Date of Patent: *Nov. 4, 2014

(54) LONG LASTING DRUG FORMULATIONS

(71) Applicant: Medgenics Medical Israel Ltd., Misgav (IL)

(72) Inventors: Andrew Pearlman, D.N Misgav (IL); Baruch S. Stern, Haifa (IL)

(73) Assignee: Medgenics Medical Israel Ltd. (IL)

( * ) Notice: Subject to any disclaimer, the term of this patent is extended or adjusted under 35 U.S.C. 154(b) by 65 days.

This patent is subject to a terminal disclaimer.

(21) Appl. No.: 13/776,745

(22) Filed: Feb. 26, 2013

(65) Prior Publication Data

US 2013/0251679 A1 Sep. 26, 2013

Related U.S. Application Data

(63) Continuation of application No. 13/346,761, filed on Jan. 10, 2012, now Pat. No. 8,454,948, which is a continuation-in-part of application No. 13/160,632, filed on Jun. 15, 2011, which is a continuation-in-part of application No. 11/898,481, filed on Sep. 12, 2007.

(60) Provisional application No. 61/355,029, filed on Jun. 15, 2010, provisional application No. 61/414,921, filed on Nov. 18, 2010, provisional application No. 60/844,351, filed on Sep. 14, 2006.

(51) Int. Cl.
| | |
|---|---|
| *A61K 35/12* | (2006.01) |
| *A61K 48/00* | (2006.01) |
| *A61K 47/48* | (2006.01) |
| *C12N 15/86* | (2006.01) |
| *C12N 7/00* | (2006.01) |
| *C07K 14/505* | (2006.01) |
| *A61K 38/18* | (2006.01) |
| *A61K 38/21* | (2006.01) |
| *A61K 31/70* | (2006.01) |
| *C12N 15/88* | (2006.01) |
| *A61K 35/36* | (2006.01) |

(52) U.S. Cl.
CPC ....... *A61K 48/0066* (2013.01); *A61K 47/48776* (2013.01); *C12N 15/86* (2013.01); *C12N 7/00* (2013.01); *A61K 48/0075* (2013.01); *C07K 14/505* (2013.01); *A61K 38/1816* (2013.01); *A61K 38/212* (2013.01); *A61K 48/0091* (2013.01); *A61K 31/70* (2013.01); *C12N 15/88* (2013.01); *C12N 2710/10343* (2013.01); *A61K 35/36* (2013.01)
USPC ........................................................ 424/93.1

(58) Field of Classification Search
CPC .............................. A61K 35/12; A61K 48/00
USPC ........................................................ 424/93.1
See application file for complete search history.

(56) References Cited

U.S. PATENT DOCUMENTS

| | | |
|---|---|---|
| 376,511 A | 1/1888 | Carter |
| 1,516,071 A | 11/1924 | Apolant. |
| 3,076,461 A | 2/1963 | Meek et al. |
| 3,470,782 A | 10/1969 | Acker. |
| 3,613,242 A | 10/1971 | Hill et al. |
| 4,353,888 A | 10/1982 | Sefton |
| 4,391,909 A | 7/1983 | Lim |
| 4,667,016 A | 5/1987 | Lai et al. |
| 4,683,195 A | 7/1987 | Mullis et al. |
| 4,703,008 A | 10/1987 | Lin |
| 4,736,866 A | 4/1988 | Leder et al. |
| 4,773,418 A | 9/1988 | Hettich |
| 4,883,666 A | 11/1989 | Sabel et al. |
| 4,892,538 A | 1/1990 | Aebischer et al. |
| 4,954,437 A | 9/1990 | Beck et al. |
| 5,013,830 A | 5/1991 | Ohtsuka et al. |
| 5,043,711 A | 8/1991 | Harrington |
| 5,106,627 A | 4/1992 | Aebischer et al. |
| 5,149,797 A | 9/1992 | Pederson et al. |
| 5,175,383 A | 12/1992 | Leder et al. |
| 5,175,384 A | 12/1992 | Krimpenfort et al. |
| 5,175,385 A | 12/1992 | Wagner et al. |
| 5,220,007 A | 6/1993 | Pederson et al. |
| 5,221,778 A | 6/1993 | Byrne et al. |
| 5,256,775 A | 10/1993 | Froehler |
| 5,266,480 A | 11/1993 | Naughton et al. |
| 5,288,846 A | 2/1994 | Quertermous et al. |
| 5,298,422 A | 3/1994 | Schwartz et al. |

(Continued)

FOREIGN PATENT DOCUMENTS

| | | |
|---|---|---|
| DE | 29 39 057 | 4/1981 |
| DE | 34 32 897 | 3/1986 |
| EP | 1306426 | 5/2003 |
| EP | 1358857 | 11/2003 |
| JP | 233694/86 | 10/1986 |

(Continued)

OTHER PUBLICATIONS

Garg et al.; "The Hybrid Cytomegalovirus Enhancer/Chicken β-Actin Promoter along with Woodchuck Hepatitis Virus Post-transcriptional Regulatory Element Enchances the Protective Efficacy of DNA Vaccines", The Journal of Immunology, vol. 173, pp. 550-558, 2004.

(Continued)

*Primary Examiner* — Anoop Singh
*Assistant Examiner* — David A Montanari
(74) *Attorney, Agent, or Firm* — McNeil Baur, PLLC

(57) ABSTRACT

The present invention is directed to long-lasting erythropoietin therapeutic formulations and their methods of use wherein the formulation comprises a genetically modified micro-organ that comprises a vector which comprises a nucleic acid sequence operably linked to one or more regulatory sequences, wherein the nucleic acid sequence encodes erythropoietin.

16 Claims, 23 Drawing Sheets

(56) References Cited

U.S. PATENT DOCUMENTS

| | | |
|---|---|---|
| 5,347,075 A | 9/1994 | Sorge |
| 5,360,735 A | 11/1994 | Weinshank et al. |
| 5,366,878 A | 11/1994 | Pederson et al. |
| 5,387,742 A | 2/1995 | Cordell |
| 5,423,330 A | 6/1995 | Lee |
| 5,441,868 A | 8/1995 | Lin |
| 5,464,764 A | 11/1995 | Capecchi et al. |
| 5,477,862 A | 12/1995 | Haaga |
| 5,487,992 A | 1/1996 | Capecchi et al. |
| 5,491,133 A | 2/1996 | Walder et al. |
| 5,547,933 A | 8/1996 | Lin |
| 5,565,350 A | 10/1996 | Kmiec |
| 5,618,698 A | 4/1997 | Lin |
| 5,621,080 A | 4/1997 | Lin |
| 5,622,866 A | 4/1997 | Motamedi et al. |
| 5,623,065 A | 4/1997 | Cook et al. |
| 5,652,256 A | 7/1997 | Knowles |
| 5,652,355 A | 7/1997 | Metelev et al. |
| 5,670,148 A | 9/1997 | Sherwin et al. |
| 5,693,064 A | 12/1997 | Arnold |
| 5,700,922 A | 12/1997 | Cook |
| 5,756,349 A | 5/1998 | Lin |
| 5,817,120 A | 10/1998 | Rassman |
| 5,871,767 A | 2/1999 | Dionne et al. |
| 5,888,720 A | 3/1999 | Mitrani |
| 5,932,459 A | 8/1999 | Sittinger et al. |
| 5,944,673 A | 8/1999 | Gregoire et al. |
| 5,955,422 A | 9/1999 | Lin |
| 6,001,647 A | 12/1999 | Peek et al. |
| 6,027,512 A | 2/2000 | Bridges |
| 6,036,657 A | 3/2000 | Milliman |
| 6,039,760 A | 3/2000 | Eisenberg |
| 6,197,575 B1 | 3/2001 | Griffith et al. |
| 6,274,354 B1 | 8/2001 | Wilson et al. |
| 6,303,136 B1 | 10/2001 | Li et al. |
| 6,372,482 B1 | 4/2002 | Mitarni |
| 6,472,200 B1 | 10/2002 | Mitrani |
| 6,485,721 B1 | 11/2002 | Yoshida et al. |
| 7,067,496 B2 | 6/2006 | Saito et al. |
| 7,468,242 B2 | 12/2008 | Bellomo et al. |
| 7,625,384 B2 | 12/2009 | Eriksson et al. |
| 7,666,134 B2 | 2/2010 | Eriksson et al. |
| 7,708,746 B2 | 5/2010 | Eriksson et al. |
| 8,586,024 B2 | 11/2013 | Pearlman et al. |
| 2002/0001580 A1 | 1/2002 | Hermonat et al. |
| 2002/0068880 A1 | 6/2002 | Burbank et al. |
| 2003/0086914 A1 | 5/2003 | Mitrani |
| 2003/0124565 A1 | 7/2003 | Garfinkel et al. |
| 2003/0152561 A1 | 8/2003 | Mitrani |
| 2003/0152562 A1 | 8/2003 | Mitrani |
| 2003/0157074 A1 | 8/2003 | Mitrani |
| 2004/0157293 A1 | 8/2004 | Evans et al. |
| 2004/0172045 A1 | 9/2004 | Eriksson et al. |
| 2004/0230215 A1 | 11/2004 | Eriksson et al. |
| 2005/0053587 A1 | 3/2005 | Galipeau et al. |
| 2005/0188431 A1 | 8/2005 | Ivarie et al. |
| 2006/0271070 A1 | 11/2006 | Eriksson et al. |
| 2007/0038236 A1 | 2/2007 | Cohen |
| 2008/0090777 A1 | 4/2008 | Pearlman |
| 2010/0042127 A1 | 2/2010 | Eriksson et al. |
| 2010/0145360 A1 | 6/2010 | Eriksson et al. |
| 2011/0033429 A1 | 2/2011 | Notka et al. |

FOREIGN PATENT DOCUMENTS

| | | |
|---|---|---|
| JP | 76399/99 | 3/1999 |
| JP | 2003-176213 | 6/2003 |
| JP | 2005/506084 | 3/2005 |
| JP | 08/196271 | 8/2008 |
| WO | WO 93/14200 | 7/1993 |
| WO | WO 94/06908 | 3/1994 |
| WO | WO 94/23049 | 10/1994 |
| WO | WO 94/28123 | 12/1994 |
| WO | WO 96/15225 | 5/1996 |
| WO | WO 9704720 | 2/1997 |
| WO | WO 97/08295 | 3/1997 |
| WO | WO 9715655 | 5/1997 |
| WO | WO 98/17801 | 4/1998 |
| WO | WO 98/16158 | 5/1998 |
| WO | WO 99/49807 | 7/1999 |
| WO | WO 99/43270 | 9/1999 |
| WO | WO 99/47678 | 9/1999 |
| WO | WO 00/11151 | 3/2000 |
| WO | WO 00/69913 A1 | 11/2000 |
| WO | WO 01/00859 | 1/2001 |
| WO | WO 01/07098 | 2/2001 |
| WO | WO 01/08714 | 2/2001 |
| WO | WO 01/60424 | 8/2001 |
| WO | WO 03/000669 | 1/2003 |
| WO | WO 03/002154 | 1/2003 |
| WO | WO 03/020107 | 3/2003 |
| WO | WO 03/035851 | 5/2003 |
| WO | WO 03/039382 | 5/2003 |
| WO | WO 03/040686 | 5/2003 |
| WO | WO/03049626 | 6/2003 |
| WO | WO 03/053997 | 7/2003 |
| WO | WO 03/060062 | 7/2003 |
| WO | WO 2004/046365 | 6/2004 |
| WO | WO 2004/075764 | 9/2004 |
| WO | WO 2004/099363 | 11/2004 |
| WO | WO 2005/033273 | 4/2005 |
| WO | WO 2006/110843 | 10/2006 |
| WO | WO 2007/117488 | 10/2007 |
| WO | WO 2008/033375 | 3/2008 |
| WO | WO 99/06073 | 2/2009 |

OTHER PUBLICATIONS

Lippin et al.; "Human Erythropoietin Gene Therapy for Patients with Chronic Renal Failure"; Molecular Therapy, vol. 11, Aug. 15, 2005, p. 133.

Supplementary European Search Report for European Application No. 11796340.5, Apr. 24, 2013.

Kim et al. "Lifetime correction of genetic deficiency in mice With a single injection of helper-dependent adenoviral vector" PNAS vol. 98 No. 23, Nov. 6, 2001, pp. 13282-13287.

Darquet et al. "A new DNA vehicle for nonviral gene delivery: supercoiled minicircle" Gene Ther. 4(12):1341-9, Dec. 1997.

Chiou et al. "Gene therapy strategies for the treatment of chronic viral hepatitis" Expert Opin Biol Ther. 1(4):629-39, Jul. 2001.

Chen et al. "Adeno-associated virus mediated interferon-gamma inhibits the progression of hepatic fibrosis in vitro and in vivo" World J Gastroenterol; 11(26):4045-4051, Jul. 14, 2005.

Marvin Caruthers. "Gene Synthesis Machines: DNA Chemistry and Its Uses" Gene synthesis machines. Science 230: 281-285, (1985).

Palmer and Ng. "Improved System for Helper-Dependent Adenoviral Vector Production" Molecular Therapy vol. 8, No. 5, Nov. 2003, pp. 846-852.

Palmer and Ng. "Physical and Infectious Titers of Helper-Dependent Adenoviral Vectors: A Method of Direct Comparison to the Adenovirus Reference Material" Molecular Therapy vol. 10, No. 4, Oct. 2004, pp. 792-798.

Brunetti et al. "Improved Hepatic Transduction, Reduced Systemic Vector Dissemination, and Long-Term Transgene Expression by Delivering Helper-Dependent Adenoviral Vectors into the Surgically Isolated Liver of Nonhuman Primates" Human Gene Therapy 17:391-404 Apr. 2006.

Brunetti et al. "Pseudo-hydrodynamic Delivery of Helper dependent Adenoviral Vectors into Non-human Primates for Liver-directed Gene Therapy" Molecular Therapy vol. 15 No. 4,732-740 Apr. 2007.

Brunetti et al. "Efficient, Long-term Hepatic Gene Transfer Using Clinically Relevant HDAd Doses by Balloon Occlusion Catheter Delivery in Nonhuman Primates" Molecular Therapy vol. 17 No. 2,327-333 Feb. 2009.

Harui et al. "Frequency and Stability of Chromosomal Integration of Adenovirus Vectors" Journal of Virology, p. 6141-6146 vol. 73, No. 7, Jul. 1999.

(56) References Cited

OTHER PUBLICATIONS

Hillgenberg et al. "Chromosomal Integration Pattern of a Helper-Dependent Minimal Adenovirus Vector with a Selectable Marker Inserted into a 27.4-Kilobase Genomic Stuffer" Journal of Virology, p. 9896-9908 vol. 75, No. 20, Oct. 2001.
Stephen et al. "Homologous and heterologous recombination between adenovirus vector DNA and chromosomal DNA" The Journal of Gene Medicine J Gene Med; 10: 1176-1189, (2008).
Stephen et al. "Chromosomal Integration of Adenoviral Vector DNA in Vivo" Journal of Virology, p. 9987-9994 vol. 84, No. 19, Oct. 2010.
Parks et al. "A helper-dependent adenovirus vector system: Removal of helper Virus by Cre-mediated excision of the viral packaging signal" Proc. Natl. Acad. Sci. USA vol. 93, pp. 13565-13570 Applied Biological Sciences, Nov. 1996.
Umana et al. "Efficient FLPe recombinase enables scalable production of helper-dependent adenoviral vectors with negligible helper-virus contamination" Nature Biotechnology vol. 19, Jun. 2001, pp. 582-585.
Suzuki et al. "Development of a recombinant adenovirus vector production system free of replication-competent adenovirus by utilizing a packaging size limit of the viral genome" Virus Research 158, 154-160, (2011).
Bett et al. "Packaging Capacity and Stability of Human Adenovirus Type 5 Vectors" Journal of Virology, Oct. p. 5911-5921 vol. 67, No. 10, (1993).
Park Dkh et al. "[Removal of the 3'- and 5'-untranslated region amplifies expression of the erythropoietin gene in mammalian cells]" Mol Biol (Mosk). 35(3):413-6, May-Jun. 2001.
Mader and White. "A steroid-inducible promoter for the controlled overexpression of cloned genes in eukaryotic cells" Proc. Natl. Acad. Sci. USA vol. 90, pp. 5603-5607, Biochemistry, Jun. 1993.
Spencer et al. Controlling Signal Transduction with Synthetic Ligands. Science, 262, 1019-1024, (1993).
Manome et al. "Coinduction of c-jun gene expression and internucleosomal DNA fragmentation by ionizing radiation" Biochemistry. ; 32(40):10607-13. Oct. 12, 1993.
Ayus et al. "Effects of erythropoietin on left ventricular hypertrophy in adults with severe chronic renal failure and hemoglobin <10 g/dL" Kidney Int. ;68(2):788-95, Aug. 2005.
Andrijauskas et al. "New method of tracing blood hemoglobin concentration to hematocrit ratio for monitoring plasma dilution and osmotic origin shifts in blood" Medicina (Kaunas). 42(3):181-6, (2006).
Toubiana et al. Therapy-resistant anaemia in congenital nephrotic syndrome of the Finnish type—implication of EPO, transferrin and transcobalamin losses. Nephrol Dial Transplant. Apr. 2009; 24(4):1338-40. Epub Jan. 18, 2009.
International Search Report No. PCT/US 11/40439 Date of Mailing Nov. 22, 2011.
International Search Report No. PCT/US 07/19774 Date of Mailing Jun. 20, 2008.
Perry et al. "Interferon-α-2a: A Review of its Use in Chronic Hepatitis C" BioDrugs, vol. 10, No. 1, pp. 65-89(25), Jul. 1998.
Ohi et al. "Administration of recombinant human erythropoietin (rEPO) to patients with diabetic renal failure in the conservative phase", Treatment, vol. 73, No. 6, Medical On-Line, Jun. 1991, pp. 173-179.
Hirakata, H et al. "Pathologic condition of and treatment policy for end-stage renalfailure", Clinical Study, vol. 76 No. 8, Medical On-Line. Aug. 1999, pp. 105-112.
Hino, K. et al. "Result with Recombinant Interferon alpha-2b in International Trials for Viral Hepatitis": Journal of Kawasaki Medical School, vol. 18 No. 3 ,(1992), 157-161.
Nakahara N. et al. "Interferon gene therapy—basic to clinical researches", General Clinical Study, vol. 52 No. 9, Medical On-Line. Sep. 2003, pp. 2514-2521.
Rubanyi. "The Future of Human Gene Therapy" Molecular Aspects of Medicine, 22:113-142, (2001).
Orive et al. "Cell encapsulation: Promise and progress" Nature Medicine, 9(1):104-107, (2003).
Brill-Almon E. et al: "Ex vivo transduction of human dermal tissue structures for autologous implantation production and delivery of therapeutic proteins," Molecular Therapy, Academic Press, CA, USA, vol. 12, No. 2, pp. 274-282, (2005).
Hasson E. et al. "Solid tissues can be manipulated ex vivo and used as vehicles for gene therapy" Journal of Gene Medicine, vol. 7(7), pp. 926-935 , (2005).
Uitto et al. "Skin elastic fibres: regulation of human elastin promoter activity in transgenic mice". Ciba Foundation Symposium, vol. 192, p. 237-253, (1995).
Wang et al. "Transgenic studies with a keratin promoter-driven growth hormone transgene: prospects for gene therapy" Proc Natl Acad Sci U S A. 4(1):219-26. 1. Jan. 7, 1997.
Supplementary European Search Report. Application No. 04760621.5 Date of Mailing Apr. 27, 2009.
International Search Report. Application No. PCT/US04/13194 Date of mailing Mar. 18, 2005.
Jaakkola et al. "Transcriptional targeting of adenoviral gene delivery into migrating wound keratinocytes using fire, a growth factor—inducible regulatory element" Gene Therapy 7:1640-1647, (2000).
Palmer et al. "Genetically modified skin fibroblasts persist long after transplantation but gradually inactivate introduced genes" Proc. Nati. Acad. Sci. USA vol. 88, pp. 1330-1334, Cell Biology, Feb. 1991.
Ng et al. "Requirement of an AP—1 site in the Calcium Response Region of the Involucrin Promoter" JBC 275(31): 24080-24088, (2000).
Suzuki et al. "Identification of the hepatocyte mitogen in bovine spleen as heparin-binding growth factors" Biochemical and Biophysical Research Communications vol. 186, Issue 3, pp. 1192-1200, Aug. 14, 1992.
Sato H et al. "Repression of P53-Dependent Sequence-Specific Transactivation by MEF2C" Biochemical and Biophysical Research Communications vol. 214, Issue 2, pp. 468-474, Sep. 14, 1995.
Auerbach et al. "Angiogenesis Induction by Tumors, Embryonic Tissues, and Lymphocyte" Cancer Res; 36:3435-3440, (1976).
Swanson et al. "Characterization of myocyte enhancer factor 2 (MEF2) expression in B and T cells: MEF2C is a B cell-restricted transcription factor in lymphocytes" Molecular Immunology vol. 35, Issue 8, pp. 445-458, , May 1, 1998.
Aoki Y et al. "Angiogenesis and hematopoiesis induced by Kaposi's sarcoma-associated herpesvirus-encoded interleukin-6" Blood. 93:4034-4043, (1999).
Shifren et al. "In the human fetus, vascular endothelial growth factor is expressed in epithelial cells and myocytes, but not vascular endothelium: implications for mode of action" The Journal of Clinical Endocrinology & MetabolismJul. 1, vol. 79 No. 1 316-322, (1994).
Upreti et al. "Preparation of representative homogenates of biological tissues: Effect of salt on protein extraction" Analytical Biochemistry vol. 198, Issue 2, pp. 298-301, Nov. 1, 1991.
Eming et al. "Genetically Modified Human Keratinocytes Overexpressing PDGF-A Enhance the Performance of a Composite Skin Graft" Human Gene Therapy. 9(4): 529-539, Mar. 1998.
Gunther et al. Specific targets in tumor tissue for the delivery of therapeutic genes. Curr Med Chem Anti-cancer Agents 5: 157-171, (2005).
Azimzadeh et al. "Xenograft rejection: molecular mechanisms and therapeutic prospects" Hematology and Cell Therapy . vol. 38, No. 4 ,331-343, (1996).
Gould and Auchincloss. "Direct and indirect recognition: the role of MHC antigens in graft rejection" Immunol Today. 20(2):77-82. Feb. 1999.
Printout from www.hemophilia.org/NhFWeb/MainPgs/MainNHF. aspxmenuid+180&contentid=45, pp. 1-2. printed, Apr. 17, 2012.
Narang et al.; "Biological and Biomaterial Approaches for Improved Islet Transplantation", 2006, Pharmacological Reviews, vol. 58(2), pp. 194-243.
Lin et al.; "Coagulation Dysregulation as a Barrier to Xenotransplantation in the Primate", Published in final edited form as: Transpl Immunol. Jun. 2009 ; 21(2): pp. 75-80.
Fishbane et al.; "Hemoglobin Cycling in Hemodialysis Patients Treated with Recombinant Human Erythropoietin", 2005, Kidney Int., vol. 68, pp. 1337-1343.

(56) References Cited

OTHER PUBLICATIONS

Chavers et al.; "Prevalence of anemia in erythropoietin-treated pediatric as compared to adult chronic dialysis patients", Kidney International, vol. 65 (2004), pp. 266-273.

Eliopoulos et al.; "A neovascularized organoid derived from retrovirally engineered bone marrow stroma leads to prolonged in vivo systemic delivery of erythropoietin in nonmyeloablated, immunocompetent mice", 2003, Gene Therapy, vol. 10, pp. 478-489.

Trivedi; "Erythropoietin Therapy in Pre-Dialysis Patients with Chronic Renal Failure: Lack of Need for Parenteral Iron", Am J Nephrol 2003;23: pp. 78-85.

Ekser; "Clinical Xenotransplantation: the medical revolution?", Oct. 21, 2011, The Lancet, pp. 1-12.

Lippin et al. "erythropoietin gene therapy for patients with chronic renal failure" Blood. 106(7):2280-6, Oct. 1, 2005.

Mitrani et al. "Biopump: Autologous skin-derived micro-organ genetically engineered to provide sustained continuous secretion of therapeutic proteins" Dermatol Ther.; 24 (5):489-97, Sep.-Oct. 2011.

International Search Report Application No. PCT/IL12/50488 Date of Mailing Apr. 29, 2013.

Elder et al. "Successful Culture and Selection of Cytokine Gene-Modified Human Dermal Fibroblasts for the Biologic Therapy of Patients with Cancer" Human Gene Therapy. 7(4): 479-487, Mar. 1996.

Kiwaki K. et al. "Theory of Gene Therapy—Gene therapy of Ornithine transcarbamylase (OTC) deficiency", Igaku No Ayumi, vol. 175, No. 9, pp. 655-659, Dec. 2, 1995.

Saito I. "Adenovirus Vector", Virus, vol. 44, No. 1, pp. 100-104, Jun. 1994.

Kim, C.H. et al. "Codon optimization for high-level expression of human erythropoietin(EPO) in mammalian cells" Gene, vol. 199, No. 1-2, pp. 293-301, Oct. 15, 1997.

Ohi K. et al. "Administration of recombinant human erythropoietin (rEPO) to patients with diabetic renal failure in the conservative phase", Treatment, vol. 73, No. 6, Medical On-Line, Jun. 1991.

Hirakata, H. "Pathologic condition of and treatment policy for end-stage renal failure", Clinical Study, vol. 76 No. 8, Medical On-Line, Aug. 1999.

Hino K. et al. "Result with Recombinant Interferon alpha-2b in International Trials for Viral Hepatitis": Journal of Kawasaki Medical School, vol. 18 No. 3, (1992).

Nakahara, N. "Interferon gene therapy—basic to clinical researches", General Clinical Study, vol. 52 No. 9, Medical On-Line, Sep. 2003.

Trainer et al. "Gene delivery to the epidermis" Human Molecular Genetics, vol. 6, No. 10 Review 1761-1767, (1997).

Mitani K. "New Gene Therapy—Adenovirus vector for the next generation" Igaku No Ayumi, vol. 203, No. 5, pp. 379-383. Nov. 2, 2002.

A.

| | EPO Naive N=6 | EPO dependent N=10 | Total N=16 |
|---|---|---|---|
| Age [min-max~] | 65 (min 48-max 82) | 65 (min 21-max 77) | 65 (min 21-max 82) |
| M/F [ratio] | 3/3 | 5/5 | 8/8 |
| Mean MDRD GFR [mL/min/1.73m²±SD] | 25±8 | 24±13 | 24±12 |
| Basal Hb/projected Hb [gm/dl] | 10.2±0.6 | 9.4±1.0 | 9.7±0.9 |
| Hct [%] | 32.3±1.8 | 32.8±1.9 | 32.6±1.9 |
| Basal absolute reticulocytes [10⁹/l] | 44±20 | 47±25 | 46±23 |
| Basal EPO levels [mU/ml] | 13±6 | 13±9 | 13±8 |
| Basal TSAT [%] | 22±8 | 26±6 | 24±7 |
| Basal Ferritin [ng/ml] | 208±93 | 208±85 | 208±88 |

SEQUENCE LISTING

```
<160> NUMBER OF SEQ ID NOS: 15

<210> SEQ ID NO 1
<211> LENGTH: 582
<212> TYPE: DNA
<213> ORGANISM: Artificial Sequence
<220> FEATURE:
<223> OTHER INFORMATION: optimized variation of human EPO

<400> SEQUENCE: 1
atgggcgtgc acgagtgccc cgcctggctg tggctgctgc tgtccctgct gtctctgccc      60
ctgggcctgc ctgtgctggg agcccctccc cggctgatct gcgacagccg ggtgctggaa     120
agatacctgc tggaagccaa agaggccgag aacatcacca ccgctgcgc cgagcactgc     180 agcctgaacg agaatatcac cgtgcccgac accaaggtga acttctacgc ctggaagcgg     240
atggaagtgg gccagcaggc cgtggaagtg tggcagggcc tggccctgct gtccgaggcc     300
gtgctgagag ggcaggcct gctggtgaac agcagccagc cctgggagcc tctgcagctg     360
cacgtggaca aggccgtgag cggcctgcgg agcctgacca ccctgctgag ggccctgggc     420
gcccagaaag aggccatcag cccccctgat gccgcctctg ccgcccctct gcggaccatc     480
accgccgaca ccttccggaa gctgttccgg gtgtacagca cttcctgcg gggcaagctg     540 aagctgtaca ccggcgaggc ctgccggacc ggcgatcgct ga                        582

<210> SEQ ID NO 2
<211> LENGTH: 645
<212> TYPE: DNA
<213> ORGANISM: Artificial Sequence
<220> FEATURE:
<223> OTHER INFORMATION: optimized variation of human IFN alpha 2b

<400> SEQUENCE: 2
ggcgcgccaa gcttgcatgc ctgcaggtcg actctagact gccatggccc tgaccttcgc      60
cctgctggtg gccctgctgg tgctgtcctg caagagcagc tgcagcgtgg gctgcgacct     120
gccccagacc cacagcctgg gcagccggcg gaccctgatg ctgctggccc agatgcggcg     180
gatcagcctg ttcagctgcc tgaaggaccg gcacgacttc ggcttccccc aggaagagtt     240
cggcaaccag ttccagaagg ccgagaccat ccccgtgctg cacgagatga tccagcagat     300
cttcaacctg ttcagcacca aggacagcag cgccgcctgg gacgagaccc tgctggacaa     360
gttctacacc gagctgtacc agcagctgaa cgacctggaa gctgcgtga tccagggcgt     420 gggcgtgacc gagaccccc tgatgaaaga ggacagcatc ctgccgtgc ggaagtactt     480 ccagcggatc accctgtacc tgaaagagaa gaagtacagc ccctgcgcct gggaagtggt     540
```

-continued

```
gcgggccgag atcatgcgga gcttcagcct gagcaccaac ctgcaggaaa gcctgcggag    600
caaagagtga ggatccccgg gtaccgagct cgaattctta attaa                    645
```

<210> SEQ ID NO 3
<211> LENGTH: 4684
<212> TYPE: DNA
<213> ORGANISM: Artificial Sequence
<220> FEATURE:
<223> OTHER INFORMATION: Sequences from adenovirus, CMV, and variation of human EPO

<400> SEQUENCE: 3

```
catcatcaat aatataccTT attttggatt gaagccaata tgataatgag ggggtggagt    60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggaggcgcgc cctcgagcta gctgttgaca ttgattattg actagttatt    600
aatagtaatc aattacgggg tcattagttc atagcccata tatggagttc cgcgttacat    660
aacttacggt aaatggcccg cctggctgac cgcccaacga ccccccgccca ttgacgtcaa    720 taatgacgta tgttcccata gtaacgccaa tagggacttt ccattgacgt caatgggtgg    780
agtatttacg gtaaactgcc cacttggcag tacatcaagt gtatcatatg ccaagtacgc    840
cccctattga cgtcaatgac ggtaaatggc ccgcctggca ttatgcccag tacatgacct    900
tatgggactt tcctacttgg cagtacatct acgtattagt catcgctatt accatggtga    960
tgcggttttg gcagtacatc aatgggcgtg gatagcggtt tgactcacgg ggatttccaa    1020
gtctccaccc cattgacgtc aatgggagtt tgttttggca ccaaaatcaa cgggactttc    1080
caaaatgtcg taacaactcc gccccattga cgcaaatggg cggtaggcgt gtacggtggg    1140
aggtctatat aagcagagct cgtttagtga accgtaagct tgcatgcctg caggtcgact    1200
ctagactgcc atgggcgtgc acgagtgccc cgcctggctg tggctgctgc tgtccctgct    1260
gtctctgccc ctgggcctgc ctgtgctggg agcccctccc cggctgatct gcgacagccg    1320
ggtgctggaa agatacctgc tggaagccaa agaggccgag aacatcacca ccggctgcgc    1380
cgagcactgc agcctgaacg agaatatcac cgtgcccgac accaaggtga acttctacgc    1440
ctggaagcgg atggaagtgg gccagcaggc cgtggaagtg tggcagggcc tggccctgct    1500
gtccgaggcc gtgctgagag gcaggccct gctggtgaac agcagccagc cctgggagcc    1560
tctgcagctg cacgtggaca aggccgtgag cggcctgcgg agcctgacca ccctgctgag    1620
ggccctgggc gcccagaaag aggccatcag ccccccctgat gccgcctctg ccgcccctct    1680
gcggaccatc accgccgaca ccttccggaa gctgttccgg gtgtacagca acttcctgcg    1740
gggcaagctg aagctgtaca ccggcgaggc ctgccggacc ggcgatcgct gaggatcccc    1800
gggtaccgag ctcgaattct tgtagaggt tttacttgct ttaaaaaacc tcccacacct    1860 cccccctgaac ctgaaacata aaatgaatgc aattgttgtt gttaacttgt ttattgcagc    1920
```

```
ttataatggt tacaaataaa gcaatagcat cacaaatttc acaaataaag catttttttc    1980
actgcattct agttgtggtt tgtccaaact catcaatgta tcgatatcgg cgcgccgggc    2040
ccctacgtca cccgccccgt tcccacgccc cgcgccacgt cacaaactcc accccctcat    2100
tatcatattg gcttcaatcc aaaataaggt atattattga tgatggccgc agcggcccct    2160
ggcgtaatag cgaagaggcc cgcaccgatc gcccttccca acagttgcgc agcctgaatg    2220
gcgaatggga cgcgccctgt agcggcgcat taagcgcggc gggtgtggtg gttacgcgca    2280
gcgtgaccgc tacacttgcc agcgccctag cgcccgctcc tttcgctttc ttcccttcct    2340
ttctcgccac gttcgccggc tttccccgtc aagctctaaa tcgggggctc cctttagggt    2400
tccgatttag tgctttacgg cacctcgacc ccaaaaaact tgattagggt gatggttcac    2460
gtagtgggcc atcgccctga tagacggttt ttcgcccttt gacgttggag tccacgttct    2520
ttaatagtgg actcttgttc caaactggaa caacactcaa ccctatctcg gtctattctt    2580
ttgatttata agggattttg ccgatttcgg cctattggtt aaaaaatgag ctgatttaac    2640
aaaaatttaa cgcgaatttt aacaaaatat taacgcttac aatttaggtg cacttttcg     2700
gggaaatgtg cgcggaaccc ctatttgttt atttttctaa atacattcaa atatgtatcc    2760
gctcatgaga caataaccct gataaatgct tcaataatat tgaaaagga agagtatgag     2820
tattcaacat ttccgtgtcg cccttattcc cttttttgcg gcattttgcc ttcctgtttt    2880
tgctcaccca gaaacgctgg tgaaagtaaa agatgctgaa gatcagttgg gtgcacgagt    2940
gggttacatc gaactggatc tcaacagcgg taagatcctt gagagttttc gccccgaaga    3000
acgttttcca atgatgagca cttttaaagt tctgctatgt ggcgcggtat tatcccgtat    3060
tgacgccggg caagagcaac tcggtcgccg catacactat tctcagaatg acttggttga    3120
gtactcacca gtcacagaaa agcatcttac ggatggcatg acagtaagag aattatgcag    3180
tgctgccata accatgagtg ataacactgc ggccaactta cttctgacaa cgatcggagg    3240
accgaaggag ctaaccgctt ttttgcacaa catgggggat catgtaactc gccttgatcg    3300
ttgggaaccg gagctgaatg aagccatacc aaacgacgag cgtgacacca cgatgcctgt    3360
agcaatggca acaacgttgc gcaaactatt aactggcgaa ctacttactc tagcttcccg    3420
gcaacaatta atagactgga tggaggcgga taaagttgca ggaccacttc tgcgctcggc    3480
ccttccggct ggctggttta ttgctgataa atctggagcc ggtgagcgtg gtctcgcgg     3540
tatcattgca gcactggggc cagatggtaa gccctcccgt atcgtagtta tctacacgac    3600
ggggagtcag gcaactatgg atgaacgaaa tagacagatc gctgagatag gtgcctcact    3660
gattaagcat tggtaactgt cagaccaagt ttactcatat atactttaga ttgatttaaa    3720
acttcatttt taatttaaaa ggatctaggt gaagatcctt tttgataatc tcatgaccaa    3780
aatcccttaa cgtgagtttt cgttccactg agcgtcagac cccgtagaaa agatcaaagg    3840
atcttcttga tccttttttt tctgcgcgt aatctgctgc ttgcaaacaa aaaaaccacc     3900
gctaccagcg gtggtttgtt tgccggatca agagctacca actcttttc cgaaggtaac     3960
tggcttcagc agagcgcaga taccaaatac tgtccttcta gtgtagccgt agttaggcca    4020
ccacttcaag aactctgtag caccgcctac atacctcgct ctgctaatcc tgttaccagt    4080
ggctgctgcc agtggcgata gtcgtgtct taccggggttg gactcaagac gatagttacc    4140
ggataaggcg cagcggtcgg gctgaacggg gggttcgtgc acacagccca gcttggagcg    4200
aacgacctac accgaactga gatacctaca gcgtgagcta tgagaaagcg ccacgcttcc    4260
cgaagggaga aaggcggaca ggtatccggt aagcggcagg gtcggaacag gagagcgcac    4320
```

```
gagggagctt ccaggggga  acgcctggta tctttatagt cctgtcgggt ttcgccacct    4380
ctgacttgag cgtcgatttt tgtgatgctc gtcagggggg cggagcctat ggaaaaacgc    4440
cagcaacgcg gccttttta  ggttcctggc cttttgctgg ccttttgctc acatgttctt    4500
tcctgcgtta tcccctgatt ctgtggataa ccgtattacc gcctttgagt gagctgatac    4560
cgctcgccgc agccgaacga ccgagcgcag cgagtcagtg agcgaggaag cggaagagcg    4620
cccaatacgc aaaccgcctc tccccgcgcg ttggccgatt cattaatgca ggggccgctg    4680
cggc                                                                4684

<210> SEQ ID NO 4
<211> LENGTH: 5261
<212> TYPE: DNA
<213> ORGANISM: Artificial Sequence
<220> FEATURE:
<223> OTHER INFORMATION: Sequences from adenovirus, CAG, and variation
      of human EPO

<400> SEQUENCE: 4
catcatcaat aatataccttt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttttg    180 gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt tgttactca tagcgcgtaa tatttgtcta gggccgcggg      360
gactttgacc gtttacgtgg agactcgccc aggtgttttt ctcaggtgtt ttccgcgttc     420
cgggtcaaag ttggcgtttt attattatag tcagctgacg tgtagtgtat ttatacccgg     480
tgagttcctc aagaggccac tcttgagtgc cagcgagtag agttttctcc tccgagccgc     540
tccgacaccg ggaggcgcgc cctcgagcta gcccctagtt attaatagta atcaattacg     600
gggtcattag ttcatagccc atatatggag ttccgcgtta caaacttac ggtaaatggc      660 ccgcctggct gaccgcccaa cgacccccgc ccattgacgt caataatgac gtatgttccc     720
atagtaacgc caatagggac tttccattga cgtcaatggg tggagtattt acggtaaact     780
gcccacttgg cagtacatca agtgtatcat atgccaagta cgccccctat tgacgtcaat     840
gacggtaaat ggcccgcctg gcattatgcc cagtacatga ccttatggga ctttcctact     900
tggcagtaca tctacgtatt agtcatcgct attaccatgg tcgaggtgag ccccacgttc     960
tgcttcactc tccccatctc cccccctcc ccaccccccaa ttttgtattt atttattttt    1020
taattatttt tgtgcagcgat gggggcgggg gggggggggg ggcgcgcgcc aggcggggcg    1080
ggcgggggcg aggggcgggg cggggcgagg cggagaggtg cggcggcagc caatcagagc    1140
ggcgcgctcc gaaagtttcc ttttatggcg aggcggcggc ggcggcggcc ctataaaaag    1200
cgaagcgcgc ggcgggcggg agtcgctgcg cgctgccttc gccccgtgcc ccgctccgcc    1260
gccgcctcgc gccgcccgcc ccggctctga ctgaccgcgt tactcccaca ggtgagcggg    1320
cgggacggcc cttctcctcc gggctgtaat tagcgcttgg tttaatgacg gcttgtttct    1380
tttctgtggc tgcgtgaaag ccttgagggg ctccgggagc gccggcagga aggaaatggg    1440
cggggagggc cttcgtgcgt cgccgcgccg ccgtccccct ctccctctcc agcctcgggg    1500
ctgtccgcgg ggggacggct gccttcgggg gggacggggc agggcggggt tcggcttctg    1560
gcgtgtgacc ggcggctcta gagcctctgc taaccatgtt catgccttct tctttttcct    1620
```

```
acagctcctg ggcaacgtgc tggttattgt gctgtctcat cattttggca aagaattgat    1680
taattcgagc gaacgcgtcg agtcgctcgg tacgatttaa attgaattgg gctcgagatc    1740
tgcgatctaa gtaagcttgc atgcctgcag gtcgactcta gactgccatg ggcgtgcacg    1800
agtgccccgc ctggctgtgg ctgctgctgt ccctgctgtc tctgcccctg ggcctgcctg    1860
tgctgggagc ccctccccgg ctgatctgcg acagccgggt gctggaaaga tacctgctgg    1920
aagccaaaga ggccgagaac atcaccaccg gctgcgccga gcactgcagc ctgaacgaga    1980
atatcaccgt gcccgacacc aaggtgaact tctacgcctg gaagcggatg gaagtgggcc    2040
agcaggccgt ggaagtgtgg cagggcctgg ccctgctgtc cgaggccgtg ctgagagggc    2100
aggccctgct ggtgaacagc agccagccct gggagcctct gcagctgcac gtggacaagg    2160
ccgtgagcgg cctgcggagc ctgaccaccc tgctgagggc cctgggcgcc cagaaagagg    2220
ccatcagccc ccctgatgcc gcctctgccg cccctctgcg gaccatcacc gccgacacct    2280
tccggaagct gttccgggtg tacagcaact tcctgcgggg caagctgaag ctgtacaccg    2340
gcgaggcctg ccggaccggc gatcgctgag gatccccggg taccgagctc gaattctttg    2400
tagaggtttt acttgcttta aaaaacctcc cacacctccc cctgaacctg aaacataaaa    2460
tgaatgcaat tgttgttgtt aacttgttta ttgcagctta taatggttac aaataaagca    2520
atagcatcac aaatttcaca aataaagcat ttttttcact gcattctagt tgtggtttgt    2580
ccaaactcat caatgtatcg atatcggcgc gccgggcccc tacgtcaccc gccccgttcc    2640
cacgccccgc gccacgtcac aaactccacc ccctcattat catattggct tcaatccaaa    2700
ataaggtata ttattgatga tggccgcagc ggccctggc gtaatagcga agaggcccgc    2760
accgatcgcc cttcccaaca gttgcgcagc ctgaatggcg aatgggacgc gccctgtagc    2820
ggcgcattaa gcgcggcggg tgtggtggtt acgcgcagcg tgaccgctac acttgccagc    2880
gccctagcgc ccgctccttt cgctttcttc ccttcctttc tcgccacgtt cgccggcttt    2940
ccccgtcaag ctctaaatcg ggggctccct ttagggttcc gatttagtgc tttacggcac    3000
ctcgacccca aaaaacttga ttagggtgat ggttcacgta gtgggccatc gccctgatag    3060
acggtttttc gccctttgac gttggagtcc acgttcttta atagtggact cttgttccaa    3120
actggaacaa cactcaaccc tatctcggtc tattcttttg atttataagg gattttgccg    3180
atttcggcct attggttaaa aaatgagctg atttaacaaa aatttaacgc gaattttaac    3240
aaaatattaa cgcttacaat ttaggtggca cttttcgggg aaatgtgcgc ggaaccccta    3300
tttgtttatt tttctaaata cattcaaata tgtatccgct catgagacaa taaccctgat    3360
aaatgcttca ataatattga aaaaggaaga gtatgagtat tcaacatttc cgtgtcgccc    3420
ttattccctt ttttgcggca ttttgccttc ctgtttttgc tcacccagaa acgctggtga    3480
aagtaaaaga tgctgaagat cagttgggtg cacgagtggg ttacatcgaa ctggatctca    3540
acagcggtaa gatccttgag agttttcgcc ccgaagaacg ttttccaatg atgagcactt    3600
ttaaagttct gctatgtggc gcggtattat cccgtattga cgccgggcaa gagcaactcg    3660
gtcgccgcat acactattct cagaatgact tggttgagta ctcaccagtc acagaaaagc    3720
atcttacgga tggcatgaca gtaagagaat tatgcagtgc tgccataacc atgagtgata    3780
acactgcggc caacttactt ctgacaacga tcggaggacc gaaggagcta accgcttttt    3840
tgcacaacat gggggatcat gtaactcgcc ttgatcgttg ggaaccggag ctgaatgaag    3900
ccataccaaa cgacgagcgt gacaccacga tgcctgtagc aatggcaaca acgttgcgca    3960
aactattaac tggcgaacta cttactctag cttcccggca acaattaata gactggatgg    4020
```

| | |
|---|---|
| aggcggataa agttgcagga ccacttctgc gctcggccct tccggctggc tggtttattg | 4080 |
| ctgataaatc tggagccggt gagcgtgggt ctcgcggtat cattgcagca ctggggccag | 4140 |
| atggtaagcc ctcccgtatc gtagttatct acacgacggg gagtcaggca actatggatg | 4200 |
| aacgaaatag acagatcgct gagataggtg cctcactgat taagcattgg taactgtcag | 4260 |
| accaagttta ctcatatata ctttagattg atttaaaact tcattttaa tttaaaagga | 4320 |
| tctaggtgaa gatcctttt gataatctca tgaccaaaat cccttaacgt gagttttcgt | 4380 |
| tccactgagc gtcagacccc gtagaaaaga tcaaggatc ttcttgagat ccttttttc | 4440 |
| tgcgcgtaat ctgctgcttg caaacaaaaa aaccaccgct accagcggtg tttgtttgc | 4500 |
| cggatcaaga gctaccaact ctttttccga aggtaactgg cttcagcaga gcgcagatac | 4560 |
| caaatactgt ccttctagtg tagccgtagt taggccacca cttcaagaac tctgtagcac | 4620 |
| cgcctacata cctcgctctg ctaatcctgt taccagtggc tgctgccagt ggcgataagt | 4680 |
| cgtgtcttac cgggttggac tcaagacgat agttaccgga taaggcgcag cggtcgggct | 4740 |
| gaacggggg ttcgtgcaca cagcccagct tggagcgaac gacctacacc gaactgagat | 4800 |
| acctacagcg tgagctatga gaaagcgcca cgcttcccga agggagaaag gcggacaggt | 4860 |
| atccggtaag cggcagggtc ggaacaggag agcgcacgag ggagcttcca gggggaaacg | 4920 |
| cctggtatct ttatagtcct gtcgggtttc gccacctctg acttgagcgt cgatttttgt | 4980 |
| gatgctcgtc aggggggcgg agcctatgga aaaacgccag caacgcggcc ttttacggt | 5040 |
| tcctggcctt ttgctggcct tttgctcaca tgttctttcc tgcgttatcc cctgattctg | 5100 |
| tggataaccg tattaccgcc tttgagtgag ctgataccgc tcgccgcagc cgaacgaccg | 5160 |
| agcgcagcga gtcagtgagc gaggaagcgg aagagcgccc aatacgcaaa ccgcctctcc | 5220 |
| ccgcgcgttg gccgattcat taatgcaggg gccgctgcgg c | 5261 |

<210> SEQ ID NO 5
<211> LENGTH: 4669
<212> TYPE: DNA
<213> ORGANISM: Artificial Sequence
<220> FEATURE:
<223> OTHER INFORMATION: Sequences from adenovirus, CMV, and variation
      of human IFN alpha 2b

<400> SEQUENCE: 5

| | |
|---|---|
| catcatcaat aatataccttt attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggccgcggg | 360 |
| gactttgacc gtttacgtgg agactcgccc aggtgttttt ctcaggtgtt ttccgcgttc | 420 |
| cgggtcaaag ttggcgtttt attattatag tcagctgacg tgtagtgtat ttatacccgg | 480 |
| tgagttcctc aagaggccac tcttgagtgc cagcgagtag agttttctcc tccgagccgc | 540 |
| tccgacaccg ggaggcgcgc cctcgagcta gctgttgaca ttgattattg actagttatt | 600 |
| aatagtaatc aattacgggg tcattagttc atagcccata tatggagttc gcgttacat | 660 |
| aacttacggt aaatggcccg cctggctgac cgcccaacga cccccgccca ttgacgtcaa | 720 |
| taatgacgta tgttcccata gtaacgccaa tagggacttt ccattgacgt caatgggtgg | 780 |

```
agtatttacg gtaaactgcc cacttggcag tacatcaagt gtatcatatg ccaagtacgc    840
cccctattga cgtcaatgac ggtaaatggc ccgcctggca ttatgcccag tacatgacct    900
tatgggactt tcctacttgg cagtacatct acgtattagt catcgctatt accatggtga    960
tgcggttttg gcagtacatc aatgggcgtg gatagcggtt tgactcacgg ggatttccaa   1020
gtctccaccc cattgacgtc aatgggagtt tgttttggca ccaaaatcaa cgggactttc   1080
caaaatgtcg taacaactcc gccccattga cgcaaatggg cggtaggcgt gtacggtggg   1140
aggtctatat aagcagagct cgtttagtga accgtaagct tgcatgcctg caggtcgact   1200
ctagactgcc atggcctga ccttcgccct gctggtggcc ctgctggtgc tgtcctgcaa    1260
gagcagctgc agcgtgggct gcgacctgcc ccagacccac agcctgggca gccggcggac   1320
cctgatgctg ctggcccaga tgcggcggat cagcctgttc agctgcctga aggaccggca   1380
cgacttcggc ttcccccagg aagagttcgg caaccagttc cagaaggccg agaccatccc   1440
cgtgctgcac gagatgatcc agcagatctt caacctgttc agcaccaagg acagcagcgc   1500
cgcctgggac gagaccctgc tggacaagtt ctacaccgag ctgtaccagc agctgaacga   1560
cctggaagcc tgcgtgatcc agggcgtggg cgtgaccgag acccccctga tgaaagagga   1620
cagcatcctg gccgtgcgga gtacttcca gcggatcacc ctgtacctga agagaagaa    1680
gtacagcccc tgcgcctggg aagtggtgcg ggccgagatc atgcggagct tcagcctgag   1740
caccaacctg caggaaagcc tgcggagcaa agagtgagga tccccgggta ccgagctcga   1800
attctttgta gaggttttac ttgctttaaa aaacctccca cacctccccc tgaacctgaa   1860
acataaaatg aatgcaattg ttgttgttaa cttgtttatt gcagcttata atggttacaa   1920
ataaagcaat agcatcacaa atttcacaaa taaagcattt ttttcactgc attctagttg   1980
tggtttgtcc aaactcatca atgtatcgat atcggcgcgc cgggcccta cgtcacccgc    2040
cccgttccca cgccccgcgc cacgtcacaa actccacccc ctcattatca tattggcttc   2100
aatccaaaat aaggtatatt attgatgatg ccgcagcgg cccctggcgt aatagcgaag    2160
aggcccgcac cgatcgccct tcccaacagt tgcgcagcct gaatggcgaa tgggacgcgc   2220
cctgtagcgg cgcattaagc gcggcgggtg tggtggttac gcgcagcgtg accgctacac   2280
ttgccagcgc cctagcgccc gctccttttcg ctttcttccc ttcctttctc gccacgttcg  2340
ccggcttttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa atattaacg cttacaattt aggtggcact tttcggggaa atgtgcgcgg    2700
aaccectatt tgtttatttt tctaaataca ttcaaatatg tatccgctca tgagacaata   2760
accctgataa atgcttcaat aatattgaaa aaggaagagt atgagtattc aacatttccg   2820
tgtcgccctt attccctttt ttgcggcatt ttgccttcct gttttgctc acccagaaac    2880
gctggtgaaa gtaaaagatg ctgaagatca gttgggtgca cgagtgggtt acatcgaact   2940
ggatctcaac agcggtaaga tccttgagag ttttcgcccc gaagaacgtt ttccaatgat   3000
gagcactttt aaagttctgc tatgtggcgc ggtattatcc cgtattgacg ccgggcaaga   3060
gcaactcggt cgccgcatac actattctca gaatgacttg gttgagtact caccagtcac   3120
agaaaagcat cttacggatg gcatgacagt aagagaatta tgcagtgctg ccataaccat   3180
```

```
gagtgataac actgcggcca acttacttct gacaacgatc ggaggaccga aggagctaac    3240
cgcttttttg cacaacatgg gggatcatgt aactcgcctt gatcgttggg aaccggagct    3300
gaatgaagcc ataccaaacg acgagcgtga caccacgatg cctgtagcaa tggcaacaac    3360
gttgcgcaaa ctattaactg gcgaactact tactctagct tcccggcaac aattaataga    3420
ctggatggag gcggataaag ttgcaggacc acttctgcgc tcggcccttc cggctggctg    3480
gtttattgct gataaatctg gagccggtga gcgtgggtct cgcggtatca ttgcagcact    3540
ggggccagat ggtaagccct cccgtatcgt agttatctac acgacgggga gtcaggcaac    3600
tatggatgaa cgaaatagac agatcgctga gataggtgcc tcactgatta agcattggta    3660
actgtcagac caagtttact catatatact ttagattgat ttaaaacttc attttttaatt    3720 taaaaggatc taggtgaaga tcctttttga taatctcatg accaaaatcc cttaacgtga    3780
gttttcgttc cactgagcgt cagaccccgt agaaaagatc aaaggatctt cttgagatcc    3840 ttttttctg cgcgtaatct gctgcttgca acaaaaaaa ccaccgctac cagcggtggt    3900
ttgtttgccg gatcaagagc taccaactct ttttccgaag gtaactggct tcagcagagc    3960
gcagatacca aatactgtcc ttctagtgta gccgtagtta ggccaccact tcaagaactc    4020
tgtagcaccg cctacatacc tcgctctgct aatcctgtta ccagtggctg ctgccagtgg    4080
cgataagtcg tgtcttaccg ggttggactc aagacgatag ttaccggata aggcgcagcg    4140
gtcgggctga acggggggtt cgtgcacaca gcccagcttg gagcgaacga cctacaccga    4200
actgagatac ctacagcgtg agctatgaga aagcgccacg cttcccgaag ggagaaaggc    4260
ggacaggtat ccggtaagcg gcagggtcgg aacaggagag cgcacgaggg agcttccagg    4320
gggaaacgcc tggtatcttt atagtcctgt cgggtttcgc cacctctgac ttgagcgtcg    4380
atttttgtga tgctcgtcag ggggcggag cctatggaaa aacgccagca acgcggcctt    4440
tttacggttc ctggcctttt gctggccttt tgctcacatg ttctttcctg cgttatcccc    4500
tgattctgtg gataaccgta ttaccgcctt tgagtgagct gataccgctc gccgcagccg    4560
aacgaccgag cgcagcgagt cagtgagcga ggaagcggaa gagcgcccaa tacgcaaacc    4620
gcctctcccc gcgcgttggc cgattcatta atgcaggggc cgctgcggc                4669
```

<210> SEQ ID NO 6
<211> LENGTH: 5246
<212> TYPE: DNA
<213> ORGANISM: Artificial Sequence
<220> FEATURE:
<223> OTHER INFORMATION: Sequences from adenovirus, CAG, and variation
      of human IFN alpha 2b

<400> SEQUENCE: 6

```
catcatcaat aatataccett attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacgatg tggcaaaagt gacgttttg     180 gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
```

```
tccgacaccg ggaggcgcgc cctcgagcta gcccctagtt attaatagta atcaattacg    600
gggtcattag ttcatagccc atatatggag ttccgcgtta cataacttac ggtaaatggc    660
ccgcctggct gaccgcccaa cgaccccgc ccattgacgt caataatgac gtatgttccc    720
atagtaacgc caatagggac tttccattga cgtcaatggg tggagtattt acggtaaact    780
gcccacttgg cagtacatca agtgtatcat atgccaagta cgccccctat tgacgtcaat    840
gacggtaaat ggcccgcctg gcattatgcc cagtacatga ccttatggga ctttcctact    900
tggcagtaca tctacgtatt agtcatcgct attaccatgg tcgaggtgag ccccacgttc    960
tgcttcactc tccccatctc cccccctcc ccacccccaa ttttgtattt atttattttt   1020
taattatttt gtgcagcgat ggggcgggg ggggggggg ggcgcgcgcc aggcggggcg   1080
gggcggggcg aggggcgggg cggggcgagg cggagaggtg cggcggcagc caatcagagc   1140
ggcgcgctcc gaaagtttcc ttttatggcg aggcggcggc ggcggcggcc ctataaaaag   1200
cgaagcgcgc ggcgggcggg agtcgctgcg cgctgccttc gccccgtgcc ccgctccgcc   1260
gccgcctcgc gccgcccgcc ccggctctga ctgaccgcgt tactcccaca ggtgagcggg   1320
cgggacggcc cttctcctcc gggctgtaat tagcgcttgg tttaatgacg cttgtttct   1380
tttctgtggc tgcgtgaaag ccttgagggg ctccgggagc gccggcagga aggaaatggg   1440
cggggagggc cttcgtgcgt cgccgcgccg ccgtccccct ctccctctcc agcctcgggg   1500
ctgtccgcgg gggacggct gccttcgggg gggacgggc agggcggggt tcggcttctg   1560
gcgtgtgacc ggcggctcta gagcctctgc taaccatgtt catgccttct tcttttttcct   1620
acagctcctg gcaacgtgc tggttattgt gctgtctcat catttttggca aagaattgat   1680
taattcgagc gaacgcgtcg agtcgctcgg tacgatttaa attgaattgg gctcgagatc   1740
tgcgatctaa gtaagcttgc atgcctgcag gtcgactcta gactgccatg gccctgacct   1800
tcgccctgct ggtggccctg ctggtgctgt cctgcaagag cagctgcagc gtgggctgcg   1860
acctgccccg acccacagc ctgggcagcc ggcggaccct gatgctgctg cccagatgc   1920
ggcggatcag cctgttcagc tgcctgaagg accggcacga cttcggcttc cccaggaag   1980
agttcggcaa ccagttccag aaggccgaga ccatccccgt gctgcacgag atgatccagc   2040
agatcttcaa cctgttcagc accaaggaca gcagcgccgc ctgggacgag accctgctgg   2100
acaagttcta caccgagctg taccagcagc tgaacgacct ggaagcctgc gtgatccagg   2160
gcgtgggcgt gaccgagacc cccctgatga agaggacag catcctggcc gtgcggaagt   2220
acttccagcg gatcaccctg tacctgaaag agaagaagta cagcccctgc gcctgggaag   2280
tggtgcgggc cgagatcatg cggagcttca gcctgagcac caacctgcag gaaagcctgc   2340
ggagcaaaga gtgaggatcc ccgggtaccg agctcgaatt cttgtagag ttttacttg   2400
ctttaaaaa cctcccacac ctccccctga acctgaaaca taaaatgaat gcaattgttg   2460
ttgttaactt gttattgca gcttataatg gttacaaata aagcaatagc atcacaaatt   2520
tcacaaataa agcatttttt tcactgcatt ctagttgtgg tttgtccaaa ctcatcaatg   2580
tatcgatatc ggcgcgccgg gcccctacgt cacccgcccc gttcccacgc ccgcgccac   2640
gtcacaaact ccaccccctc attatcatat tggcttcaat ccaaaataag gtatattatt   2700
gatgatggcc gcagcggccc ctggcgtaat agcgaagagg cccgcaccga tcgcccttcc   2760
caacagttgc gcagcctgaa tggcgaatgg gacgcgccct gtagcggcgc attaagcgcg   2820
gcgggtgtgg tggttacgcg cagcgtgacc gctacacttg ccagcgccct agcgcccgct   2880
cctttcgctt tcttcccttc ctttctcgcc acgttcgccg gctttccccg tcaagctcta   2940
```

```
aatcgggggc tcccttttagg gttccgattt agtgctttac ggcacctcga ccccaaaaaa    3000
cttgattagg gtgatggttc acgtagtggg ccatcgccct gatagacggt ttttcgccct    3060
ttgacgttgg agtccacgtt ctttaatagt ggactcttgt tccaaactgg aacaacactc    3120
aaccctatct cggtctattc ttttgattta taagggattt tgccgattc ggcctattgg    3180
ttaaaaaatg agctgattta acaaaaattt aacgcgaatt ttaacaaaat attaacgctt    3240
acaatttagg tggcactttt cggggaaatg tgcgcggaac ccctatttgt ttatttttct    3300
aaatacattc aaatatgtat ccgctcatga acaataacc ctgataaatg cttcaataat    3360
attgaaaaag gaagagtatg agtattcaac atttccgtgt cgcccttatt cccttttttg    3420
cggcattttg ccttcctgtt tttgctcacc cagaaacgct ggtgaaagta aaagatgctg    3480
aagatcagtt gggtgcacga gtgggttaca tcgaactgga tctcaacagc ggtaagatcc    3540
ttgagagttt tcgccccgaa aacgttttc caatgatgag cacttttaaa gttctgctat    3600
gtggcgcggt attatcccgt attgacgccg ggcaagagca actcggtcgc cgcatacact    3660
attctcagaa tgacttggtt gagtactcac cagtcacaga aaagcatctt acggatggca    3720
tgacagtaag agaattatgc agtgctgcca taaccatgag tgataacact gcggccaact    3780
tacttctgac aacgatcgga ggaccgaagg agctaaccgc ttttttgcac aacatggggg    3840
atcatgtaac tcgccttgat cgttgggaac cggagctgaa tgaagccata ccaaacgacg    3900
agcgtgacac cacgatgcct gtagcaatgg caacaacgtt gcgcaaacta ttaactggcg    3960
aactacttac tctagcttcc cggcaacaat taatagactg gatggaggcg gataaagttg    4020
caggaccact tctgcgctcg gcccttccgg ctggctggtt tattgctgat aaatctggag    4080
ccggtgagcg tgggtctcgc ggtatcattg cagcactggg gccagatggt aagccctccc    4140
gtatcgtagt tatctacacg acggggagtc aggcaactat ggatgaacga aatagacaga    4200
tcgctgagat aggtgcctca ctgattaagc attggtaact gtcagaccaa gtttactcat    4260
atatacttta gattgattta aaacttcatt tttaatttaa aaggatctag gtgaagatcc    4320
tttttgataa tctcatgacc aaaatccctt aacgtgagtt ttcgttccac tgagcgtcag    4380
accccgtaga aaagatcaaa ggatcttctt gagatccttt ttttctgcgc gtaatctgct    4440
gcttgcaaac aaaaaaacca ccgctaccag cggtggtttg tttgccggat caagagctac    4500
caactctttt tccgaaggta actggcttca gcagagcgca gataccaaat actgtccttc    4560
tagtgtagcc gtagttaggc caccacttca agaactctgt agcaccgcct acatacctcg    4620
ctctgctaat cctgttacca gtggctgctg ccagtggcga taagtcgtgt cttaccgggt    4680
tggactcaag acgatagtta ccggataagg cgcagcggtc gggctgaacg gggggttcgt    4740
gcacacagcc cagcttggag cgaacgacct acaccgaact gagatacta cagcgtgagc    4800
tatgagaaag cgccacgctt cccgaaggga gaaaggcgga caggtatccg gtaagcggca    4860
gggtcggaac aggagagcgc acgagggagc ttccaggggg aaacgcctgg tatctttata    4920
gtcctgtcgg gtttcgccac ctctgacttg agcgtcgatt tttgtgatgc tcgtcagggg    4980
ggcggagcct atgaaaaac gccagcaacg cggccttttt acggttcctg gccttttgct    5040
ggccttttgc tcacatgttc tttcctgcgt tatcccctga ttctgtggat aaccgtatta    5100
ccgcctttga gtgagctgat accgctcgcc gcagccgaac gaccgagcgc agcgagtcag    5160
tgagcgagga agcggaagag cgcccaatac gcaaaccgcc tctccccgcg cgttggccga    5220
ttcattaatg cagggggccgc tgcggc                                        5246
```

<210> SEQ ID NO 7
<211> LENGTH: 582
<212> TYPE: DNA
<213> ORGANISM: Homo sapiens

<400> SEQUENCE: 7

```
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta atttctatgc ctggaagagg     240
atggaggtcg ggcagcaggc cgtagaagtc tggcagggcc tggccctgct gtcggaagct     300
gtcctgcggg gccaggccct gttggtcaac tcttcccagc cgtgggagcc cctgcagctg     360
catgtggata aagccgtcag tggccttcgc agcctcacca ctctgcttcg ggctctggga     420
gcccagaagg aagccatctc ccctccagat gcggcctcag ctgctccact ccgaacaatc     480
actgctgaca ctttccgcaa actcttccga gtctactcca atttcctccg gggaaagctg     540
aagctgtaca caggggaggc ctgcaggaca ggggacagat ga                        582
```

<210> SEQ ID NO 8
<211> LENGTH: 645
<212> TYPE: DNA
<213> ORGANISM: Homo sapiens

<400> SEQUENCE: 8

```
ggcgcgccaa gcttgcatgc ctgcaggtcg actctagact gccatggcct tgacctttgc      60
tttactggtg gccctcctgg tgctcagctg caagtcaagc tgctctgtgg gctgtgatct     120
gcctcaaacc cacagcctgg gtagcaggag gaccttgatg ctcctggcac agatgaggag     180
aatctctctt ttctcctgct tgaaggacag acatgacttt ggatttcccc aggaggagtt     240
tggcaaccag ttccaaaagg ctgaaaccat ccctgtcctc catgagatga tccagcagat     300
cttcaatctc ttcagcacaa aggactcatc tgctgcttgg gatgagaccc tcctagacaa     360
attctacact gaactctacc agcagctgaa tgacctggaa gcctgtgtga tacaggggt     420
gggggtgaca gagactcccc tgatgaagga ggactccatt ctggctgtga ggaaatactt     480
ccaaagaatc actctctatc tgaaagagaa gaaatacagc ccttgtgcct gggaggttgt     540
cagagcagaa atcatgagat ctttttcttt gtcaacaaac ttgcaagaaa gtttaagaag     600
taaggaatga ggatccccgg gtaccgagct cgaattctta attaa                    645
```

<210> SEQ ID NO 9
<211> LENGTH: 188
<212> TYPE: PRT
<213> ORGANISM: Homo sapiens

<400> SEQUENCE: 9

```
Met Ala Leu Thr Phe Ala Leu Leu Val Ala Leu Leu Val Leu Ser Cys
  1               5                  10                  15

Lys Ser Ser Cys Ser Val Gly Cys Asp Leu Pro Gln Thr His Ser Leu
             20                  25                  30

Gly Ser Arg Arg Thr Leu Met Leu Leu Ala Gln Met Arg Arg Ile Ser
         35                  40                  45

Leu Phe Ser Cys Leu Lys Asp Arg His Asp Phe Gly Phe Pro Gln Glu
     50                  55                  60

Glu Phe Gly Asn Gln Phe Gln Lys Ala Glu Thr Ile Pro Val Leu His
 65                  70                  75                  80
```

```
Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
           100                 105                 110

Gln Gln Leu Asn Asp Leu Glu Ala Cys Val Ile Gln Gly Val Gly Val
               115                 120                 125

Thr Glu Thr Pro Leu Met Lys Glu Asp Ser Ile Leu Ala Val Arg Lys
   130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
               165                 170                 175

Ser Thr Asn Leu Gln Glu Ser Leu Arg Ser Lys Glu
               180                 185

<210> SEQ ID NO 10
<211> LENGTH: 193
<212> TYPE: PRT
<213> ORGANISM: Homo sapiens

<400> SEQUENCE: 10

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
               20                  25                  30

Ile Cys Asp Ser Arg Val Leu Glu Arg Tyr Leu Leu Glu Ala Lys Glu
               35                  40                  45

Ala Glu Asn Ile Thr Thr Gly Cys Ala Glu His Cys Ser Leu Asn Glu
   50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
               100                 105                 110

Gln Pro Trp Glu Pro Leu Gln Leu His Val Asp Lys Ala Val Ser Gly
               115                 120                 125

Leu Arg Ser Leu Thr Thr Leu Leu Arg Ala Leu Gly Ala Gln Lys Glu
   130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
               165                 170                 175

Arg Gly Lys Leu Lys Leu Tyr Thr Gly Glu Ala Cys Arg Thr Gly Asp
               180                 185                 190

Arg

<210> SEQ ID NO 11
<211> LENGTH: 2045
<212> TYPE: DNA
<213> ORGANISM: Artificial Sequence
<220> FEATURE:
<223> OTHER INFORMATION: CAG-EPO expression cassette
```

<400> SEQUENCE: 11

```
ggcgcgccct cgagctagcc cctagttatt aatagtaatc aattacgggg tcattagttc      60
atagcccata tatggagttc cgcgttacat aacttacggt aaatggcccg cctggctgac     120
cgcccaacga ccccccgccca ttgacgtcaa taatgacgta tgttcccata gtaacgccaa    180
tagggacttt ccattgacgt caatgggtgg agtatttacg gtaaactgcc cacttggcag     240
tacatcaagt gtatcatatg ccaagtacgc ccctattga cgtcaatgac ggtaaatggc      300
ccgcctggca ttatgcccag tacatgacct tatgggactt tcctacttgg cagtacatct    360
acgtattagt catcgctatt accatggtcg aggtgagccc cacgttctgc ttcactctcc    420
ccatctcccc ccctcccca cccccaattt tgtatttatt tattttttaa ttattttgtg     480
cagcgatggg ggcggggggg ggggggggcg cgcgccaggc ggggcgggc ggggcgaggg     540
gcggggcggg gcgaggcgga gaggtgcggc ggcagccaat cagagcggcg cgctccgaaa    600
gtttcctttt atggcgaggc ggcggcggcg gcggccctat aaaaagcgaa gcgcgcggcg    660
ggcgggagtc gctgcgcgct gccttcgccc cgtgccccgc tccgccgccg cctcgcgccg    720
cccgccccgg ctctgactga ccgcgttact cccacaggtg agcggcgggg acggcccttc    780
tcctccgggc tgtaattagc gcttggttta atgacggctt gtttcttttc tgtggctgcg    840
tgaaagcctt gagggggctcc gggagcgccg gcaggaagga atgggcggg agggccttc     900
gtgcgtcgcc gcgccgccgt ccccttctcc ctctccagcc tcggggctgt ccgcgggggg    960
acggctgcct tcgggggggga cggggcaggg cggggttcgg cttctggcgt gtgaccggcg   1020
gctctagagc ctctgctaac catgttcatg ccttcttctt tttcctacag ctcctgggca   1080
acgtgctggt tattgtgctg tctcatcatt ttggcaaaga attgattaat tcgagcgaac   1140
gcgtcgagtc gctcggtacg atttaaattg aattgggctc gagatctgcg atctaagtaa   1200
gcttgcatgc ctgcaggtcg actctagact gccatggggg tgcacgaatg tcctgcctgg   1260
ctgtggcttc tcctgtccct gctgtcgctc cctctgggcc tcccagtcct gggcgcccca   1320
ccacgcctca tctgtgacag ccgagtcctg gagaggtacc tcttggaggc caaggaggcc   1380
gagaatatca cgacgggctg tgctgaacac tgcagcttga atgagaatat cactgtccca   1440
gacaccaaag ttaatttcta tgcctggaag aggatggagg tcgggcagca ggccgtagaa   1500
gtctggcagg gcctggccct gctgtcggaa gctgtcctgc ggggccaggc cctgttggtc   1560
aactcttccc agccgtggga gcccctgcag ctgcatgtgg ataaagccgt cagtggcctt   1620
cgcagcctca ccactctgct tcgggctctg gagcccagag aggaagccat ctcccctcca   1680
gatgcggcct cagctgctcc actccgaaca atcactgctg acactttccg caaactcttc   1740
cgagtctact ccaatttcct ccggggaaag ctgaagctgt acacagggga ggcctgcagg   1800
acaggggaca gatgaggatc cccgggtacc gagctcgaat tctttgtaga ggttttactt   1860
gctttaaaaa acctcccaca cctccccctg aacctgaaac ataaaatgaa tgcaattgtt   1920
gttgttaact tgtttattgc agcttataat ggttacaaat aaagcaatag catcacaaat   1980
ttcacaaata aagcattttt ttcactgcat tctagttgtg gtttgtccaa actcatcaat   2040
gtatc                                                               2045
```

<210> SEQ ID NO 12
<211> LENGTH: 1177
<212> TYPE: DNA
<213> ORGANISM: Artificial Sequence
<220> FEATURE:
<223> OTHER INFORMATION: CAG promoter sequence

<400> SEQUENCE: 12

```
ctagttatta atagtaatca attacggggt cattagttca tagcccatat atggagttcc      60
gcgttacata acttacggta aatggcccgc ctggctgacc gcccaacgac ccccgcccat     120
tgacgtcaat aatgacgtat gttcccatag taacgccaat agggactttc cattgacgtc     180
aatgggtgga gtatttacgg taaactgccc acttggcagt acatcaagtg tatcatatgc     240
caagtacgcc ccctattgac gtcaatgacg gtaaatggcc cgcctggcat tatgcccagt     300
acatgacctt atgggacttt cctacttggc agtacatcta cgtattagtc atcgctatta     360
ccatggtcga ggtgagcccc acgttctgct tcactctccc catctccccc ccctccccac     420
ccccaatttt gtatttattt attttttaat tattttgtgc agcgatgggg gcggggggggg    480
ggggggcgc gcgccaggcg gggcggggcg gggcgagggg cggggcgggg cgaggcggag      540
aggtgcggcg gcagccaatc agagcggcgc gctccgaaag tttcctttta tggcgaggcg     600
gcggcggcgg cggccctata aaaagcgaag cgcgcggcgg gcgggagtcg ctgcgcgctg     660
ccttcgcccc gtgccccgct ccgccgccgc ctcgcgccgc ccgccccggc tctgactgac     720
cgcgttactc ccacaggtga gcgggcggga cggcccttct cctccgggct gtaattagcg     780
cttggtttaa tgacggcttg tttcttttct gtggctgcgt gaaagccttg aggggctccg     840
ggagcgccgg caggaaggaa atgggcgggg agggccttcg tgcgtcgccg cgccgccgtc     900
cccttctccc tctccagcct cggggctgtc cgcgggggga cggctgcctt cggggggggac    960
ggggcagggc ggggttcggc ttctggcgtg tgaccggcgg ctctagagcc tctgctaacc    1020
atgttcatgc cttcttcttt ttcctacagc tcctgggcaa cgtgctggtt attgtgctgt    1080
ctcatcattt tggcaaagaa ttgattaatt cgagcgaacg cgtcgagtcg ctcggtacga    1140
tttaaattga attgggctcg agatctgcga tctaagt                            1177
```

<210> SEQ ID NO 13
<211> LENGTH: 230
<212> TYPE: DNA
<213> ORGANISM: Simian virus 40

<400> SEQUENCE: 13

```
ggatccccgg gtaccgagct cgaattcttt gtagaggttt tacttgcttt aaaaaacctc      60
ccacacctcc ccctgaacct gaaacataaa atgaatgcaa ttgttgttgt taacttgttt     120
attgcagctt ataatggtta caaataaagc aatagcatca caaatttcac aaataaagca     180
tttttttcac tgcattctag ttgtggtttg tccaaactca tcaatgtatc                230
```

<210> SEQ ID NO 14
<211> LENGTH: 21
<212> TYPE: DNA
<213> ORGANISM: Artificial Sequence
<220> FEATURE:
<223> OTHER INFORMATION: multiple cloning sites

<400> SEQUENCE: 14

```
ggcgcgccct cgagctagcc c                                                21
```

<210> SEQ ID NO 15
<211> LENGTH: 35
<212> TYPE: DNA
<213> ORGANISM: Artificial Sequence
<220> FEATURE:
<223> OTHER INFORMATION: multiple cloning sites

```
<400> SEQUENCE: 15
aagcttgcat gcctgcaggt cgactctaga ctgcc                                35
```

LONG LASTING DRUG FORMULATIONS

CROSS REFERENCE TO RELATED APPLICATIONS

This application claims the benefit of U.S. Ser. No. 13/346,761, filed on Jan. 10, 2012 (and entitled LONG LASTING DRUG FORMULATIONS), which is a Continuation in Part of U.S. application Ser. No. 13/160,632 filed Jun. 15, 2011, which claims priority from U.S. Provisional Application Ser. No. 61/355,029 filed Jun. 15, 2010 and U.S. Provisional Application Ser. No. 61/414,921 filed Nov. 18, 2010; which is a Continuation in Part application of U.S. application Ser. No. 11/898,481, filed Sep. 12, 2007, which claims priority from U.S. Provisional Application Ser. No. 60/844,351, filed Sep. 14, 2006; all of which are hereby incorporated by reference in their entirety.

FIELD OF THE INVENTION

This invention is directed to long-lasting therapeutic formulations comprising a genetically modified micro-organ comprising a vector comprising a nucleic acid sequence encoding a therapeutic polypeptide, such as erythropoietin, operably linked to one or more regulatory sequences and their methods of use.

BACKGROUND OF THE INVENTION

Therapeutic agents can be delivered orally, transdermally, by inhalation, by injection or by depot with slow release. However, the method of delivery is limited by the processing that the agent is subjected to in the recipient, by the requirement for frequent administration, and limitations on the size of molecules that can be utilized. For some of the methods, the amount of therapeutic agent varies between administrations.

Protein production techniques which involve the sub-cloning of a desired nucleic acid sequence/fragment into a vector which is subsequently used for modifying specific host cells, which are meant to produce the desired protein for further purification steps are limited in the amount of protein expressed, protein secretion, post-translational modifications (such as glycosylation and the accurate folding of the protein), etc. Moreover, even if a high-level of protein production could be achieved, large quantities of the recombinant protein must then be produced and purified to be free of contaminants. Development of a purification scheme is a very lengthy process. And once purified recombinant protein has been obtained, it must be further formulated to render it stable and acceptable for introduction into animals or humans. Furthermore, even formulated, purified recombinant proteins have a finite shelf life due to maintenance and storage limitations; often requiring repeated purification and formulation of more protein. The process of developing an appropriate formulation is time consuming, difficult, and costly, as well.

Thus, there is a widely recognized need for long-lasting protein-based therapeutic molecules that have the requisite post-translational modifications to preserve their biological activity, which are produced inexpensively and quickly without the need for the laborious and costly methods typically associated with obtaining high-levels of recombinant proteins.

Some researchers have attempted to obtain in vivo expression of recombinant gene products via gene therapy. Typically viral vectors are used to transduce cells in vivo to express recombinant gene products. These viral-based vectors have advantageous characteristics, such as the natural ability to infect the target tissue. However, retrovirus-based vectors require integration within the genome of the target tissue to allow for recombinant product expression (with the potential to activate resident oncogenes) and can only be used to transduce actively dividing tissues. Viral vectors are also often not able to sustain long-term transgene expression, which may be due at least in part to their elimination due to secondary host immune responses.

Accordingly, there remains a need in the art for recombinant gene product formulations that have consistently high expression levels lasting for several weeks or more and for methods of using those formulations to treat disease.

SUMMARY OF THE INVENTION

The invention provides, in one embodiment, a long-lasting therapeutic formulation comprising a genetically modified micro-organ, said micro-organ comprising a vector comprising a nucleic acid sequence operably linked to one or more regulatory sequences, wherein said nucleic acid sequence encodes a therapeutic polypeptide and whereby administration of said formulation increases blood hemoglobin ("Hb") levels over basal level and said increase is maintained for at least one month. In one embodiment, the vector is a helper-dependent adenovirus vector.

In one embodiment, the therapeutic polypeptide is erythropoietin. In one embodiment, the erythropoietin is encoded by SEQ ID No. 7. In one embodiment, this invention provides a long-lasting erythropoietin formulation comprising at least one genetically modified micro-organ that expresses and secretes erythropoietin, said micro-organ comprising a helper-dependent adenovirus vector, said vector comprising a nucleic acid sequence encoding erythropoietin operably linked to one or more regulatory sequences, wherein said nucleic acid comprises SEQ ID No. 11.

In another embodiment, the invention provides a method of providing a therapeutic polypeptide to a subject in need over a sustained period comprising providing one or more genetically modified micro-organs, said micro-organs comprising a vector comprising a nucleic acid sequence operably linked to one or more regulatory sequences; and implanting said genetically modified micro-organ in said subject, wherein said nucleic acid sequence encodes a therapeutic polypeptide and whereby said formulation increases Hb levels over the basal level and said increase is maintained for at least one month. In yet another embodiment, the increase is maintained for greater than one month. In one embodiment, the Hb levels are maintained within a range of 9-11 g/dl hemoglobin. In another embodiment, the Hb levels are maintained within a range of 10-12 g/dl. In one embodiment, the Hb levels are maintained for at least one month.

In one embodiment, the vector is a helper-dependent adenovirus vector. In one embodiment, the therapeutic polypeptide is erythropoietin. In one embodiment, the erythropoietin is encoded by SEQ ID No. 7. In one embodiment, the subject in need is suffering from anemia. In another embodiment, the subject in need is suffering from an infection. In yet another embodiment, the subject in need is suffering from cancer.

In one embodiment, this invention provides a method of treating anemia in a human subject in need over a sustained time period comprising the steps of: a. providing at least one genetically modified micro-organ that expresses and secretes erythropoietin, wherein the micro-organ comprises a helper-dependent adenovirus vector comprising a nucleic acid sequence encoding erythropoietin operably linked to one or more regulatory sequences; b. determining erythropoietin secretion levels of the at least one genetically modified micro-organ in vitro; c. implanting the at least one genetically modified micro-organ in the human subject at an effective dosage; and d. measuring hemoglobin levels in the blood of the subject, wherein the measured hemoglobin levels in the subject are maintained at 9-11 g/dl in at least 50% of the measurements for at least one month.

In one embodiment, this invention provides an effective dosage of 18-150 IU erythropoietin/Kg bodyweight of said subject/day. In one embodiment, the effective dosage is determined based on a subject's weight, historical hemoglobin levels and the average amount of erythropoietin previously administered to the subject for one month prior to said implanting step.

In one embodiment, this invention provides a method of increasing or maintaining physiological hemoglobin levels in a human subject over a sustained period of time comprising the steps of: a. providing at least one genetically modified micro-organ that expresses and secretes erythropoietin, the micro-organ comprising a helper-dependent adenovirus vector comprising a nucleic acid sequence encoding erythropoietin operably linked to one or more regulatory sequences; b. determining erythropoietin secretion levels of the at least one genetically modified micro-organ in vitro; c. implanting the at least one genetically modified micro-organ in the subject at an effective dosage; and d. measuring hemoglobin levels in the blood of the subject, wherein the increased or maintained physiological hemoglobin levels in said subject are maintained at 9-11 g/dl in at least 50% of the measurements for at least one month.

DETAILED DESCRIPTION OF THE PRESENT INVENTION

Figure 1:
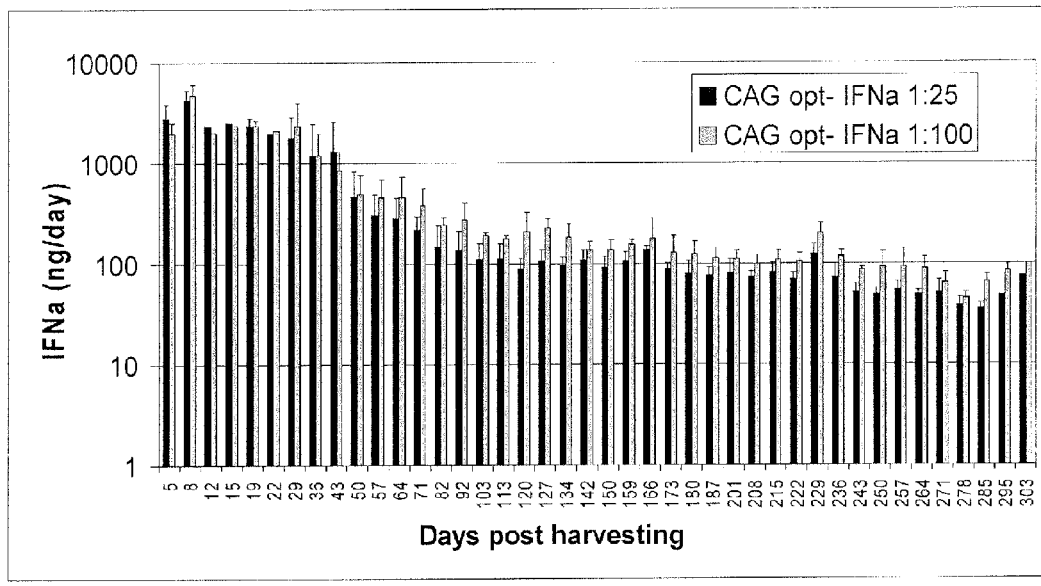
FIG. 1 presents levels of recombinant optimized human interferon-alpha (IFNα) produced in vitro by the formulations of the instant invention.

In some embodiments, the instant invention is directed to long-lasting therapeutic formulations comprising a genetically modified, tissue-based micro-organ comprising a vector comprising a nucleic acid sequence encoding a therapeutic polypeptide, such as erythropoietin, operably linked to one or more regulatory sequences and their methods of use.

The invention provides, in one embodiment, a long-lasting therapeutic formulation comprising a genetically modified micro-organ, said micro-organ comprising a vector comprising a nucleic acid sequence operably linked to one or more regulatory sequences, wherein said nucleic acid sequence encodes a therapeutic polypeptide and whereby administration of the therapeutic formulation increases the level of hemoglobin ("Hb") and the increase is maintained for at least one month. In another embodiment, the increase is for greater than one month. In another embodiment, the hemoglobin level is increased and the increase is maintained for greater than six months.

In another embodiment, this invention provides a long-lasting therapeutic formulation comprising a genetically modified micro-organ, said micro-organ comprising a vector comprising a nucleic acid sequence operably linked to one or more regulatory sequences, wherein said nucleic acid sequence encodes a therapeutic polypeptide and whereby administration of the formula increases blood Hb levels over basal levels and the increase is maintained for at least one month and wherein the vector is a helper-dependent adenovirus vector.

In yet another embodiment, this invention provides a long-lasting erythropoietin formulation comprising at least one genetically modified micro-organ that expresses and secretes erythropoietin, the micro-organ comprising a helper-dependent adenovirus vector, the vector comprising a nucleic acid sequence encoding erythropoietin operably linked to one or more regulatory sequences, wherein the nucleic acid encoding erythropoietin operably linked to one or more regulatory sequences comprises SEQ ID No. 11. Administration of such a formulation at an effective dosage to a human subject in need can increase and/or maintain hemoglobin levels in the subject to physiological hemoglobin levels for at least one month.

As used herein, the term "subject" refers to a human subject. The term "subject" may also be referred to herein as a "patient". Subjects may be naïve, e.g., a patient naïve to EPO. Alternatively, subjects may be previously exposed to a therapeutic polypeptide, e.g., EPO, for instance by way of erythroid stimulating activity (ESA; also termed erythropoietic stimulating agent) injection therapy.

As used herein, the term "increased hemoglobin levels" refers to an increase in blood Hb levels over basal levels in response to administration of a long-lasting therapeutic formulation of the current invention to a subject in need. As used herein, the term "increased hemoglobin levels" may also be referred to herein as "hemoglobin response". Administration of a GMMO to a naïve subject may increase hemoglobin levels to a therapeutic level. Administration of a GMMO to a subject previously exposed to EPO may maintain hemoglobin levels at a therapeutic level.

In one embodiment, the Hb response refers to an increase in Hb levels such that Hb levels range between 9-11 gm/dl, which is the current FDA recommended range. In another embodiment, the Hb levels range between 9.5-12.6 gm/dl. In yet another embodiment, the Hb levels range between 10-12 gm/dl. In still another embodiment, the Hb levels range between 9-13.2 gm/dl. In a further embodiment, the Hb levels range between 8.5-13.8 gm/dl. In another embodiment, the Hb levels range between 8-14.4 gm/dl.

As Hb levels in blood may oscillate slightly from day to day, the range increase in Hb response may in certain situations represent an average increase over any given time period. Measurements made over a given time period may reflect this oscillation. For example, the increased Hb may be maintained for 90% of measurement over any given time period within a target range, as for example presented above. In other words, 90% of measurements made during at least one month or 90% of measurements made over at least six months, or at least one year may be within the Hb target range. Alternatively, Hb levels may be increased or maintained within the targeted range for 80% of measurements over any given time period. Further, Hb levels may be increased or maintained within the targeted range for 70% of measurements over any given time period. Alternatively, Hb levels may be increased or maintained within the targeted range for 60% of measurements over any given time period. Or, Hb levels may be increased or maintained within the targeted range for 50% of measurements over any given time period.

Hemoglobin measurements may be made on a regular basis or irregular basis. In certain cases, measurements of blood Hb levels may be made once per week. Alternatively, measurements of blood Hb may be more or less frequent, e.g., twice per week or once every two weeks or once a month. In one embodiment, blood measurements are made once a week. In another embodiment, twice a week. In yet another embodiment, three times a week. In still another embodiment, measurements are made once every two weeks. In a further embodiment, measurements are made once a month. In one embodiment, measurements are made on a regularly scheduled basis. In another embodiment, measurements are made on an as "needed" basis. Measurements may be made more or less frequently, dependent on need.

In some embodiments, increased Hb levels are maintained within a given range for at least 90% of the time that Hb levels are increased. In other embodiments, Hb levels are maintained for at least 80% of the time. In yet other embodiments, Hb levels are maintained for at least 70% of the time. In still other embodiments, Hb levels are maintained for at least 60% of the time. In a further embodiment, Hb levels are maintained for at least 50% of the time.

As used herein, the term "hematocrit" refers to the packed cell volume or erythrocyte volume fraction as a percentage of the concentration of red blood cells in blood. As used herein, increases in Hb levels reflect increases in hematocrit.

For patients previously treated with ESA injection therapy, administration of "human erythropoietin-genetically modified micro-organ" ("hEPO-GMMO") in place of ESA injections prevents a decrease in Hb levels to their natural nadir. In one embodiment, wherein the patient has been treated with ESA, Hb response refers to a prevention of the decrease of Hb level that would otherwise occur naturally and maintenance of elevated Hb levels, compared with the patient's natural nadir. In one embodiment, hEPO-GMMO administration prevents a decrease in Hb levels. In this way Hb levels may be maintained within the therapeutic window.

As used herein, the term "erythropoiesis" refers to the process of red blood cell formation or production. Erythropoietin is a required element in the regulation of erythropoiesis, i.e., red blood cell production. The measure of an Hb response is also a measure of red blood cell formation, i.e., erythropoiesis.

As used herein, a sustained "hemoglobin response" may also be referred to as sustained "erythropoiesis" having all the qualities and properties of an Hb response.

In another embodiment, the invention provides a long-lasting therapeutic formulation comprising a genetically modified micro-organ, said micro-organ comprising a vector comprising a nucleic acid sequence operably linked to one or more regulatory sequences, wherein said nucleic acid sequence encodes a therapeutic polypeptide and whereby blood Hb level is increased over basal level following administration of the formulation and the increase is maintained for greater than one month in a subject, wherein the subject may be an immuno-competent host.

In one embodiment, the expression level of the nucleic acid is increased by more than 5% over basal levels in an immuno-competent host, while in another embodiment, the vector is a helper-dependent adenovirus vector.

The invention provides a long-lasting therapeutic formulation and methods of use thereof, where the formulation comprises a genetically modified micro-organ. The term "micro-organ" as used herein, refers in one embodiment, to an isolated tissue or organ structure derived from or identical to an explant that has been prepared in a manner conducive to cell viability and function. In one embodiment, a micro-organ maintains at least some in vivo structures, or in another embodiment, interactions, similar to the tissues or organ from which it is obtained. In one embodiment, a micro-organ is an intact, isolated tissue slice. In another embodiment, micro-organs retain the micro-architecture and the three dimensional structure of the tissue or organ from which they were derived and have dimensions selected so as to allow passive diffusion of adequate nutrients and gases to cells within the micro-organ and diffusion of cellular waste out of the cells of the micro-organ so as to minimize cellular toxicity and concomitant cell death due to insufficient nutrition and/or accumulation of waste. In one embodiment, a micro-organ is a sliver of dermal tissue.

In one embodiment, a micro-organ is 1-2 mm in diameter and 30-40 mm in length. In another embodiment, the diameter of a micro-organ may be, for example, 1-3 mm, 1-4 mm, 2-4 mm, 0.5-3.5 mm, 1.5-2.5 or 1.5-10 mm. In another embodiment the diameter of a micro-organ may be, for example, approximately 2 mm or approximately 1.5 mm. In another embodiment, the length of the micro-organ may be 5-100 mm, 10-60 mm, 20-60 mm, 20-50 mm, 20-40 mm, 20-100 mm, 30-100 mm, 40-100 mm, 50-100 mm, 60-100 mm, 70-100 mm, 80-100 mm, or 90-100 mm. In another embodiment, the length of the micro-organ may be approximately 20 mm, approximately 30 mm, approximately 40 mm, or approximately 50 mm. In one embodiment, a micro-organ is smaller than 1.5 cm$^2$, and in another embodiment, less than 1 cm$^2$. In another embodiment, the diameter is less than 1.5 cm, and in another embodiment, the length is less than 1.5 cm.

In one embodiment, a micro-organ is an explant. In one embodiment, a micro-organ is tissue-derived. In another embodiment, a micro-organ is a section or portion or part of a tissue. In another embodiment, a micro-organ is a section or portion or part of an organ. A micro-organ can be distinguished from a skin graft, in one embodiment, in that it is specifically designed to survive for long periods of time in vivo and in vitro and, in another embodiment, in that its dimensions are specifically selected so as to allow passive diffusion of adequate nutrients and gases to cells within the micro-organ and diffusion of cellular waste out of the cells of the micro-organ, which in one embodiment minimizes cellular toxicity and concomitant cell death due to insufficient nutrition and/or accumulation of waste. Thus, in one embodiment, a micro-organ is not a skin graft. In another embodiment, a micro-organ can be distinguished from a collection of isolated cells, which in one embodiment, are grown on a natural or artificial scaffold, in that micro-organs maintain the micro-architecture and the three dimensional structure of the tissue or organ from which they were derived. Thus, in one embodiment, a micro-organ is not one or more cell types grown on a scaffold or within a gel.

A detailed description of micro-organs can be found in US-2003-0152562, which is incorporated herein by reference in its entirety.

Earlier patent applications (WO 03/006669, WO 03/03585, WO 04/099363, which are incorporated in-full herein by reference) described micro-organs, which can be modified to express a gene product of interest, that may be sustained outside the body in an autonomously functional state for an extended period of time, and may then be implanted subcutaneously or in other locations within the body for the purpose of treating diseases or disorders. In one embodiment, a micro-organ that is modified to express a gene product of interest is a therapeutic micro-organ. The therapeutic micro-organs of the present invention unexpectedly showed a much longer-term expression profile of a gene product of interest in vitro and in vivo.

As used herein, the term "explant" refers, in one embodiment, to a tissue or organ or a portion thereof removed from its natural growth site in an organism and placed in a culture medium for a period of time. In one embodiment, the tissue or organ is viable, in another embodiment, metabolically active, or a combination thereof. As used herein, the term "explant" may, in some embodiments, be used interchangeably with "micro-organ" or "micro-organ explant".

As used herein, the term "microarchitecture" refers, in one embodiment, to a characteristic of the explant in which some or all of the cells of the tissue explant maintain, in vitro, physical and/or functional contact with at least one cell or non-cellular substance with which they were in physical and/or functional contact in vivo.

In another embodiment, micro-organ explants maintain the three-dimensional structure of the tissue or organ from which they were derived. In one embodiment, micro-organ explants retain the spatial interactions, e.g. cell-cell, cell-matrix and cell-stromal interactions, and the orientation of the tissue from which they were derived. In one embodiment, preservation of spatial interactions such as described above permit the maintenance of biological functions of the explant, such as secretion of autocrine and paracrine factors and other extracellular stimuli, which in one embodiment, provide long term viability to the explant. In one embodiment, at least some of the cells of the micro-organ explant maintain, in vitro or in vivo after implantation, their physical and/or functional contact with at least one cell or non-cellular substance with which they were in physical and/or functional contact in vivo. In one embodiment, some of the cells refers to at least about 50%, in another embodiment, at least about 60%, in another embodiment at least about 70%, in another embodiment, at least about 80%, and in another embodiment, at least about 90% or more of the cells of the population. In another embodiment, the cells of the explant maintain at least one biological activity of the organ or tissue from which they are isolated.

In one embodiment, the term "about", refers to a deviance of between 0.0001-5% from the indicated number or range of numbers. In one embodiment, the term "about", refers to a deviance of between 1-10% from the indicated number or range of numbers. In one embodiment, the term "about", refers to a deviance of up to 25% from the indicated number or range of numbers.

In some embodiments, any of the formulation of this invention will comprise a genetically modified micro-organ (GMMO), in any form or embodiment as described herein. As used herein, the term "GMMO" may also refer to a "Biopump". In some embodiments, any of the formulations of this invention will consist of a genetically modified micro-organ, in any form or embodiment as described herein. In some embodiments, of the compositions of this invention will consist essentially of a genetically modified micro-organ, in any form or embodiment as described herein. In some embodiments, the term "comprise" refers to the inclusion of the indicated active agent, such as the genetically modified micro-organ, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

Further, as used herein, the term "comprising" is intended to mean that the system includes the recited elements, but not excluding others which may be optional. By the phrase "consisting essentially of" it is meant a method that includes the recited elements but exclude other elements that may have an essential significant effect on the performance of the method. "Consisting of" shall thus mean excluding more than traces of other elements. Embodiments defined by each of these transition terms are within the scope of this invention.

Similarly, in some embodiments, the vector of and for use in the methods of the present invention comprise a nucleic acid sequence operably linked to one or more regulatory sequences, wherein said nucleic acid sequence encodes a therapeutic polypeptide. In another embodiment, the vector consists essentially of such a nucleic acid sequence, and in another embodiment, the vector consists of such a nucleic acid sequence. In one embodiment, the nucleic acid operably linked to one or more regulatory sequences comprises the nucleic acids of SEQ ID No. 11.

Examples of mammals from which the micro-organs can be isolated include humans and other primates, swine, such as wholly or partially inbred swine (e.g., miniature swine, and transgenic swine), rodents, etc. Micro-organs may be processed from tissue from a variety of organs, which in one embodiment is the skin, the dermis, the lymph system, the pancreas, the liver, the gallbladder, the kidney, the digestive tract, the respiratory tract, the reproductive system, the urinary tract, the blood, the bladder, the cornea, the prostate, the bone marrow, the thymus, the spleen, or a combination thereof. Explants from these organs may comprise islet of Langerhans cells, hair follicles, glands, epithelial and connective tissue cells, or a combination thereof arranged in a microarchitecture similar to the microarchitecture of the organ from which the explant was obtained. In one embodiment, the microarchitecture of the organ from which the explant was obtained may be discerned or identified in the micro-organ explant using materials, apparati, and/or methods known in the art.

In one embodiment, the present invention provides a formulation and methods of use thereof comprising a genetically modified micro-organ. In one embodiment, the term "genetically modified micro-organ" or "GMMO" refers to a micro-organ that expresses at least one recombinant gene product. In other embodiments, reference to a micro-organ does not necessarily refer to a non-genetically modified micro-organ, but may also refer in some instances to a genetically modified micro-organ as will be clear from the context to one of skill in the art. In one embodiment, the phrase "gene product" refers to proteins, polypeptides, peptides and functional RNA molecules. In one embodiment, the gene product encoded by the nucleic acid molecule is the desired gene product to be supplied to a subject. Examples of such gene products include proteins, peptides, glycoproteins and lipoproteins normally produced by cells of the recipient subject. In one embodiment, the gene product is not naturally occurring in the organism from which the micro-organ was harvested and/or in the organism in which the GMMO is implanted, while in another embodiment, the gene product is naturally occurring. In one embodiment, the gene product of the GMMO is similar or identical to a gene product endogenously expressed by one or more cells of the micro-organ. In one embodiment, genetic modification increases the level of a gene product that would be produced in a non-genetically modified micro-organ. In another embodiment, the gene product expressed by the GMMO is not similar or identical to a gene product endogenously expressed by one or more cells of the micro-organ. In another embodiment, the gene product encoded by the nucleic acid molecule encodes a molecule that directly or indirectly controls expression of a gene of interest. In another embodiment, the gene product encoded by the nucleic acid molecule up-regulates or down-regulates the expression levels of the desired gene product to be supplied to a subject.

In another embodiment, genetic modification of a micro-organ may modify the expression profile of an endogenous gene. This may be achieved, for example, by introducing an enhancer, or a repressible or inducible regulatory element for controlling the expression of an endogenous gene.

Any methodology known in the art can be used for genetically altering the micro-organ explant. Any one of a number of different vectors can be used, such as viral vectors, plasmid vectors, linear DNA, etc., as known in the art, to introduce an exogenous nucleic acid fragment encoding a therapeutic agent into target cells and/or tissue. These vectors can be inserted, for example, using infection, transduction, transfection, calcium-phosphate mediated transfection, DEAE-dextran mediated transfection, electroporation, liposome-mediated transfection, biolistic gene delivery, liposomal gene delivery using fusogenic and anionic liposomes (which are an alternative to the use of cationic liposomes), direct injection, receptor-mediated uptake, magnetoporation, ultrasound, or any combination thereof, as well as other techniques known in the art (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). The polynucleotide segments encoding sequences of interest can be ligated into an expression vector system suitable for transducing mammalian cells and for directing the expression of recombinant products within the transduced cells. The introduction of the exogenous nucleic acid fragment is accomplished by introducing the vector into the vicinity of the micro-organ. Once the exogenous nucleic acid fragment has been incorporated into the cells using any of the techniques described above or known in the art, the production and/or the secretion rate of the therapeutic agent encoded by the nucleic acid fragment can be quantified. In one embodiment, the term "exogenous" refers to a substance that originated outside, for example a nucleic acid that originated outside of a cell or tissue.

In one embodiment, a micro-organ of the formulation and methods of the present invention comprises a vector, which in one embodiment, facilitates recombinant gene expression. In one embodiment, the vector is a non-immunogenic gene transfer agent such as a nonviral vector (e.g. DNA plasmids or minicircle DNA), a "gutless" viral vector i.e. without endogenous genes (which in one embodiment, is due to a deletion, while in another embodiment, due to an insertion, substitution or deletion in a gene that prevents gene expression), a helper-dependent adenovirus (HDAd) vector, or adeno associated virus AAV (which in one embodiment is single stranded and in another embodiment, double stranded). In another embodiment, said formulation is so chosen such that recombinant gene expression results in lack of toxicity or immune-mediated rejection of the gene product by the micro-organ. In one embodiment, the vector is virally derived, and in another embodiment, the vector is a plasmid. In one embodiment, the virally-derived vector is derived from adenovirus, which in one embodiment, is helper-dependent adenovirus, while in another embodiment, the virally-derived vector is derived from adenovirus-associated vector, as is described herein below.

In one embodiment, the term "vector" or "expression vector" refers to a carrier molecule into which a nucleic acid sequence can be inserted for introduction into a cell where it can be replicated. In one embodiment, the nucleic acid molecules are transcribed into RNA, which in some cases are then translated into a protein, polypeptide, or peptide. In other cases, RNA sequences are not translated, for example, in the production of antisense molecules or ribozymes. In one embodiment, expression vectors can contain a variety of "control sequences" which refer to nucleic acid sequences necessary for the transcription and possibly translation of an operably linked coding sequence in a particular host cell. In another embodiment, a vector further includes an origin of replication. As used herein, the term "control sequence" may also be referred to herein as a "regulatory sequence". In one embodiment the vector may be a shuttle vector, which in one embodiment can propagate both in prokaryotic and eukaryotic cells, or in another embodiment, the vector may be constructed to facilitate its integration within the genome of an organism of choice. The vector, in other embodiments may be, for example, a plasmid, a bacmid, a phagemid, a cosmid, a phage, a virus or an artificial chromosome. In one embodiment, the vector is a viral vector, which in one embodiment may be a bacteriophage, mammalian virus, or plant virus.

In one embodiment, the viral vector is an adenoviral vector. In another embodiment, the adenovirus may be of any known serotype or subgroup.

Advantages of using an adenoviral vector as a gene transfer vector are: its mid-sized genome, ease of manipulation, high titer, wide target-cell range and high infectivity. Both ends of the adenoviral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation.

In another embodiment, the adenoviral vector is a helper-dependent adenoviral vector ("HDAD", "HD" or "HDAd" or "HD-Ad"), which in another embodiment, is synonymous with gutless, gutted, mini, fully deleted, high-capacity, Δ, or pseudo adenovirus, and which in another embodiment are deleted of all viral coding sequences except for sequences supporting DNA replication, which in one embodiment, comprise the adenovirus inverted terminal repeats and packaging sequence (ψ). In another embodiment, helper-dependent adenoviruses express no viral proteins. In one embodiment, a helper-dependent adenoviral vector comprises only the cis-acting elements of the adenovirus required to replicate and package the vector DNA. In one embodiment, a helper-dependent adenoviral vector comprises approximately 500 bp of wild-type adenovirus sequence. In another embodiment, the adenoviral vector additionally comprises stuffer DNA to meet the minimum requirement for a genome size of 27.7 kb, which in one embodiment is required for efficient packaging into the adenovirus capsid. In one embodiment, non-coding mammalian DNA, with minimal repeat sequences, is used as stuffer DNA. In another embodiment, stuffer DNA comprises non-mammalian DNA, which in one embodiment, is HPRT and/or C346 cosmid sequences. In one embodiment, the HDAd vector is a non-replicating vector.

In one embodiment, helper-dependent adenoviruses display high-efficiency in vivo transduction, high-level transgene expression, are able to maintain long-term transgene expression, in one embodiment, by avoiding chronic toxicity due to residual expression of viral proteins, or a combination thereof. In another embodiment, helper-dependent adenoviruses have high titer production, efficient infection of a broad range of cell types, the ability to infect dividing and nondividing cells, or a combination thereof. In yet another embodiment, a helper-dependent adenovirus for use in the methods of the instant invention does not induce a strong adaptive immune response to an implanted micro-organ, which in one embodiment, is characterized by the generation of adeno-specific MHC class I restricted CD8 cytotoxic T lymphocytes (CTL) in immunocompetent hosts, which in one embodiment, would limit the duration of transgene expression and in another embodiment, would result in adenovirus vector clearance within several weeks. In still another embodiment, a helper-dependent adenovirus for use in the methods of the instant invention does not induce high cytotoxic T cell levels (as may be measured in one embodiment by positive CD8 staining, as is known in the art), and, in another embodiment, does not induce high helper T cell levels (as may be measured in one embodiment by positive CD4 stain, as is known in the art).

In another embodiment, helper-dependent adenoviruses have a lower risk of germ line transmission and insertional mutagenesis that may cause oncogenic transformation, because the vector genome does not integrate into the host cell chromosomes. In one embodiment, the cloning capacity of helper-dependent adenoviruses is very large (in one embodiment, approximately 37 kb, in another embodiment, approximately 36 kb), allowing for the delivery of whole genomic loci, multiple transgenes, and large cis-acting elements to enhance, prolong, and regulate transgene expression.

In one embodiment, the helper-dependent adenovirus system for use with the compositions and in the methods of the present invention is similar to that described in Palmer and Ng, 2003 (Mol Ther 8:846) and in Palmer and Ng, 2004 (Mol Ther 10:792), which are hereby incorporated herein by reference in their entirety. In one embodiment, there is a stuffer sequence inserted into the E3 region of the helper virus component of the helper-dependent adenovirus system to minimize recombination between the helper adenovirus and the helper-dependent adenovirus to produce replication competent adenovirus.

Figure 2:
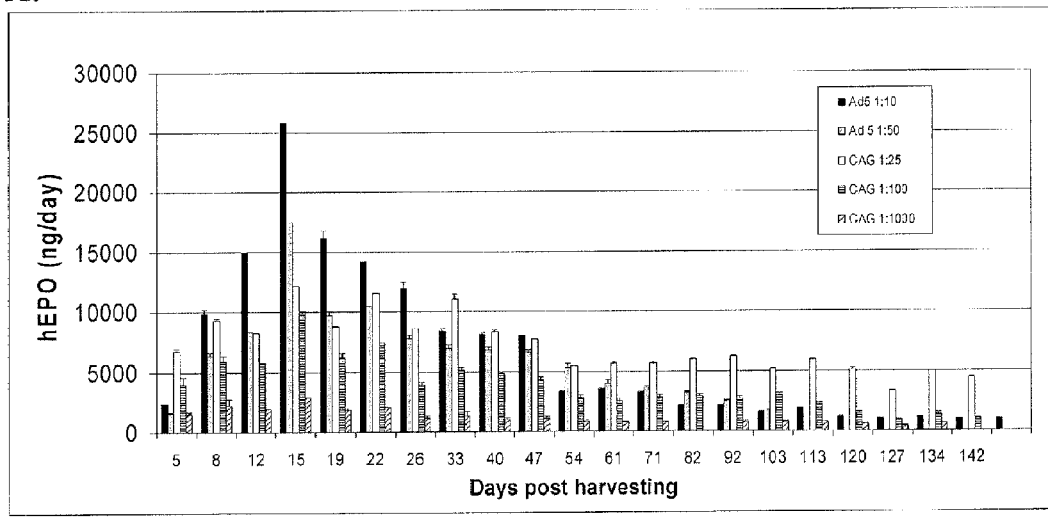
FIG. 2 presents levels of recombinant human erythropoietin (hEPO) produced in vitro by the formulations of the instant invention. HD-Ad-CAG-wt-hEPO GMMO titration (A). Micro-organs were transduced with increasing dilutions of HD-Ad-CAG-wt-hEPO virus: 1:25; 1:100; and 1:1000 dilutions. Ad5/CMV/wt-hEPO was diluted to a working concentration of 1:10 and 1:50. A comparison between GMMOs produced from two different skins, H-1 and H-2 (B). Micro-organs were transduced with HD-Ad-CAG-wt-hEPO 1:25. Bars indicate the hEPO concentration measured by ELISA in the culture media that was collected and replaced every 3-4 days.
Figure 2:
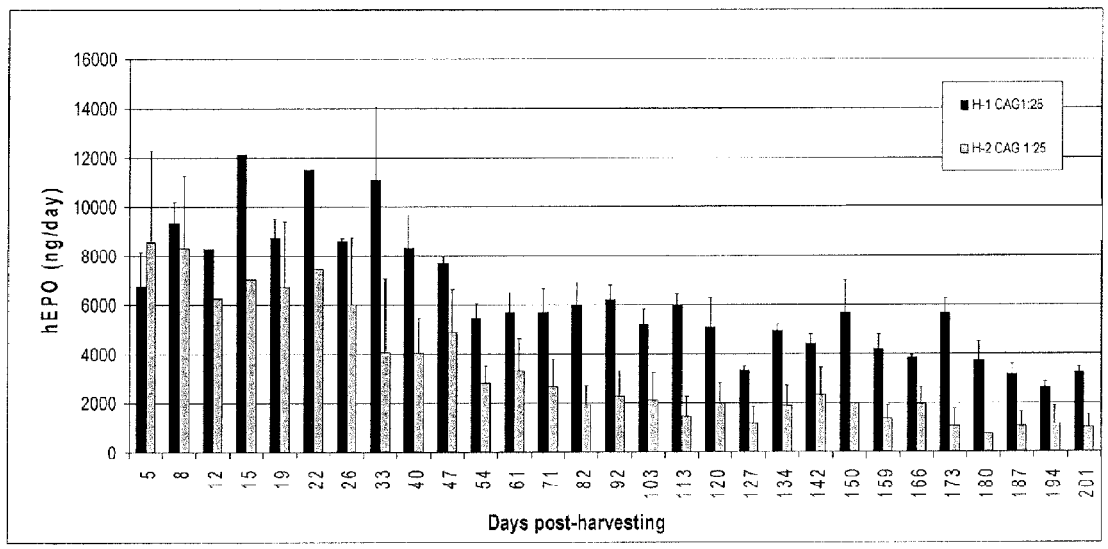
Figure 3:
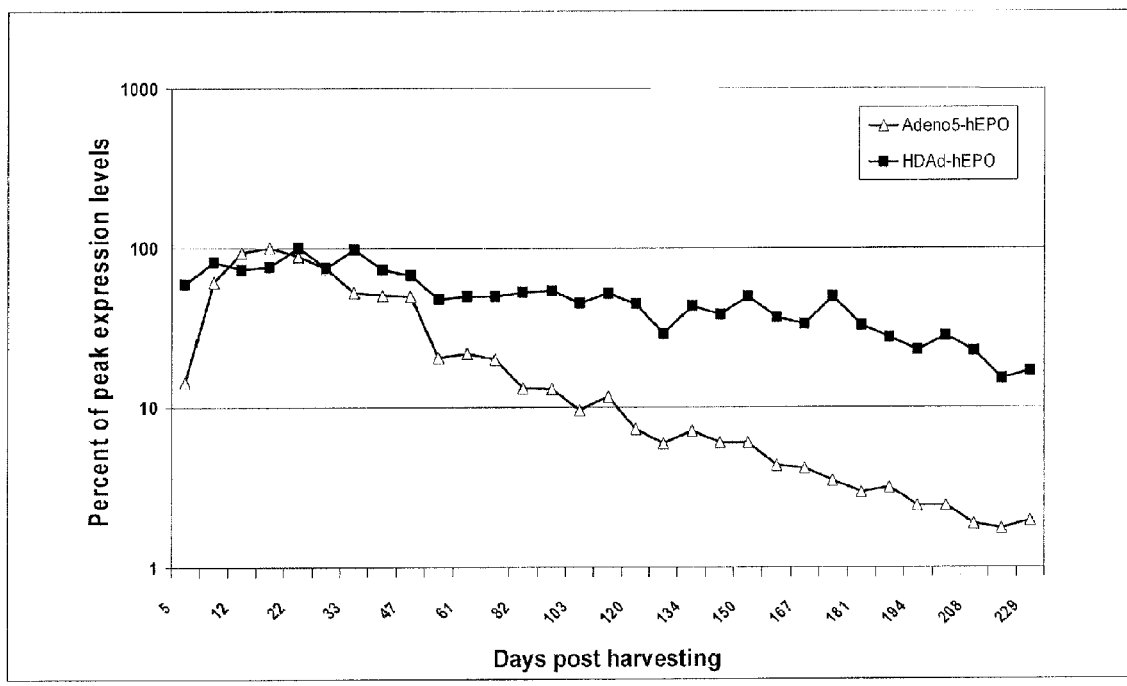
FIG. 3 presents the percent of peak erythropoietin (EPO) expression levels in vitro from optimized formulations comprising EPO-expressing gutless adenovirus and micro-organs comprising EPO-expressing adenovirus-5. Micro-organs were transduced with HD-Ad-CAG-hEPO at 1:25 or with Ad5/CMV/hEPO at 1:10.

In one embodiment, formulations of the instant invention comprising helper-dependent adenoviral vectors demonstrate long-term, high in vitro (FIGS. 1, 2, and 6B) and in vivo (FIG. 6A) expression levels of EPO and IFN-alpha. In another embodiment, formulations of the instant invention comprising helper-dependent adenoviral vectors demonstrate an increased percent of peak EPO expression levels for at least 100 days post-transduction compared to micro-organs comprising adenovirus-5 (FIG. 3). Without being bound by theory, one factor that may contribute to the long-lasting, high levels of gene product from micro-organs of the instant invention is use of a helper-dependent adenovirus vector, which is non-toxic to tissue and non-immunogenic within the formulations of the present invention.

Figure 16:
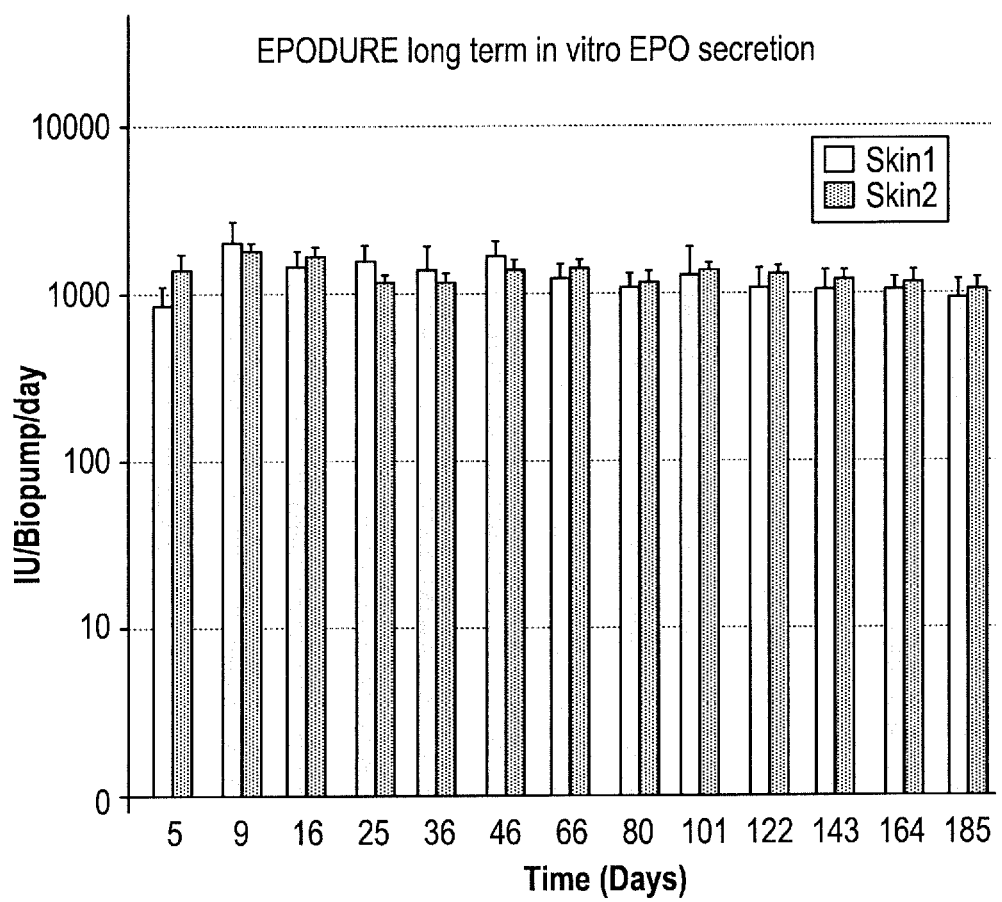
FIG. 16 presents hemoglobin and serum EPO levels following dose augmentation by a second administration.

In yet another embodiment, formulations of the instant invention comprising helper-dependent adenoviral vectors demonstrate an increased percent of peak EPO expression levels in vivo for less than one month (FIG. 16). In still another embodiment, in vivo peak EPO expression levels are increased for less than two weeks (FIG. 10C).

In another embodiment, the adenoviral vector is E1-deleted, while in another embodiment, the adenoviral vector additionally comprises deletions for E2, E3, E4, or a combination thereof.

In another embodiment, the viral vector is an adeno-associated viral vector (AAV). In one embodiment, AAV is a parvovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. At least nine serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter.

In one embodiment, the AAV DNA is approximately 4.7 kilobases long. In one embodiment, it contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, in one embodiment, the AAV can be used as a vector with all viral coding sequences removed and replaced by the cassette of genes for delivery.

In one embodiment, when using recombinant AAV (rAAV) as an expression vector, the vector comprises the 145-bp ITRs, which are only 6% of the AAV genome, which in one embodiment, leaves space in the vector to assemble a 4.5-kb DNA insertion.

In one embodiment, AAV is safe in that it is not considered pathogenic nor is it associated with any disease. The removal of viral coding sequences minimizes immune reactions to viral gene expression, and therefore, rAAV evokes only a minimal inflammatory response, if any. In another embodiment, AAV vector is double-stranded, while in another embodiment, AAV vector is self-complementary, which in one embodiment, bypasses the requirement of viral second-strand DNA synthesis, which in one embodiment, results in early transgene expression.

In another embodiment, the viral vector is a retroviral vector. The retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome.

In order to construct a retroviral vector in one embodiment, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed. When a recombinant plasmid containing a cDNA, together with the retroviral LTR and packaging sequences is introduced into this cell line (by calcium phosphate precipitation, for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. However, integration and stable expression require the division of host cells.

In other embodiments, the viral vector is derived from a virus such as vaccinia virus, lentivirus, polio virus, hepatitis virus, papilloma virus, cytomegalovirus, simian virus, or herpes simplex virus.

In certain embodiments of the invention, the vector comprising a nucleic acid sequence may comprise naked recombinant DNA or plasmids. Transfer of the construct may be performed by any method which physically or chemically permeabilizes the cell membrane. In one embodiment, the vector is a mini-circle DNA, which in one embodiment, is a supercoiled DNA molecule for non-viral gene transfer, which has neither a bacterial origin of replication nor an antibiotic resistance marker. In another embodiment, mini-circle DNA comprises no bacterial control regions from gene delivery vectors during the process of plasmid production. They are thus smaller and potentially safer than other plasmids used in gene therapy. In one embodiment, mini-circle DNA produce high yield, are simple to purify, and provide robust and persistent transgene expression.

Construction of vectors using standard recombinant techniques is well known in the art (see, for example, Maniatis, et al., Molecular Cloning, A Laboratory Manual (Cold Spring Harbor, 1990) and Ausubel, et al., 1994, Current Protocols in Molecular Biology (John Wiley & Sons, 1996), both incorporated herein by reference).

In another embodiment, a vector further comprises an insertion of a heterologous nucleic acid sequence encoding a marker polypeptide. The marker polypeptide may comprise, for example, yECitrine, green fluorescent protein (GFP), DS-Red (red fluorescent protein), secreted alkaline phosphatase (SEAP), β-galactosidase, chloramphenicol acetyl transferase, luciferase, GFP/EGFP, human growth hormone, or any number of other reporter proteins known to one skilled in the art.

In another embodiment, the vectors may comprise one or more genes of interest. Thus, in one embodiment, a vector of the instant invention may comprise a gene of interest, which in one embodiment, is erythropoietin or interferon alpha2b, which in one embodiment, expresses a marker, and in another embodiment, is linked in frame to a marker, which in one embodiment allows identification of the gene product of interest and in another embodiment, allows the distinction between a gene product of interest produced by a micro-organ and a similar gene product produced endogenously by host cells outside of the micro-organ(s).

In one embodiment, a vector comprising a nucleic acid encoding a therapeutic polypeptide of the instant invention is introduced into a micro-organ. There are a number of techniques known in the art for introducing cassettes and/or vectors into cells, for affecting the methods of the present invention, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation or liposome-mediated transfection, (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals).

In one embodiment, bombardment with nucleic acid coated particles may be a method for transferring a naked DNA expression construct into cells. This method depends on the ability to accelerate DNA-coated micro-projectiles to a high velocity allowing them to pierce cell membranes and enter cells without killing them. Several devices for accelerating small particles have been developed. One such device relies on a high voltage discharge to generate an electrical current, which in turn provides the motive force. The microprojectiles used have comprised biologically inert or biocompatible substances such as tungsten or gold beads. It is to be understood that any of these methods may be utilized for introduction of the desired sequences into cells, and cells thereby produced are to be considered as part of this invention, as is their use for effecting the methods of this invention.

In one embodiment, the vectors of the formulations and methods of the instant invention comprise a nucleic acid sequence. As used herein, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of RNA or DNA made from nucleotide analogs, and, as applicable to the embodiment being described, single (sense or antisense) and double-stranded polynucleotide. This term includes oligonucleotides composed of naturally occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the term "nucleic acid" or "oligonucleotide" refers to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The nucleic acids can be produced by any synthetic or recombinant process, which are well known in the art. Nucleic acids can further be modified to alter biophysical or biological properties by means of techniques known in the art. For example, the nucleic acid can be modified to increase its stability against nucleases (e.g., "end-capping"), or to modify its solubility, or binding affinity to complementary sequences. These nucleic acids may comprise the vector, the expression cassette, the promoter sequence, the gene of interest, or any combination thereof. In another embodiment, its lipophilicity may be modified, which, in turn, will reflect changes in the systems employed for its delivery, and in one embodiment, may further be influenced by whether such sequences are desired for retention within, or permeation through the skin, or any of its layers. Such considerations may influence any compound used in this invention, in the methods and systems described.

In one embodiment, DNA can be synthesized chemically from the four nucleotides in whole or in part by methods known in the art. Such methods include those described in Caruthers (1985; Science 230:281-285). DNA can also be synthesized by preparing overlapping double-stranded oligonucleotides, filling in the gaps, and ligating the ends together (see, generally, Sambrook et al. (1989; Molecular Cloning—A Laboratory Manual, 2nd Edition. Cold Spring Habour Laboratory Press, New York)). In another embodiment, inactivating mutations may be prepared from wild-type DNA by site-directed mutagenesis (see, for example, Zoller et al. (1982; DNA. 1984 December; 3(6):479-88); Zoller (1983); and Zoller (1984; DNA. 1984 December; 3(6):479-88); McPherson (1991; Directed Mutagenesis: A Practical Approach. Oxford University Press, NY)). The DNA obtained can be amplified by methods known in the art. One suitable method is the polymerase chain reaction (PCR) method described in Saiki et al. (1988; Science. 1988 Jan. 29; 239(4839):487-491), Mullis et al., U.S. Pat. No. 4,683,195, and Sambrook et al. (1989).

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. Variations in DNA sequences, which are caused by point mutations or by induced modifications (including insertion, deletion, and substitution) to enhance the activity, half-life or production of the polypeptides encoded thereby, are also encompassed in the invention.

The formulations of this invention may comprise nucleic acids, in one embodiment, or in another embodiment, the methods of this invention may include delivery of the same, wherein, in another embodiment, the nucleic acid is a part of a vector.

The efficacy of a particular expression vector system and method of introducing nucleic acid into a cell can be assessed by standard approaches routinely used in the art as described hereinbelow.

As will be appreciated by one skilled in the art, a fragment or derivative of a nucleic acid sequence or gene that encodes for a protein or peptide can still function in the same manner as the entire wild type gene or sequence. Likewise, forms of nucleic acid sequences can have variations as compared to wild type sequences, nevertheless encoding the protein or peptide of interest, or fragments thereof, retaining wild type function exhibiting the same biological effect, despite these variations. Each of these represents a separate embodiment of this present invention.

In one embodiment, the formulations and methods of the present invention may be used for gene silencing applications. In one embodiment, the activity or function of a particular gene is suppressed or diminished, via the use of antisense oligonucleotides, which are chimeric molecules, containing two or more chemically distinct regions, each made up of at least one nucleotide.

In one embodiment, chimeric oligonucleotides comprise at least one region wherein the oligonucleotide is modified so as to confer upon the oligonucleotide an increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids, which according to this aspect of the invention, serves as a means of gene silencing via degradation of specific sequences. Cleavage of the RNA target can be routinely detected by gel electrophoresis and, if necessary, associated nucleic acid hybridization techniques known in the art.

The chimeric antisense oligonucleotides may, in one embodiment, be formed as composite structures of two or more oligonucleotides and/or modified oligonucleotides, as is described in the art (see, for example, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922), and may, in another embodiment, comprise a ribozyme sequence.

Inhibition of gene expression, activity or function is effected, in another embodiment, via the use of small interfering RNAs, which provides sequence-specific inhibition of gene expression. Administration of double stranded/duplex RNA (dsRNA) corresponding to a single gene in an organism can silence expression of the specific gene by rapid degradation of the mRNA in affected cells. This process is referred to as gene silencing, with the dsRNA functioning as a specific RNA inhibitor (RNAi). RNAi may be derived from natural sources, such as in endogenous virus and transposon activity, or it can be artificially introduced into cells (Elbashir S M, et al (2001). Nature 411:494-498) via microinjection (Fire et al. (1998) Nature 391: 806-11), or by transformation with gene constructs generating complementary RNAs or fold-back RNA, or by other vectors (Waterhouse, P. M., et al. (1998). Proc. Natl. Acad. Sci. USA 95, 13959-13964 and Wang, Z., et al. (2000). J. Biol. Chem. 275, 40174-40179). The RNAi mediating mRNA degradation, in one embodiment, comprises duplex or double-stranded RNA, or, in other embodiments, include single-stranded RNA, isolated RNA (partially purified RNA, essentially pure RNA, synthetic RNA, recombinantly produced RNA), as well as altered RNA that differs from naturally occurring RNA by the addition, deletion and/or alteration of one or more nucleotides.

In one embodiment, the nucleic acid of the formulations and methods of the instant invention encode a therapeutic polypeptide. In one embodiment, the term "polypeptide" refers to a molecule comprised of amino acid residues joined by peptide (i.e., amide) bonds and includes peptides, polypeptides, and proteins. Hence, in one embodiment, the polypeptides of this invention may have single or multiple chains of covalently linked amino acids and may further contain intrachain or interchain linkages comprised of disulfide bonds. In one embodiment, some polypeptides may also form a subunit of a multiunit macromolecular complex. In one embodiment, the polypeptides can be expected to possess conformational preferences and to exhibit a three-dimensional structure. Both the conformational preferences and the three-dimensional structure will usually be defined by the polypeptide's primary (i.e., amino acid) sequence and/or the presence (or absence) of disulfide bonds or other covalent or non-covalent intrachain or interchain interactions.

In one embodiment, the term "peptide" refers to native peptides (either degradation products, synthetically synthesized peptides or recombinant peptides) and/or peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr. In addition to the above, the peptides of the present invention may also include one or more modified amino acids or one or more non-amino acid monomers (e.g. fatty acids, complex carbohydrates etc).

In one embodiment, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" may include both D- and L-amino acids.

As used herein, the term "amino acid" refers to either the D or L stereoisomer form of the amino acid, unless otherwise specifically designated. Also encompassed within the scope of this invention are equivalent proteins or equivalent peptides, e.g., having the biological activity of purified wild type tumor suppressor protein. "Equivalent proteins" and "equivalent polypeptides" refer to compounds that depart from the linear sequence of the naturally occurring proteins or polypeptides, but which have amino acid substitutions that do not change it's biologically activity. These equivalents can differ from the native sequences by the replacement of one or more amino acids with related amino acids, for example, similarly charged amino acids, or the substitution or modification of side chains or functional groups.

The peptides or polypeptides, or the DNA sequences encoding same, may be obtained from a variety of natural or unnatural sources, such as a prokaryotic or a eukaryotic cell. In one embodiment, the source cell may be wild type, recombinant, or mutant. In another embodiment, the plurality of peptides or polypeptides may be endogenous to microorganisms, such as bacteria, yeast, or fungi, to a virus, to an animal (including mammals, invertebrates, reptiles, birds, and insects) or to a plant cell.

In another embodiment, the peptides or polypeptides may be obtained from more specific sources, such as the surface coat of a virion particle, a particular cell lysate, a tissue extract, or they may be restricted to those polypeptides that are expressed on the surface of a cell membrane.

In another embodiment, the peptide or polypeptide is derived from a particular cell or tissue type, developmental stage or disease condition or stage. In one embodiment, the disease condition or stage is cancer, in another embodiment, the disease condition is an infection, which in another embodiment, is an HIV infection. In another embodiment, the disease condition is a developmental disorder, while in another embodiment, the disease condition is a metabolic disorder.

The polypeptide of the present invention can be of any size. As can be expected, the polypeptides can exhibit a wide variety of molecular weights, some exceeding 150 to 200 kilodaltons (kD). Typically, the polypeptides may have a molecular weight ranging from about 5,000 to about 100,000 daltons. Still others may fall in a narrower range, for example, about 10,000 to about 75,000 daltons, or about 20,000 to about 50,000 daltons. In an alternative embodiment, the polypeptides of the present invention may be 1-250 amino acid residues long. In another embodiment, the polypeptides of the present invention may be 10-200 amino acid residues long. In an alternative embodiment, the polypeptides of the present invention may be 50-100 amino acid residues long. In an alternative embodiment, the polypeptides of the present invention may be 1-250 amino acid residues long. In an alternative embodiment, the polypeptides of the present invention may be 1-250 amino acid residues long. In one embodiment, the maximum size of the peptide or polypeptide is determined by the vector from which it is expressed, which in one embodiment, is approximately between 20 and 37 kD, between 20 and 25 kD, between 25 and 30 kD, between 30 and 37 kD, or between 35 and 37 kD. In another embodiment, the polypeptide is a 34 kD glycoprotein.

In another embodiment, the peptides or polypeptides are agonists. In another embodiment, the peptides or polypeptides are antagonists. In another embodiment, the peptides or polypeptides are antigens. In another embodiment, the peptides or polypeptides are enzymes. In another embodiment, the peptides or polypeptides are activators of enzymes or other substrates. In another embodiment, the peptides or polypeptides are inhibitors of enzymes or other substrates. In another embodiment, the peptides or polypeptides are hormones. In another embodiment, the peptides or polypeptides are regulatory proteins. Regulatory proteins command the numerous interactions that govern the expression and replication of genes, the performance of enzymes, the interplay between cells and their environment, and many other manifestations. In another embodiment, the peptides or polypeptides are cytoskeletal proteins. Cytoskeletal proteins form a flexible framework for the cell, provide attachment points for organelles and formed bodies, and make communication between parts of the cell possible. In another embodiment, the peptides or polypeptides are toxins. In another embodiment, the therapeutic nucleic acids of the present invention encode one or more suicide genes.

In another embodiment, the peptides or polypeptides are functional fragments of agonists, antagonists, antigens, enzymes, enzyme activators, enzyme inhibitors, enzyme substrates, hormones, regulatory proteins, cytoskeletal proteins, or toxins. "Functional fragments" are meant to indicate a portion of the peptide or polypeptide which is capable of performing one or more of the functions of the peptide or polypeptide, even in the absence of the remainder of the peptide or polypeptide. In one embodiment, the functional fragment is sufficient to mediate an intermolecular interaction with a target of interest.

In an alternative embodiment, the peptide binds DNA or RNA or a fragment thereof. In one embodiment, the DNA or RNA binding peptide may be any of the many known in the art including, but not limited to Zinc finger proteins such as Beta-beta-alpha zinc finger proteins, Nuclear receptor proteins, Loop-sheet-helix type protein, and GAL4 type protein; the Helix-turn-helix proteins such as Cro and repressor proteins, LacI purine repressor proteins (PurR), Fold restriction endonuclease (DNA-recognition region), Gamma-delta recombinase protein (C-terminal domain), Hin recombinase protein, Trp repressor protein, Diptheria tox repressor, Catabolite gene activator proteins (CAP), Homeodomain proteins, RAP1 protein, Prd paired protein, Tc3 transposase protein, TFIIB family, Interferon regulatory factor, Transcription factor family, and ETS domain family bacteriophage; and the Leucine zipper proteins such as Basic zipper proteins and Zipper-type proteins (helix-loop-helix). In another embodiment, the DNA or RNA binding peptide may be other alpha-helix proteins such as Cre recombinase family, Papillomavirus-1 E2 protein, Histone family, Ebna1 nuclear protein family, Skn-1 transcription factor, High mobility group family, and MADS box family; Beta-sheet proteins such as TATA Box-Binding Proteins; Beta-hairpin/ribbon proteins such as Met repressor protein, Tus replication terminator protein, Integration host factor protein, Hyperthermophile DNA binding protein, Arc repressor, Transcription factor T domain; and other protein families such as Rel homology region proteins and Stat family. In another embodiment, the DNA or RNA binding peptide may be enzymes such as Methyl transferase proteins, PvuII Endonuclease protein, Endonuclease V protein, EcoRV Endonuclease family, BamHI Endonuclease family, EcoRI endonuclease family, DNA mismatch endonuclease, DNA polymerase I protein, DNA polymerase T7, Dnase I proteins, DNA polymerase beta proteins, Uraci-DNA glycosylase, Methyladenine-DNA glycosylase, Homing endonuclease, and Topoisomerase I or viral proteins such as HIV reverse transcriptase.

In another embodiment, the peptide or polypeptide is a transcriptional or translational activator or a fragment thereof. In another embodiment, the peptide or polypeptide is a transcriptional or translational repressor or a fragment thereof. In another embodiment, the peptide or polypeptide is a receptor or a fragment thereof.

In one embodiment, the peptide or polypeptide may represent a cognate peptide of any of the peptides or polypeptides described hereinabove. A "cognate" peptide is any peptide that interacts and/or binds to another molecule.

According to other embodiments of the present invention, recombinant gene products may be encoded by a polynucleotide having a modified nucleotide sequence, as compared to a corresponding natural polynucleotide.

In addition to proteins, recombinant gene products may also comprise functional RNA molecules.

According to another embodiment of the present invention, the formulations and methods of the present invention may provide a micro-organ producing functional RNA molecules.

Functional RNA molecules may comprise antisense oligonucleotide sequences, ribozymes comprising the antisense oligonucleotide described herein and a ribozyme sequence fused thereto. Such a ribozyme is readily synthesizable using solid phase oligonucleotide synthesis.

Ribozymes are being increasingly used for the sequence-specific inhibition of gene expression by the cleavage of mRNAs encoding proteins of interest [Welch et al., "Expression of ribozymes in gene transfer systems to modulate target RNA levels." Curr Opin Biotechnol. 1998 October; 9(5):486-96]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., "Ribozyme gene therapy for hepatitis C virus infection." Clin Diagn Virol. Jul. 15, 1998; 10(2-3):163-71. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms has demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays.

As described hereinabove, in one embodiment, the formulations and methods of the present invention provide a therapeutic formulation comprising a nucleic acid sequence encoding a therapeutic polypeptide. In one embodiment, the term "therapeutic" refers to a molecule, which when provided to a subject in need, provides a beneficial effect. In some cases, the molecule is therapeutic in that it functions to replace an absence or diminished presence of such a molecule in a subject. In one embodiment, the therapeutic protein is that of a protein which is absent in a subject, such as in cases of subjects with an endogenous null or mis-sense mutation of a required protein. In other embodiments, the endogenous protein is mutated, and produces a non-functional protein, compensated for by the provision of the functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In one embodiment, the term "therapeutic formulation" describes a substance applicable for use in the diagnosis, or in another embodiment, cure, or in another embodiment, mitigation, or in another embodiment, treatment, or in another embodiment, prevention of a disease, disorder, condition or infection. In one embodiment, the "therapeutic formulation" of this invention refers to any substance which affect the structure or function of the target to which it is applied.

In another embodiment, the "therapeutic formulation" of the present invention is a molecule that alleviates a symptom of a disease or disorder when administered to a subject afflicted thereof. In one embodiment, the "therapeutic formulation" of this invention is a synthetic molecule, or in another embodiment, a naturally occurring compound isolated from a source found in nature.

In one embodiment, the therapeutic polypeptide is erythropoietin. In one embodiment, the beneficial effect provided by erythropoietin is increased Hb levels. In one embodiment, the beneficial effect provided by erythropoietin is treatment of anemia.

In another embodiment, the therapeutic polypeptide is interferon alpha, which in one embodiment, is interferon alpha 2b. In one embodiment, said therapeutic polypeptide is any other therapeutic polypeptide.

In one embodiment, "treatment" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of a particular disease, while in one embodiment; "secondary" refers to a symptom that is derived from or consequent to a primary cause. In one embodiment, the compounds for use in the present invention treat primary or secondary symptoms or secondary complications related to the disease. In another embodiment, "symptoms" may be any manifestation of a disease or pathological condition.

In one embodiment, a therapeutic nucleic acid may encode a therapeutic polypeptide, which may in one embodiment, comprise an enzyme, an enzyme cofactor, a cytotoxic protein, an antibody, a channel protein, a transporter protein, a growth factor, a hormone, a cytokine, a receptor, a mucin, a surfactant, an aptamer or a hormone. In another embodiment, the therapeutic polypeptide may be of one or more of the categories as described above. In another embodiment, a therapeutic nucleic acid may encode functional RNA as described hereinbelow.

In one embodiment, the term "antibody or antibody fragment" refers to intact antibody molecules as well as functional fragments thereof, such as Fab, F(ab')2, and Fv that are capable of binding to an epitope. In one embodiment, an Fab fragment refers to the fragment which contains a monovalent antigen-binding fragment of an antibody molecule, which can be produced by digestion of whole antibody with the enzyme papain to yield an intact light chain and a portion of one heavy chain. In one embodiment, Fab' fragment refers to a part of an antibody molecule that can be obtained by treating whole antibody with pepsin, followed by reduction, to yield an intact light chain and a portion of the heavy chain. Two Fab' fragments may be obtained per antibody molecule. In one embodiment, $(Fab')_2$ refers to a fragment of an antibody that can be obtained by treating whole antibody with the enzyme pepsin without subsequent reduction. In another embodiment, F(ab')$_2$ is a dimer of two Fab' fragments held together by two disulfide bonds. In one embodiment, Fv, may refer to a genetically engineered fragment containing the variable region of the light chain and the variable region of the heavy chain expressed as two chains. In one embodiment, the antibody fragment may be a single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

In one embodiment, the antibody will recognize an epitope, which in another embodiment, refers to antigenic determinant on an antigen to which the paratope of an antibody binds. Epitopic determinants may, in other embodiments, consist of chemically active surface groupings of molecules such as amino acids or carbohydrate side chains and in other embodiments, may have specific three dimensional structural characteristics, and/or in other embodiments, have specific charge characteristics.

In one embodiment, the epitope recognized is from a pathogen, or in another embodiment, a pathogenic cell, or in another embodiment, a protein aberrantly expressed, which, in another embodiment, may refer to the location, quantity, or combination thereof of expression.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

In one embodiment, the antibody is tumoricidal, and is thereby therapeutic in certain cancers. Antibodies that possess tumoricidal activity are also known in the art, the use of any of which may represent an embodiment of this invention, including IMC-C225, EMD 72000, OvaRex Mab B43.13, anti-ganglioside G(D2) antibody ch14.18, C017-1A, trastuzumab, rhuMAb VEGF, sc-321, AF349, BAF349, AF743, BAF743, MAB743, AB1875, Anti-Flt-4AB3127, FLT41-A, rituximab, 2C3, CAMPATH 1H, 2G7, Alpha IR-3, ABX-EGF, MDX-447, anti-p75 IL-2R, anti-p64 IL-2R, and 2A11.

In one embodiment, the "therapeutic nucleic acid" of this invention may encode or the "therapeutic polypeptide" may be molecules that serve as antihypertensives, antidepressants, antianxiety agents, anticlotting agents, anticonvulsants, blood glucose-lowering agents, decongestants, antihistamines, antitussives, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, antibiotics, antiviral agents, anti-neoplastics, barbituates, sedatives, nutritional agents, beta blockers, emetics, anti-emetics, diuretics, anticoagulants, cardiotonics, androgens, corticoids, anabolic agents, growth hormone secretagogues, anti-infective agents, coronary vasodilators, carbonic anhydrase inhibitors, antiprotozoals, gastrointestinal agents, serotonin antagonists, anesthetics, hypoglycemic agents, dopaminergic agents, anti-Alzheimer's Disease agents, anti-ulcer agents, platelet inhibitors and glycogen phosphorylase inhibitors.

In one embodiment, the "therapeutic formulation" of this invention is antibacterial, antiviral, antifungal or antiparasitic. In another embodiment, the therapeutic formulation has cytotoxic or anti-cancer activity. In another embodiment, the therapeutic formulation is immunostimulatory. In another embodiment, the therapeutic formulation inhibits inflammatory or immune responses.

In one embodiment, the therapeutic nucleic acids may encode or the therapeutic polypeptides may be cytokines, such as interferons or interleukins, or their receptors. Lack of expression of cytokines, or of the appropriate ones, has been implicated in susceptibility to diseases, and enhanced expression may lead to resistance to a number of infections. Expression patterns of cytokines may be altered to produce a beneficial effect, such as for example, a biasing of the immune response toward a Th1 type expression pattern, or a Th2 pattern in infection, or in autoimmune disease, wherein altered expression patterns may prove beneficial to the host.

In another embodiment, the therapeutic nucleic acid may encode or the therapeutic polypeptide may be an enzyme, such as one involved in glycogen storage or breakdown. In another embodiment, the therapeutic protein comprises a transporter, such as an ion transporter, for example CFTR, or a glucose transporter, or other transporters whose deficiency, or inappropriate expression, results in a variety of diseases.

In another embodiment, the therapeutic nucleic acid encodes or the therapeutic polypeptide is a tumor suppressor or pro-apoptotic compound, which alters progression of cancer-related events.

In another embodiment, the therapeutic nucleic acid of the present invention may encode or the therapeutic polypeptide may be an immunomodulating protein. In one embodiment, the immunomodulating protein comprises cytokines, chemokines, complement or components, such as interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, or complement components.

In another embodiment, a therapeutic nucleic acid of this invention may encode or a therapeutic polypeptide may be a growth factor, or tissue-promoting factor. In one embodiment, the therapeutic compound is a bone morphogenetic protein, or OP-1, OP-2, BMP-5, BMP-6, BMP-2, BMP-3, BMP-4, BMP-9, DPP, Vg-1, 60A, or Vgr-1. In another embodiment, the therapeutic nucleic acid encodes an RNA or peptide that facilitates nerve regeneration or repair, and may include NGF, or other growth factors. In another embodiment, the therapeutic polypeptide facilitates nerve regeneration or repair, and may include NGF, or other growth factors.

In another embodiment, the therapeutic nucleic acid may encode or the therapeutic polypeptide may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the α family, transforming growth factors of the β family, gastrins, secretins, cholecystokinins, somatostatins, serotonins, substance P, transcription factors or combinations thereof.

In another embodiment, the gene comprises a reporter gene. In one embodiment, the reporter gene encodes a fluorescent protein. In one embodiment, the fluorescent protein is yECitrine or a yellow fluorescent protein. In one embodiment, the fluorescent protein is the jellyfish green fluorescent protein, or a mutant or variant thereof. In another embodiment, the GMMOs specifically may comprise any gene other than a reporter gene or a gene encoding a reporter protein.

In another embodiment, the reporter gene confers drug resistance. In one embodiment, the reporter gene confers resistance to an antibiotic, such as, for example, ampicilin, kanamycin, tetracycline, or others, as will be appreciated by one skilled in the art. In another embodiment, the antibiotic resistance genes may include those conferring resistance to neomycin (neo), blasticidin, spectinomycin, erythromycin, phleomycin, Tn917, gentamycin, and bleomycin. An example of the neomycin resistance gene is the neomycin resistance gene of transposon Tn5 that encodes for neomycin phosphotransferase 11, which confers resistance to various antibiotics, including G418 and kanamycin. In another embodiment, the reporter is a chloramphenicol acetyl transferase gene (cat) and confers resistance to chloramphenicol.

In one embodiment, the formulations and methods of this invention are for prevention of, or therapeutic intervention of viral infection, or in another embodiment, bacterial, parasitic, or fungal infection, or a combination thereof.

According to this aspect of the invention, the formulations and methods of this invention are for prevention of, or therapeutic intervention in disease. In one embodiment, the disease for which the subject is thus treated may comprise, but is not limited to: muscular dystrophy, cancer, cardiovascular disease, hypertension, infection, renal disease, neurodegenerative disease, such as Alzheimer's disease, Parkinson's disease, Huntington's chorea, Creurtfeld-Jacob disease, autoimmune disease, such as lupus, rheumatoid arthritis, endocarditis, Graves' disease or ALD, respiratory disease such as asthma or cystic fibrosis, bone disease, such as osteoporosis, joint disease, liver disease, disease of the skin, such as psoriasis or eczema, ophthalmic disease, otolaryngeal disease, other neurological disease such as Turret syndrome, schizophrenia, depression, autism, or stoke, or metabolic disease such as a glycogen storage disease or diabetes. It is to be understood that any disease whereby expression of a particular protein, provision of a therapeutic protein, provision of a drug, inhibition of expression of a particular protein, etc., which can be accomplished via the formulations of this invention and according to the methods of this invention, is to be considered as part of this invention.

In one embodiment, the formulations and methods of the instant invention comprise a nucleic acid sequence operably linked to one or more regulatory sequences. In one embodiment, a nucleic acid molecule introduced into a cell of a micro-organ is in a form suitable for expression in the cell of the gene product encoded by the nucleic acid. Accordingly, in one embodiment, the nucleic acid molecule includes coding and regulatory sequences required for transcription of a gene (or portion thereof). When the gene product is a protein or peptide, the nucleic acid molecule includes coding and regulatory sequences required for translation of the nucleic acid molecule include promoters, enhancers, polyadenylation signals, sequences necessary for transport of an encoded protein or peptide, for example N-terminal signal sequences for transport of proteins or peptides to the surface of the cell or secretion, in one embodiment.

Nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements which are known in the art include upstream regions from the dystrophin gene (Klamut et al., (1989) *Mol. Cell. Biol.* 9:2396), the creatine kinase gene (Buskin and Hauschka, (1989) *Mol. Cell. Biol.* 9:2627) and the troponin gene (Mar and Ordahl, (1988) *Proc. Natl. Acad. Sci. USA.* 85:6404). Negative response elements in keratin genes mediate transcriptional repression (Jho Sh et al, (2001). J. Biol Chem). Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters). Alternatively, a regulatory element which can direct constitutive expression of a gene in a variety of different cell types, such as a viral regulatory element, can be used. Examples of viral promoters commonly used to drive gene expression include those derived from polyoma virus, Adenovirus 2, cytomegalovirus (CMV) and Simian Virus 40, and retroviral LTRs. Alternatively, a regulatory element which provides inducible expression of a gene linked thereto can be used. The use of an inducible regulatory element (e.g., an inducible promoter) allows for modulation of the production of the gene product in the cell. Examples of potentially useful inducible regulatory systems for use in eukaryotic cells include hormone-regulated elements (e.g., see Mader, S, and White, J. H. (1993) *Proc. Natl. Acad. Sci. USA* 90:5603-5607), synthetic ligand-regulated elements (see, e.g., Spencer, D. M. et al 1993) *Science* 262:1019-1024) and ionizing radiation-regulated elements (e.g., see Manome, Y. Et al. (1993) *Biochemistry* 32:10607-10613; Datta, R. et al. (1992) *Proc. Natl. Acad. Sci. USA* 89:1014-10153). Additional tissue-specific or inducible regulatory systems which may be developed can also be used in accordance with the invention.

In one embodiment, a regulatory sequence of the instant invention may comprise a CMV promoter, while in another embodiment; the regulatory sequence may comprise a CAG promoter. In one embodiment, a CAG promoter is a composite promoter that combines the human cytomegalovirus immediate-early enhancer and a modified chicken beta-actin promoter and first intron. In one embodiment, a regulatory sequence may comprise a simian virus (SV)-40 polyadenylation sequence, which in one embodiment, is the mechanism by which most messenger RNA molecules are terminated at their 3' ends in eukaryotes. In one embodiment, the polyadenosine (poly-A) tail protects the mRNA molecule from exonucleases and is important for transcription termination, for export of the mRNA from the nucleus, and for translation. In another embodiment, a formulation of the present invention may comprise one or more regulatory sequences. In one embodiment, a regulatory sequence of this invention comprises SEQ ID No. 12. In another embodiment, a regulatory sequence of this invention comprises SEQ ID No. 13.

In one embodiment, formulations of the instant invention comprising CMV or CAG promoters in conjunction with SV40 polyadenylation sequence demonstrate long-term, high in vitro (FIGS. 1, 5, and 6B) and in vivo (FIG. 6A) expression levels of EPO and IFN-alpha. Without being bound by theory, one factor that may contribute to the long-lasting, high levels of gene product from micro-organs of the instant invention is the use of CMV, or alternatively, CAG as a promoter, which may be especially effective in micro-organ explants in promoting constitutive gene expression.

In one embodiment, the term "promoter" refers to a DNA sequence, which, in one embodiment, is directly upstream of the coding sequence and is important for basal and/or regulated transcription of a gene. In one embodiment, a promoter of the present invention is operatively linked to a gene of interest. In another embodiment, the promoter is a mutant of the endogenous promoter, which is normally associated with expression of the gene of interest, under the appropriate conditions.

In one embodiment, a promoter of the compositions and for use in the methods of the present invention is a regulatable promoter. In another embodiment, a regulatable promoter refers to a promoter whereby expression of a gene downstream occurs as a function of the occurrence or provision of specific conditions which stimulate expression from the particular promoter. In some embodiments, such conditions result in directly turning on expression, or in other embodiments, remove impediments to expression. In some embodiments, such conditions result in turning off, or reducing expression.

In one embodiment, such conditions may comprise specific temperatures, nutrients, absence of nutrients, presence of metals, or other stimuli or environmental factors as will be known to one skilled in the art. In one embodiment, a regulatable promoter may be regulated by galactose (e.g. UDP-galactose epimerase (GAL10), galactokinase (GAL1)), glucose (e.g. alcohol dehydrogenase II (ADH2)), or phosphate (e.g. acid phosphatase (PHO5)). In another embodiment, a regulatable promoter may be activated by heat shock (heat shock promoter) or chemicals such as IPTG or Tetracycline, or others, as will be known to one skilled in the art. It is to be understood that any regulatable promoter and conditions for such regulation is encompassed by the vectors, nucleic acids and methods of this invention, and represents an embodiment thereof.

In one embodiment, the formulations and methods of the instant invention increase the levels of a therapeutic polypeptide or nucleic acid by at least 5% over basal levels. In another embodiment, the levels of a therapeutic polypeptide or nucleic acid are increased by at least 7%, in another embodiment, by at least 10%, in another embodiment, by at least 15%, in another embodiment, by at least 20%, in another embodiment, by at least 25%, in another embodiment, by at least 30%, in another embodiment, by at least 40%, in another embodiment, by at least 50%, in another embodiment, by at least 60%, in another embodiment, by at least 75%, in another embodiment, by at least 100%, in another embodiment, by at least 125%, in another embodiment, by at least 150% over basal levels, in another embodiment, by at least 200% over basal levels. In still another embodiment, the formulations and methods of the instant invention increase the level of a therapeutic polypeptide or nucleic acid upon administration, wherein the level of the therapeutic polypeptide or nucleic acid then returns to basal or near basal levels. In one embodiment, the return to basal or near basal levels occurs within one month of administration of the therapeutic peptide or nucleic acid.

In one embodiment, expression of a therapeutic polypeptide or nucleic acid via the formulation of the present invention is increased compared to "basal levels", which in one embodiment, are levels of the gene expressed in hosts or cell culture that had not been administered or otherwise contacted with the therapeutic formulation of the present invention.

In another embodiment, the formulations and methods of the instant invention increase the levels of a therapeutic polypeptide or nucleic acid to approximately 2000 ng/day, or in another embodiment, 1500 ng/day, or in another embodiment, 1000 ng/day, or in another embodiment, 750 ng/day, or in another embodiment, 500 ng/day, or in another embodiment, 250 ng/day, or in another embodiment, 150 ng/day, or in another embodiment, 100 ng/day, or in another embodiment, 75 ng/day, or in another embodiment, 50 ng/day, or in another embodiment, 25 ng/day. In another embodiment, he formulations and methods of the instant invention increase the levels of a therapeutic polypeptide to between 20-70 mU/mL, or in another embodiment, 50-100 mU/mL, or in another embodiment, 5-20 mU/mL, or in another embodiment, 100-200 mU/mL, or in another embodiment, 10-70 mU/mL, or in another embodiment, 5-80 mU/mL. In another embodiment, the formulations and methods of the instant invention increase the levels of a therapeutic polypeptide to between 500-1000 mU/mL, or in another embodiment, 250-750 mU/mL, or in another embodiment, 500-5000 mU/mL.

In one embodiment, the formulations and methods of the instant invention increase the levels of a functional marker, which in one embodiment, is hematocrit levels, by at least 5% over basal levels. In another embodiment, the levels of the functional marker are increased by at least 7%, in another embodiment, by at least 10%, in another embodiment, by at least 15%, in another embodiment, by at least 20%, in another embodiment, by at least 25%, in another embodiment, by at least 30%, in another embodiment, by at least 40%, in another embodiment, by at least 50%, in another embodiment, by at least 60%, in another embodiment, by at least 75%, in another embodiment, by at least 100%, in another embodiment, by at least 125%, in another embodiment, by at least 150% over basal levels, in another embodiment, by at least 200% over basal levels.

In one embodiment, the therapeutic formulation of the present invention is "long-lasting", which in one embodiment refers to a formulation that can increase secretion, expression, production, circulation or persistence of a therapeutic polypeptide or nucleic acid In one embodiment, expression levels of a therapeutic polypeptide or nucleic acid are increased over basal levels for at least one month, or in another embodiment, for at least six months. In one embodiment, the increase is for 90% of the month. In another embodiment, the increase is for 90% of six months. In yet another embodiment, the increase is for 90% of any time period measured. In still another embodiment, the increase is for 80% of the time period measured. In a further embodiment, the increase is for 70% of the time period measured. In another embodiment, the increase is for 60% of the time period measured. In a yet another embodiment, the increase is for 50% of the time period measured.

In another embodiment, the therapeutic formulation of the present invention is "long-lasting", which in one embodiment refers to a formulation that can increase secretion, expression, production, circulation or persistence of a target molecule of the therapeutic polypeptide or nucleic acid. For instance, a target molecule may be a polypeptide, an RNA, a glycoprotein, a peptide, a glycosaminoglycan, protein-RNA complex, a DNA, or any downstream molecule synthesized by a cell, or any combination thereof. For example, when the therapeutic polypeptide is erythropoietin, a target molecule may be Hb. Accordingly, in one embodiment, a long-lasting formulation of the present invention may increase production, circulation or persistence of Hb in a subject.

In one embodiment, increase of a target molecule over basal levels is for at least one month, or in another embodiment, for at least six months. In one embodiment, the increase is for 90% of the month. In another embodiment, the increase is for 90% of six months. In yet another embodiment, the increase is for 90% of any time period measured. In still another embodiment, the increase is for 80% of the time period measured, e.g., one month, six months or a year. In a further embodiment, the increase is for 70% of the time period measured, e.g., one month, six months or a year. In another embodiment, the increase is for 60% of the time period measured, e.g., one month, six month or a year. In a yet another embodiment, the increase is for 50% of the time period measured, e.g., one month, six months or a year.

In yet another embodiment of the invention, the therapeutic formulation of the present invention is "long-lasting", which refers to a formulation that can increase secretion, expression, production, circulation or persistence of a functional marker. In one embodiment, the functional marker is hematocrit. In another embodiment, the functional marker is Hb. In yet another embodiment, the levels of a functional marker, for example hematocrit or Hb, are increased for at least 2 weeks, in another embodiment, for at least 3 weeks, in another embodiment, for at least 4 weeks, in another embodiment, for at least 5 weeks, in another embodiment, for at least 6 weeks, in another embodiment, for at least 8 weeks, in another embodiment, for at least 2 months, in another embodiment, for at least 2 months in another embodiment, for at least 2 months in another embodiment, for at least 3 months in another embodiment, for at least 4 months, in another embodiment, for at least 5 months, in another embodiment, for at least 7 months, in another embodiment, for at least 8 months, in another embodiment, for at least 9 months, in another embodiment, for at least 10 months, in another embodiment, for at least 11 months, or, in another embodiment, for at least 1 year. In another embodiment, expression levels of a therapeutic polypeptide or nucleic acid are increased for at least 4-6 months.

In one embodiment, increase of the functional marker, e.g., Hb, over basal levels is reflected in 90% of measurements made during any time period. In still another embodiment, the increase is reflected in 80% of the measurements made during any time period, e.g., one month, six months or a year. In a further embodiment, the increase is reflected in 70% of the measurements made during any time period, e.g., one month, six months or a year. In another embodiment, the increase is reflected in 60% of the measurements made during any time period, e.g., one month, six month or a year. In a yet another embodiment, the increase is reflected in 50% of the measurements made during any time period, e.g., one month, six months or a year.

In one embodiment, the nucleic acid sequence encoding a therapeutic polypeptide or nucleic acid is optimized for increased levels of therapeutic polypeptide or nucleic acid expression, or, in another embodiment, for increased duration of therapeutic polypeptide or nucleic acid expression, or, in another embodiment, a combination thereof.

In one embodiment, the term "optimized" refers to a desired change, which, in one embodiment, is a change in gene expression and, in another embodiment, in protein expression. In one embodiment, optimized gene expression is optimized regulation of gene expression. In another embodiment, optimized gene expression is an increase in gene expression. According to this aspect and in one embodiment, a 2-fold through 1000-fold increase in gene expression compared to wild-type is contemplated. In another embodiment, a 2-fold to 500-fold increase in gene expression, in another embodiment, a 2-fold to 100-fold increase in gene expression, in another embodiment, a 2-fold to 50-fold increase in gene expression, in another embodiment, a 2-fold to 20-fold increase in gene expression, in another embodiment, a 2-fold to 10-fold increase in gene expression, in another embodiment, a 3-fold to 5-fold increase in gene expression is contemplated.

In another embodiment, optimized gene expression may be an increase in gene expression under particular environmental conditions. In another embodiment, optimized gene expression may comprise a decrease in gene expression, which, in one embodiment, may be only under particular environmental conditions.

In another embodiment, optimized gene expression is an increased duration of gene expression. According to this aspect and in one embodiment, a 2-fold through 1000-fold increase in the duration of gene expression compared to wild-type is contemplated. In another embodiment, a 2-fold to 500-fold increase in the duration of gene expression, in another embodiment, a 2-fold to 100-fold increase in the duration of gene expression, in another embodiment, a 2-fold to 50-fold increase in the duration of gene expression, in another embodiment, a 2-fold to 20-fold increase in the duration of gene expression, in another embodiment, a 2-fold to 10-fold increase in the duration of gene expression, in another embodiment, a 3-fold to 5-fold increase in the duration of gene expression is contemplated. In another embodiment, the increased duration of gene expression is compared to gene expression in non-vector-expressing controls, or alternatively, compared to gene expression in wild-type-vector-expressing controls.

Expression in mammalian cells is hampered, in one embodiment, by transcriptional silencing, low mRNA half-life, alternative splicing events, premature polyadenylation, inefficient nuclear translocation and availability of rare tRNAs pools. The source of many problems in mammalian expressions is found within the message encoding the transgene including in the autologous expression of many crucial mammalian genes as well. The optimization of mammalian RNAs may include modification of cis acting elements, adaptation of its GC-content, modifying codon bias with respect to non-limiting tRNAs pools of the mammalian cell, avoiding internal homologous regions and excluding RNAi's.

Therefore, in one embodiment, when relying on carefully designed synthetic genes, stable messages with prolonged half-lives, constitutive nuclear export and high level protein production within the mammalian host can be expected.

Thus, in one embodiment, optimizing a gene entails adapting the codon usage to the codon bias of host genes, which in one embodiment, are *Homo sapiens* genes; adjusting regions of very high (>80%) or very low (<30%) GC content; avoiding one or more of the following cis-acting sequence motifs: internal TATA-boxes, chi-sites and ribosomal entry sites; AT-rich or GC-rich sequence stretches; ARE, INS, CRS sequence elements; repeat sequences and RNA secondary structures; (cryptic) splice donor and acceptor sites, branch points; or a combination thereof. In one embodiment, a gene is optimized for expression in homo sapien cells. In another embodiment, a gene is optimized for expression in micro-organs. In yet another embodiment, a gene is optimized for expression in dermal cells. In still another embodiment, optimizing a gene expression entails adding sequence elements to flanking regions of a gene and/or elsewhere in the expression vector. Sequence elements that may be added for optimizing gene expression include, for example, matrix-attached regions (MAR), specialized chromatin structures (SCS) and woodchuck hepatitis post-transcriptional regulatory elements (WPRE).

Figure 4:
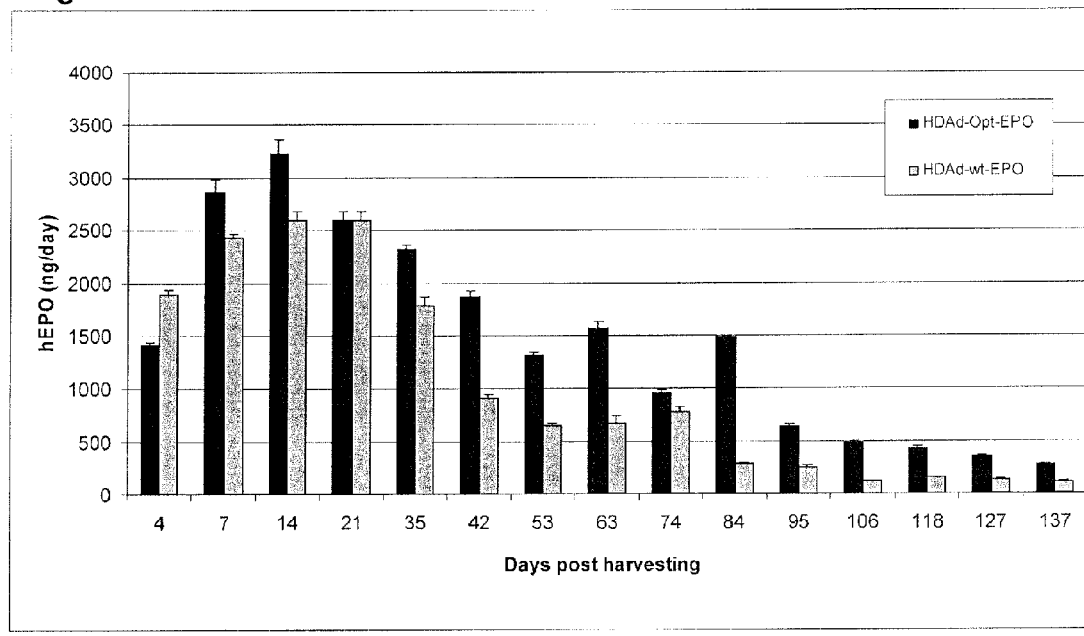
FIG. 4 presents erythropoietin (EPO) expression levels in vitro from formulations comprising optimized and non-optimized EPO-expressing gutless adenovirus. Micro-organs were transduced with a working dilution of 1:100 viral particles. Bars indicate the hEPO concentration measured by ELISA in the culture media that was collected and replaced every 3-4 days.

In one embodiment, as demonstrated herein, optimized genes, such as EPO, maintain an increase percent of peak expression levels for an extended period of time compared to both non-optimized EPO expressed from a gutless adenovirus vector or non-optimized EPO expressed from an adenovirus 5 vector (FIGS. 3 and 4).

In one embodiment, the term "gene" refers to a nucleic acid fragment that is capable of being expressed as a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

In one embodiment, the therapeutic nucleic acid may be any gene which encodes an RNA molecule (sense or antisense), peptide, polypeptide, glycoprotein, lipoprotein or combination thereof or to any other post modified polypeptide. In one embodiment of the invention, the gene of interest may be naturally expressed in the tissue sample. In another embodiment of this invention, the tissue sample may be genetically engineered so that at least one cell will express the gene of interest, which is either not naturally expressed by the cell or has an altered expression profile within the cell. In one embodiment, the therapeutic nucleic acid of the present invention may encode or the therapeutic polypeptide may be any of the proteins listed in U.S. patent application Ser. No. 10/376,506, which is incorporated herein by reference in its entirety.

In one embodiment, the genetically modified micro-organ is a genetically modified dermal micro-organ. "Dermal" micro-organs ("DMO") may comprise a plurality of dermis components, where in one embodiment; dermis is the portion of the skin located below the epidermis. These components may comprise skin fibroblast, epithelial cells, other cell types, bases of hair follicles, nerve endings, sweat and sebaceous glands, and blood and lymph vessels. In one embodiment, a dermal micro-organ may comprise fat tissue, wherein in another embodiment, a dermal micro-organ may not comprise fat tissue.

In some embodiments of the invention, the dermal micro-organ may contain tissue of a basal epidermal layer and, optionally, other epidermal layers of the skin. In other embodiments, the dermal micro-organ does not include basal layer tissue. In another embodiment of the invention, the dermal micro-organ does not include epidermal layers. In yet another embodiment, the dermal micro-organ contains an incomplete epidermal layer. In still another embodiment, the dermal micro-organ may contain a few layers of epidermal tissue. In still another embodiment, the dermal micro-organ may contain invaginations of the epidermis into the dermis. In a further embodiment, the dermal micro-organ may include additional components such as sweat glands and/or hair follicles.

In one embodiment of the invention, the DMO includes the entire cross-section of the dermis. In another embodiment of the invention, the dermal micro-organ includes part of the cross-section of the dermis. In a further embodiment, the DMO includes most of the cross section of the dermis, namely, most of the layers and components of the dermis including the papillary and reticular dermis. In a further embodiment, the DMO includes primarily dermal tissue, but may also include fat tissue. In some embodiments of the invention, the DMO does not produce keratin or produces a negligible amount of keratin, thereby preventing the formation of keratin cysts following implantation in a recipient, for example, following subcutaneous or intradermal implantation. Further details regarding dermal micro-organs, including methods of harvesting, maintaining in culture, and implanting said dermal micro-organs, are described in PCT Patent Application WO2004/099363, which is incorporated herein by reference in its entirety.

In another embodiment, the invention provides a method of providing a therapeutic polypeptide to a subject in need over a sustained period comprising providing one or more genetically modified micro-organs, said micro-organs comprising a vector comprising a nucleic acid sequence operably linked to one or more regulatory sequences; and implanting said genetically modified micro-organ in said subject, wherein said nucleic acid sequence encodes a therapeutic polypeptide and whereby the expression level of the therapeutic nucleic acid or polypeptide is increased by more than 5% over basal level and said increase is maintained for greater than one month. In another embodiment, the invention provides a method of providing a therapeutic polypeptide to a subject in need over a sustained period comprising providing one or more genetically modified micro-organs, said micro-organs comprising a vector comprising a nucleic acid sequence operably linked to one or more regulatory sequences; and implanting said genetically modified micro-organ in said subject, wherein said nucleic acid sequence encodes a therapeutic polypeptide and wherein said vector is a helper-dependent adenovirus vector. In another embodiment, the invention provides a method of providing a therapeutic polypeptide to a subject in need over a sustained period comprising providing one or more genetically modified micro-organs, said micro-organs comprising a vector comprising a nucleic acid sequence operably linked to one or more regulatory sequences; and implanting said genetically modified micro-organ in said subject, wherein said nucleic acid sequence encodes a therapeutic polypeptide and wherein said vector is a helper-dependent adenovirus vector.

In another embodiment, the methods described hereinabove provide a therapeutic nucleic acid to a subject in need wherein the expression level of the therapeutic nucleic acid or polypeptide is increased by more than 5% over basal level and said increase is maintained for greater than one hour, 3 hours, 6 hours, 9 hours, 12 hours, 18 hours, 1 day, or 2 days, wherein said vector is a helper-dependent adenovirus vector, or a combination thereof.

In one embodiment, this invention provides a therapeutic formulation as described hereinabove in which the therapeutic polypeptide is erythropoietin or wherein the therapeutic nucleic acid encodes erythropoietin. In another embodiment, this invention provides a long-lasting erythropoietin formulation comprising a genetically modified micro-organ, said micro-organ comprising a vector comprising a nucleic acid sequence operably linked to one or more regulatory sequences, wherein said nucleic acid sequence encodes erythropoietin and whereby said formulation increases erythropoietin levels by more than 5% over basal levels and said increased erythropoietin levels persist for greater than one month. In another embodiment, the formulation increases erythropoietin levels by more than 5% over basal levels and the increase erythropoietin levels persist for less than one month. In yet another embodiment, the invention provides a method of providing a therapeutic formulation to a subject in need in which the therapeutic polypeptide is erythropoietin or wherein the therapeutic nucleic acid encodes erythropoietin. In still another embodiment, the invention provides a method of providing erythropoietin to a subject in need.

In a further embodiment, this invention provides a method of delivering erythropoietin to a subject in need over a sustained period comprising: providing one or more genetically modified micro-organs, said micro-organs comprising a vector comprising a nucleic acid sequence operably linked to one or more regulatory sequences; and implanting said genetically modified micro-organ in said subject, wherein said nucleic acid sequence encodes erythropoietin and whereby erythropoietin levels are increased by more than 5% over basal levels and said increased erythropoietin levels persist for greater than one month. In another embodiment, the erythropoietin levels are increased by more than 5% over basal levels and the increased erythropoietin levels persist for less than one month.

In yet another embodiment, this invention provides a method of inducing formation of new blood cells in a subject in need over a sustained period comprising: providing one or more genetically modified micro-organs, said micro-organs comprising a vector comprising a nucleic acid sequence operably linked to one or more regulatory sequences; and implanting said genetically modified micro-organ in said subject, wherein said nucleic acid sequence encodes erythropoietin and whereby erythropoietin levels are increased by more than 5% over basal levels and said increased erythropoietin levels persist for greater than one month. In still another embodiment, the erythropoietin levels are increased by more than 5% over basal levels and the increased erythropoietin levels persist for less than one month.

Erythropoietin (EPO) is a glycoprotein hormone involved in the maturation of erythroid progenitor cells into erythrocytes. In one embodiment, erythropoietin is essential in regulating levels of red blood cells in circulation. Naturally occurring erythropoietin is produced by the kidneys and liver, circulates in the blood, and stimulates the production of red blood cells in bone marrow, in one embodiment, in response to hypoxia.

In one embodiment, EPO of the compositions and methods of the instant invention may comprise glycosylation patterns similar to those of EPO extracted from human or animal urine, or in another embodiment, plasma.

The identification, cloning, and expression of genes encoding erythropoietin are described in U.S. Pat. Nos. 5,756,349; 5,955,422; 5,618,698; 5,547,933; 5,621,080; 5,441,868; and 4,703,008, which are incorporated herein by reference. A description of the purification of recombinant erythropoietin from cell medium that supported the growth of mammalian cells containing recombinant erythropoietin plasmids for example, are included in U.S. Pat. No. 4,667,016 to Lai et al, which is incorporated herein by reference. Recombinant erythropoietin produced by genetic engineering techniques involving the expression of a protein product in vitro from a host cell transformed with the gene encoding erythropoietin has been used to treat anemia resulting from chronic renal failure.

EPO may be used in the treatment of anemia as a result of renal failure including chronic kidney disease (CKD) and end stage renal disease (ESRD); anemia associated with HIV infection in zidovudine (AZT) treated patients; anemia associated with cancer chemotherapy; microangiopathic haemolytic anemia that may be a secondary to mechanical valve haemolysis; anemia of prematurity; anemia as a result rheumatoid arthritis and other inflammatory conditions; and anemia associated with cancer including multiple myeloma and non-Hodgkin lymphoma. In addition, administration of EPO may benefit subjects prior to scheduled surgery, subjects suffering from hematopoietic stem cell disorders, subjects in need of acceleration of erythroid repopulation after bone marrow transplantation, or subjects in need of induction of fetal Hb synthesis as a result of sickle cell anemia and thalassemia.

Administration of rhu-EPO (recombinant human-EPO) has become routine in the treatment of anemia secondary to renal insufficiency, where doses of 50-150 u/kg given three times per week are used to gradually restore hematocrit and eliminate transfusion dependency. This results in an average daily dosage of 21.4-64.3 EPO U/Kg/day to a subject being treated.

Many cell surface and secretory proteins produced by eukaryotic cells are modified with one or more oligosaccharide groups called glycosylation, which can dramatically affect protein stability, secretion, and subcellular localization as well as biological activity. In one embodiment, both human urinary derived erythropoietin and recombinant erythropoietin (expressed in mammalian cells) having the amino acid sequence 1-165 of human erythropoietin comprise three N-linked and one O-linked oligosaccharide chains which together comprise about 40% of the total molecular weight of the glycoprotein. In one embodiment, non-glycosylated erythropoietin has greatly reduced in vivo activity compared to the glycosylated form but does retain some in vitro activity. In one embodiment, the EPO of the compositions and for use in the methods of the present invention are fully glycosylated, while in another embodiment, they are comprise some glycosylated residues, while in another embodiment, they are not glycosylated.

In one embodiment, the EPO gene may be a wild-type EPO gene, while in another embodiment, the EPO gene may be modified. In one embodiment, the modified EPO gene may be optimized.

In one embodiment, the EPO gene has a nucleic acid sequence that corresponds to that set forth in Genbank Accession Nos: X02158; AF202312; AF202311; AF202309; AF202310; AF053356; AF202306; AF202307; or AF202308 or encodes a protein sequence that corresponds to that set forth in Genbank Accession Nos: CAA26095; AAF23134; AAF17572; AAF23133; AAC78791; or AAF23132. In another embodiment, the EPO precursor gene has a nucleic acid sequence that corresponds to that set forth in Genbank Accession Nos: NM_000799; M11319; BC093628; or BC111937 or encodes a protein sequence that corresponds to that set forth in Genbank Accession Nos: NP_000790; AAA52400; AAH93628; or AAI11938. In another embodiment, the EPO gene has a nucleic acid sequence as presented in SEQ ID No: 7, while in another embodiment, the EPO gene has an amino acid sequence as presented in SEQ ID No: 10. In another embodiment, the EPO gene has a nucleic acid that is homologous to that presented in SEQ ID No: 7, while in another embodiment, the EPO gene has an amino acid sequence that is homologous to that presented in SEQ ID No: 10. In one embodiment, the nucleic acid encoding erythropoietin operably linked to one or more regulatory sequences has a nucleic acid sequence as presented in SEQ ID No: 11. In another embodiment, the nucleic acid encoding erythropoietin operably linked to one or more regulatory sequences has a nucleic acid sequence that is homologous to that presented in SEQ ID No: 11. In one embodiment, the vector used for genetic modification has a nucleic acid sequence as presented in SEQ ID No. 3. In another embodiment, the vector used for genetic modification has a nucleic acid sequence as presented in SEQ ID No. 4. In yet another embodiment, the vector used for genetic modification has a nucleic acid sequence homologous to that presented in SEQ ID No. 3. In still another embodiment, the vector used for genetic modification has a nucleic acid sequence homologous to that presented in SEQ ID No. 4.

In one embodiment, the formulations of the present invention may be used to treat a subject having anemia. In one embodiment, anemia is defined as "a pathologic deficiency in the amount of oxygen-carrying Hb in the red blood cells." Symptoms of anemia include fatigue, diminished ability to perform daily functions, impaired cognitive function, headache, dizziness, chest pain and shortness of breath, nausea, depression, pain, or a combination thereof. In one embodiment, anemia is associated with a poorer prognosis and increased mortality.

In one embodiment, administration of a GMMO-hEPO of this invention increases and/or maintains Hb to therapeutic levels. In some embodiments, administration of a GMMO-hEPO results in increased and/or maintained Hb for extended time periods. In certain instances, the measurable EPO levels during the time period of increased and/or maintained Hb levels do not show a comparable percent increase. In one embodiment, administration of a GMMO-hEPO of this invention increases and/or maintains hematocrit levels. In some embodiments, administration of a GMMO-hEPO results in increased and/or maintained hematocrit levels for extended time periods.

Anemia is often a consequence of renal failure due to decreased production of erythropoietin from the kidney. In another embodiment, anemia is caused by lowered red blood cell (erythroid) production by bone marrow due to cancer infiltration, lymphoma or leukemia including non-Hodgkin's lymphoma, multiple myeloma, chemotherapy, mechanical valve haemolysis, prematurity, rheumatoid arthritis, inflammatory conditions, hematopoietic disorders, sickle cell anemia, thalassemia or marrow replacement. Other causes of anemia comprise, blood loss due to excessive bleeding such as hemorrhages or abnormal menstrual bleeding; cancer therapies such as surgery, radiotherapy, chemotherapy e.g., treatment of AIDs patients with Zidovudine (AZT), immunotherapy, or a combination thereof; infiltration or replacement of cancerous bone marrow; increased hemolysis, which in one embodiment is breakdown or destruction of red blood cells; low levels of erythropoietin, or a combination thereof. In one embodiment, anemia refers to Fanconi anemia, which in one embodiment is an inherited anemia that leads to bone marrow failure (aplastic anemia) and often to acute myelogenous leukemia (AML). In another embodiment, anemia refers to Diamond Blackfan anemia, normocytic anemia, aplastic anemia, iron-deficiency anemia, vitamin deficiency anemia, Sideroblastic Anemia, Paroxysmal Nocturnal Hemoglobinuria, Anemia of Chronic Disease, Anemia in Kidney Disease and Dialysis, or a combination thereof.

In another embodiment, the long-lasting EPO formulation of the instant invention is used for treating a diabetic subject. According to this aspect and in one embodiment, the EPO formulation of the instant invention may be used in conjunction with other treatments for diabetes known in the Art, including, inter alia, insulin administration, oral hypoglycemic drugs, which in one embodiment are sulfonurea drugs, which in one embodiment including inter alia glucotrol, glyburide, glynase and amaryl; glucophage, thiazolidinediones including inter alia rezulin, actos and avandia; or a combination thereof. In another embodiment, the long-lasting EPO formulation of the instant invention is used for treating a subject suffering from chronic kidney disease, while in another embodiment, is used for treating a subject suffering from end-stage renal disease. In another embodiment, the formulations of the instant invention are used for subjects that are susceptible to the above-mentioned diseases or conditions.

In yet another embodiment, the long-lasting EPO formulation of the instant invention is used for increasing hemoglobin level in a subject. A subject in need of increased Hb, may for instance be a subject prior to major surgery.

It is to be understood that the formulations and methods of this invention may be used to treat anemia, regardless of the cause of anemia and whether or not the cause of anemia is known.

In one embodiment, the formulations and methods thereof provide an effective EPO therapy.

By the term "effective EPO therapy" it is meant a level of EPO sufficient to bring the Hb level in a patient within the therapeutic window. In one embodiment, "effective EPO therapy" refers to an increase in erythropoiesis in a subject in need. In one embodiment, "effective EPO therapy" refers to prevention of a decrease of erythropoiesis in a subject in need. As used herein, the term "effective EPO therapy" may also be referred to herein as an "effective dosage" or "effective dose" of erythropoietin.

In one embodiment of the invention, effective EPO therapy is achieved by implanting at least one (1) human EPO-GMMO (hEPO-GMMO) into a patient. In another embodiment, effective EPO therapy is achieved by implanting at least two (2) hEPO-GMMO into a patient. In one embodiment, effective EPO therapy is achieved by implanting at least three (3) hEPO-GMMO into a patient. In one embodiment, effective EPO therapy is achieved by implanting at least four (4) hEPO-GMMO into a patient. In one embodiment, effective EPO therapy is achieved by implanting at least five (5) hEPO-GMMO into a patient. In one embodiment, effective EPO therapy is achieved by implanting at least six (6) hEPO-GMMO into a patient. In one embodiment, effective EPO therapy is achieved by implanting greater than six (6) hEPO-GMMO into a patient.

As used herein, the term "therapeutic window" it is meant the desired level of Hb in a subject in need. In one embodiment, the therapeutic window refers to a Hb concentration within the range of 10 gm/dl to 12 gm/dl. In another embodiment, the therapeutic window refers to a Hb concentration within the range of 9-11 gm/dl. In yet another embodiment, the Hb concentration is within the range of 9.5-12.6 gm/dl. In still another embodiment, the Hb concentration is within the range of 9-13.2 gm/dl. In a further embodiment, the Hb concentration is within the range of 8.5-13.8 gm/dl. In another embodiment, the Hb concentration is within the range of 8-14.4 gm/dl. As used herein, the term "therapeutic window" may also be referred to as "physiological levels" or "physiological hemoglobin levels".

In one embodiment, the subject in need is human. In one embodiment, the subject in need is a renal patient. In another embodiment, the subject in need is suffering from end-stage renal disease. In yet another embodiment, the subject in need is suffering from chronic kidney disease (CKD). In still another embodiment, the subject is suffering from pre-dialysis CKD. In another embodiment, the subject in need is diabetic. In one embodiment, the subject is a pre-dialysis patient. In another embodiment, the subject is concurrently receiving dialysis. In yet another embodiment, the subject has received dialysis.

In one embodiment of the invention, an effective EPO therapy brings the Hb ("Hb") level in a patient within the therapeutic window. In another embodiment of the invention, an effective EPO therapy brings the Hb level in a patient within a range +/−10% of the therapeutic window. In another embodiment of the invention, an effective EPO therapy brings the Hb level in a patient within a range +/−20% of the therapeutic window. In yet another embodiment of the invention, an effective EPO therapy brings the Hb level in a patient within a range +/−30% of the therapeutic window. In still another embodiment, an effective EPO therapy brings the Hb level in a patient within a range +/−40% of the therapeutic window. In a further embodiment, an effective EPO therapy brings the Hb level in a patient within a range +/−50% of the therapeutic window.

In one embodiment, an increase of blood Hb levels above 11.5 g/dl for four consecutive weekly measurements, may be considered outside of the therapeutic window. In another embodiment, an increase of blood Hb levels above 12.0 g/dl for four consecutive weekly measurements, may be considered outside of the therapeutic window. In an effort to avoid an increase of blood Hb levels outside of the therapeutic window, methods of implantation of a long-lasting erythropoietin formulation may be directed to avoid a resultant elevation of serum EPO above the upper limit of the normal physiological range, defined as a level exceeding 200 mU/ml.

As used herein, the terms "effective dosage" or "effective dose" refers to the effective amount of a therapeutic polypeptide expressed from an at least one GMMO per day.

As used herein, units for EPO are the accepted International units and are referred to herein using the symbol "U" or "IU".

In one embodiment, dosage for an effective EPO therapy is between 18-150 IU/kg bodyweight of a patient/day. In another embodiment, effective EPO therapy is between 12-150 U/kg bodyweight of a patient/day. In one embodiment, dosage for an effective EPO therapy is between 20-40 IU/kg bodyweight of a patient/day. In one embodiment, dosage for an effective EPO therapy is between 40-60 IU/kg bodyweight of a patient/day. In one embodiment, dosage for an effective EPO therapy is between 60-80 IU/kg bodyweight of a patient/day. In one embodiment, dosage for an effective EPO therapy is between 80-100 IU/kg bodyweight of a patient/day. In one embodiment, dosage for an effective EPO therapy is between 100-120 IU/kg bodyweight of a patient/day. In one embodiment, dosage for an effective EPO therapy is between 120-150 IU/kg bodyweight of a patient/day.

In another embodiment, dosage for an effective EPO therapy is between 18-25 IU/kg bodyweight/day (low dose). In yet another embodiment, dosage for an effective EPO therapy is between 18-30 IU/kg bodyweight/day (low dose). In one embodiment, dosage for an effective EPO therapy is between 35-45 IU/kg bodyweight/day (mid dose). In still another embodiment, dosage for an effective EPO therapy is between 30-50 IU/kg bodyweight/day (mid dose). In one embodiment, dosage for an effective EPO therapy is between 55-65 IU/kg bodyweight/day (high dose). In a further embodiment, dosage for an effective EPO therapy is between 50-65 IU/kg bodyweight/day (high dose).

In one embodiment, dosage for an effective EPO therapy is 20 IU/kg bodyweight of a patient/day. In one embodiment, dosage for an effective EPO therapy is 40 IU/kg bodyweight of a patient/day. In one embodiment, dosage for an effective EPO therapy is 60 IU/kg bodyweight of a patient/day. In one embodiment, dosage for an effective EPO therapy is 80 IU/kg bodyweight of a patient/day. In one embodiment, dosage for an effective EPO therapy is 100 IU/kg bodyweight of a patient/day. In one embodiment, dosage for an effective EPO therapy is 120 IU/kg bodyweight of a patient/day. In one embodiment, dosage for an effective EPO therapy is 150 IU/kg bodyweight of a patient/day. In one embodiment, dosage is not to exceed about 65 IU/kg bodyweight/day.

In alternative embodiments, effective doses may be tailored to each subject individually, taking into account the patient's weight, historical Hb levels and average EPO dose previously administered by ESA injections. The average EPO dose previously administered may be calculated from the time period of one month prior to a method of implantation. Alternatively, the time period for calculation of an average EPO dosage previously administered may be calculated from a time period greater or less than at least on month. Dosage may be based on the amount of EPO administered during the at least one month prior to implantation, wherein the dosage administered is normalized to a daily basis. In some circumstances, the dosage may be based on the amount of EPO administered during at least a two month time period prior to implantation. In certain circumstances, the dosage may be based on the amount of EPO administered during at least a three month time period prior to implantation. In other circumstances, the dosage may be based on the amount of EPO administered during at least a six month time period prior to implantation. For example, if a subject previously received three injections per week totaling 150 U/kg/week, a tailored dosage may include implantation of at least one genetically modified micro-organ producing approximately 20 U/Kg/day.

In one embodiment, the dosage matches the amount a subject previously received, normalized to a daily bases. In another embodiment, the dosage is reduced by up to 25% of the amount a subject previously received, normalized to a daily bases. In yet another embodiment, the dosage is increased by up to 25% of the amount a subject previously received, normalized to a daily bases. In a further embodiment, the dosage is reduced by up to 50% of the amount a subject previously received, normalized to a daily bases. In yet another embodiment, the dosage is increased by up to 50% of the amount a subject previously received, normalized to a daily bases.

In one embodiment, response to implantation of an at least one hEPO-GMMO is sustained elevation of Hb levels for at least one month. In one embodiment, response to implantation of an at least one hEPO-GMMO is sustained elevation of Hb levels for at least two months. In one embodiment, response to implantation of an at least one hEPO-GMMO is sustained elevation of Hb levels for at least three months. In one embodiment, response to implantation of an at least one hEPO-GMMO is sustained elevation of Hb levels for at least four months. In one embodiment, response to implantation of an at least one hEPO-GMMO is sustained elevation of Hb levels for at least five months. In one embodiment, response to implantation of an at least one hEPO-GMMO is sustained elevation of Hb levels for at least six months. In one embodiment, response to implantation of an at least one hEPO-GMMO is sustained elevation of Hb levels for greater than six months. In one embodiment, response to implantation of an at least one hEPO-GMMO is sustained elevation of Hb levels for greater than nine months. In one embodiment, response to implantation of an at least one hEPO-GMMO is sustained elevation of Hb levels for greater than one year.

It may be that the response to implantation of an at least one hEPO-GMMO does not sustain elevation of Hb or provide sufficient elevation. In such a case, additional hEPO-GMMO may be implanted in the subject. For example, if following implantation of at least one hEPO-GMMO the blood Hb level decreases by about 1 g/dl or more per day, or per week, or per two weeks or per month, compared to the baseline Hb average during a one month period prior to implantation, additional hEPO-GMMO may be implanted. Alternatively, if following implantation of at least one hEPO-GMMO the blood Hb level decreases by about 1 g/dl or more per day, or per week, or per two weeks or per month, compared to an initial increased average Hb following implantation, additional hEPO-GMMO may be implanted. In one embodiment, additional hEPO-GMMO may provide up to 25% increased EPO IU. In another embodiment, additional hEPO-GMMO may provide up to 50% increased EPO IU.

Treatment implanting long-lasting erythropoietin formulations, e.g., genetically modified micro-organs expressing and secreting EPO, aims to supply a steady continuous production and delivery of EPO to patients in need. Patients in need may include those suffering from anemia and/or those in need of increased Hb. In certain instances, anemic subjects or those in need of increased Hb may benefit from treatment with a more physiological EPO treatment [Fishbane, S., Recombinant Human Erythropoietin: Has Treatment Reached its Full Potential, Seminars in Dialysis, Vol 19, No 1, 2006, pp. 1-4] Implantation of autologous genetically modified micro-organs secreting and expressing EPO back into a patient, wherein the autologous tissue remains localized and supplies sustained treatment, may provide this benefit. A strong advantage of this method is that if the delivered dose of EPO is too high, or if the treatment needs to be terminated for any reason, one or more of the implanted genetically modified micro-organs may be simply removed (or even potentially ablated in situ) in order to stop the production and delivery of the EPO. In one embodiment, if the blood level of Hb is greater than 11.5 g/dl, then at least one hEPO-GMMO may be removed or inactivated to reduce the EPO U by about 25%. In another embodiment, if the blood level of Hb is greater than 12.0 g/dl, then at least one hEPO-GMMO may be removed or inactivated to reduce the EPO U by about 25%.

In one embodiment, the formulations and method of the present invention may be administered with other treatments that are effective in treating anemia. In one embodiment, other treatments include iron supplements, vitamin B 12 supplements, additional sources of erythropoietin, androgens, growth factors such as G-CSF, or a combination thereof. In another embodiment, the formulations and method of the present invention may be administered in conjunction with other treatments such as blood and marrow stem cell transplants.

In one embodiment, this invention provides a therapeutic formulation as described hereinabove in which the therapeutic polypeptide is interferon or in which the therapeutic nucleic acid encodes interferon, which in one embodiment, is interferon alpha, which in one embodiment, is interferon alpha 2a. In another embodiment, the present invention provides a long-lasting interferon-alpha formulation comprising a genetically modified micro-organ, said micro-organ comprising a vector comprising a nucleic acid sequence operably linked to one or more regulatory sequences, wherein said nucleic acid sequence encodes interferon-alpha and whereby said formulation increases interferon-alpha levels by more than 5% over basal levels and said increased interferon-alpha levels persist for greater than one month. In another embodiment, the invention provides a method of providing a therapeutic formulation to a subject in need in which the therapeutic polypeptide is interferon, or in which the therapeutic nucleic acid encodes, interferon, which in one embodiment, is interferon alpha, which in one embodiment, is interferon alpha 2a. In another embodiment, the invention provides a method of providing a therapeutic polypeptide which is interferon, which in one embodiment, is interferon alpha, which in one embodiment, is interferon alpha 2a to a subject in need.

In one embodiment, interferons are multi-functional cytokines that are capable of producing pleitrophic effects on cells, such as anti-viral, anti-proliferative and anti-inflammatory effects. Because of these cellular responses to interferons, interferon-alpha and interferon-beta have been found to be clinically useful in the treatment of viral, proliferative and inflammatory diseases such as multiple sclerosis, hepatitis B, hepatitis C and several forms of cancer.

Interferon therapies may also have potential use for the treatment of other inflammatory diseases, viral diseases and proliferative diseases. Thus, a subject in need of interferons may have one or all of the above-mentioned diseases or conditions.

There are three major classes of interferons: alpha ($\alpha$), beta ($\beta$), and gamma ($\gamma$). Aside from their antiviral and anti-oncogenic properties, interferons activate macrophage and natural killer lymphocyte, and enhance major histocompatibility complex glycoprotein classes I and II. Interferon-$\alpha$ is secreted by leukocytes (B-cells and T-cells). Interferon-$\beta$ is secreted by fibroblasts, and interferon-$\gamma$ is secreted by T-cells and natural killer lymphocytes.

In one embodiment, the therapeutic polypeptide is interferon alpha, in another embodiment, interferon beta, or in another embodiment, interferon gamma. In another embodiment, the therapeutic polypeptide is any subtype of interferon alpha, including but not limited to: 1, 2, 4, 5, 6, 7, 8, 10, 13, 14, 16, 17, or 21. In another embodiment, the therapeutic polypeptide is interferon omega, epsilon, kappa, or a homolog thereof. In another embodiment, the therapeutic polypeptide is interferon lambda or a homolog thereof. In another embodiment, the therapeutic polypeptide is any subtype of interferon lambda including but not limited to: Interleukin (IL) 28A, IL28B, or IL29. In another embodiment, the therapeutic polypeptide is interferon zeta, nu, tau, delta, or a homolog thereof.

In one embodiment, IFNs bind to a specific cell surface receptor complex, which in one embodiment is interferon alpha receptor (IFNAR) comprising IFNAR1 and IFNAR2 chains, in another embodiment is interferon gamma receptor (IFNGR) complex, which comprises two IFNGR1 and two IFNGR2 subunits, in another embodiment is a receptor complex comprising IL10R2 and IFNLR1. In one embodiment, interferons signal through the JAK-STAT signaling pathway.

In one embodiment, the interferon of the formulations and methods of the instant invention are interferon alpha. In another embodiment, the interferon of the formulations and methods of the instant invention are interferon alpha2b. In one embodiment, IFN-alpha-2b is a recombinant, non-glycosylated 165-amino acid alpha interferon protein comprising the gene for IFN-alpha-2b from human leukocytes. IFN-alpha-2b is a type I, water-soluble interferon with a molecular weight of 19,271 daltons (19.271 kDa). In one embodiment, IFN-alpha-2b has a specific activity of about $2.6 \times 10^8$ (260 million) International Units/mg as measured by HPLC assay.

In one embodiment, IFN-alpha-2b is one of the Type I interferons, which belong to the larger helical cytokine superfamily, which includes growth hormones, interleukins, several colony-stimulating factors and several other regulatory molecules. All function as regulators of cellular activity by interacting with cell-surface receptor complexes, known as IFNAR1 and IFNAR2, and activating various signaling pathways. Interferons produce antiviral and anti-proliferative responses in cells.

In one embodiment, a long-lasting IFN-alpha formulation of the present invention may be used for the prevention or treatment of hairy cell leukemia, venereal warts, Kaposi's Sarcoma, chronic non-A, non-B hepatitis, hepatitis B, or a combination thereof. In another embodiment, a long-lasting IFN-alpha formulation of the present invention may be administered to a subject that is susceptible to one of the above-mentioned diseases or conditions or has been or will be exposed to an infectious agent, as described herein. In another embodiment, a long-lasting IFN-alpha formulation invention may be used for the prevention or treatment of hepatitis C. According to this aspect and in one embodiment, the formulations of the present invention may be administered concurrently or alternately with other hepatitis C treatments, including inter alia, ribavarin, interferons, pegylated interferons or a combination thereof.

In another embodiment, a long-lasting IFN-alpha formulation may be used or evaluated alone or in conjunction with chemotherapeutic agents in a variety of other cellular proliferation disorders, including chronic myelogenous leukemia, multiple myeloma, superficial bladder cancer, skin cancers (including, inter alia, basal cell carcinoma and malignant melanoma), renal cell carcinoma, ovarian cancer, low grade lymphocytic and cutaneous T cell lymphoma, and glioma. In another embodiment, a long-lasting IFN-alpha formulation may be used for the prevention or treatment of solid tumors that arise from lung, colorectal and breast cancer, alone or with other chemotherapeutic agents. In another embodiment, a long-lasting IFN-alpha formulation may be used for the prevention or treatment of multiple sclerosis. In another embodiment, a long-lasting IFN-alpha formulation may be used for the prevention or treatment of histiocytic diseases, which in one embodiment is Erdheim-Chester disease (ECD), which in one embodiment is a potentially fatal disorder that attacks the body's connective tissue and in one embodiment is caused by the overproduction of histiocytes, which in one embodiment, accumulate in loose connective tissue, causing it to become thickened and dense. In another embodiment, a long-lasting IFN-alpha formulation may be used for the prevention or treatment of severe ocular Behcet's disease.

In one embodiment, the interferon alpha gene has a nucleic acid sequence that corresponds to that set forth in Genbank Accession Nos: K01900; M11003; or M71246, or encodes a protein sequence that corresponds to that set forth in Genbank Accession Nos: AAA52716; AAA52724; or AAA52713. In one embodiment, the interferon beta gene has a nucleic acid sequence that corresponds to that set forth in Genbank Accession Nos: M25460; AL390882; or CH236948, or encodes a protein sequence that corresponds to that set forth in Genbank Accession Nos: AAC41702; CAH70160; or EAL24265. In one embodiment, the interferon gamma gene has a nucleic acid sequence that corresponds to that set forth in Genbank Accession Nos: J00219; AF506749; NM_000619; or X62468, or encodes a protein sequence that corresponds to that set forth in Genbank Accession Nos: AAB59534; AAM28885; NP_000610; or CAA44325. In another embodiment, the interferon alpha gene has a nucleic acid sequence as presented in SEQ ID No: 8, while in another embodiment, the interferon alpha gene has an amino acid sequence as presented in SEQ ID No: 9. In another embodiment, the interferon alpha gene has a nucleic acid that is homologous to that presented in SEQ ID No: 8, while in another embodiment, the interferon alpha gene has an amino acid sequence that is homologous to that presented in SEQ ID No: 9.

In another embodiment, the present invention provides a method of delivering interferon-alpha to a subject in need over a sustained period comprising: providing one or more genetically modified micro-organs, said micro-organs comprising a vector comprising a nucleic acid sequence operably linked to one or more regulatory sequences; and implanting said genetically modified micro-organ in said subject, wherein said nucleic acid sequence encodes interferon-alpha and whereby interferon-alpha levels are increased by more than 5% over basal levels and said increased interferon-alpha levels persist for greater than one month.

In one embodiment, the formulations and methods of the present invention provide a nucleic acid optimized for increased expression levels, duration, or a combination thereof of a therapeutic polypeptide encoded by said nucleic acid. In another embodiment, the invention provides a nucleic acid sequence with greater than 85% homology to SEQ ID No: 1, a vector comprising such a nucleic acid sequence, and a cell comprising such as vector.

In another embodiment, the invention provides a nucleic acid sequence with greater than 85% homology to SEQ ID No: 2, a vector comprising such a nucleic acid sequence, and a cell comprising such as vector.

The term "homology", as used herein, when in reference to any nucleic acid sequence indicates a percentage of nucleotides in a candidate sequence that is identical with the nucleotides of a corresponding native nucleic acid sequence.

In one embodiment, the terms "homology", "homologue" or "homologous", in any instance, indicate that the sequence referred to, exhibits, in one embodiment at least 70% correspondence with the indicated sequence. In another embodiment, the nucleic acid sequence exhibits at least 72% correspondence with the indicated sequence. In another embodiment, the nucleic acid sequence exhibits at least 75% correspondence with the indicated sequence. In another embodiment, the nucleic acid sequence exhibits at least 77% correspondence with the indicated sequence. In another embodiment, the nucleic acid sequence exhibits at least 80% correspondence with the indicated sequence. In another embodiment, the nucleic acid sequence exhibits at least 82% correspondence with the indicated sequence. In another embodiment, the nucleic acid sequence exhibits at least 85% correspondence with the indicated sequence. In another embodiment, the nucleic acid sequence exhibits at least 87% correspondence with the indicated sequence. In another embodiment, the nucleic acid sequence exhibits at least 90% correspondence with the indicated sequence. In another embodiment, the nucleic acid sequence exhibits at least 92% correspondence with the indicated sequence. In another embodiment, the nucleic acid sequence exhibits at least 95% or more correspondence with the indicated sequence. In another embodiment, the nucleic acid sequence exhibits 95%-100% correspondence to the indicated sequence. Similarly, reference to a correspondence to a particular sequence includes both direct correspondence, as well as homology to that sequence as herein defined.

Homology may be determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

An additional means of determining homology is via determination of nucleic acid sequence hybridization, methods of which are well described in the art (See, for example, "Nucleic Acid Hybridization" Hames, B. D., and Higgins S. J., Eds. (1985); Sambrook et al., 1989, Molecular Cloning, A Laboratory Manual, (Volumes 1-3) Cold Spring Harbor Press, N.Y.; and Ausubel et al., 1989, Current Protocols in Molecular Biology, Green Publishing Associates and Wiley Interscience, N.Y). In one embodiment, methods of hybridization may be carried out under moderate to stringent conditions. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

In one embodiment, the present invention provides therapeutic formulations comprising micro-organs and methods of use thereof. In one embodiment, the preparation of therapeutic micro-organs comprises (a) obtaining a plurality of micro-organ explants from a donor subject, each of the plurality of micro-organ explants comprises a population of cells, each of the plurality of micro-organ explants maintaining a microarchitecture of an organ from which it is derived and at the same time having dimensions selected so as to allow diffusion of adequate nutrients and gases to cells in the micro-organ explants and diffusion of cellular waste out of the micro-organ explants so as to minimize cellular toxicity and concomitant death due to insufficient nutrition and accumulation of the waste in the micro-organ explants; (b) genetically modifying the plurality of micro-organ explants, so as to obtain a plurality of genetically modified micro-organ explants, said micro-organs comprising and secreting the proteins differing by the at least one amino acid; and (c) implanting the plurality of genetically modified micro-organ explants within a plurality of recipient subjects.

Methods for the preparation and processing of micro-organs into genetically modified micro-organs are disclosed in WO2004/099363, incorporated herein by reference in their entirety. Micro-organs comprise tissue dimensions defined such that diffusion of nutrients and gases into every cell in the three dimensional micro-organ, and sufficient diffusion of cellular wastes out of the explant, is assured. Ex vivo maintenance of the micro-organs, which in one embodiment, is in minimal media, can continue for an extended period of time, whereupon controlled ex vivo transduction incorporating desired gene candidates within cells of the micro-organs using viral or non-viral vectors occurs, thus creating genetically modified micro-organs.

In one embodiment, micro-organs are harvested using a drill and coring needle, as described hereinbelow. In another embodiment, micro-organs are harvested using a harvesting system that utilizes a vacuum to hold the skin taut and open the slits during insertion of the coring drill. In another embodiment, any tool which may be used to harvest dermal tissue may be used to harvest micro-organs of the appropriate size, including but not limited to those tools and methods described in PCT Application WO 04/099363.

Incorporation of recombinant nucleic acid within the micro-organs to generate genetically modified micro-organs or biopumps can be accomplished through a number of methods well known in the art. Nucleic acid constructs can be utilized to stably or transiently transduce the micro-organ cells. In stable transduction, the nucleic acid molecule is integrated into the micro-organ cells genome and as such it represents a stable and inherited trait. In transient transduction, the nucleic acid molecule is maintained in the transduced cells as an episome and is expressed by the cells but it is not integrated into the genome. Such an episome can lead to transient expression when the transduced cells are rapidly dividing cells due to loss of the episome or to long term expression wherein the transduced cells are non-dividing cells.

Typically the nucleic acid sequence is subcloned within a particular vector, depending upon the preferred method of introduction of the sequence to within the micro-organs, as described hereinabove. Once the desired nucleic acid segment is subcloned into a particular vector it thereby becomes a recombinant vector.

In one embodiment, micro-organs are incubated at 32° C. before and after genetic modification, while in another embodiment, they are incubated at 37° C. In another embodiment, micro-organs are incubated at 33° C., 34° C., 35° C., 36° C., 38° C., 39° C., 40° C., 28° C., 30° C., 31° C., 25° C., 42° C., or 45° C.

In one embodiment, micro-organs are incubated at 10% $CO_2$ before and after genetic modification, while in another embodiment, they are incubated at 5% $CO_2$. In another embodiment, micro-organs are incubated at 12% $CO_2$, 15% $CO_2$, 17% $CO_2$, or 20% $CO_2$. In another embodiment, micro-organs are incubated at 2% $CO_2$, 6% $CO_2$, 7% $CO_2$, 8% $CO_2$, or 9% $CO_2$.

In another embodiment, incubation temperatures, $CO_2$ concentrations, or a combination thereof may be kept at a single temperature or concentration before, during, and after genetic modification, while in another embodiment, incubation temperatures, $CO_2$ concentrations, or a combination thereof may be adjusted at different points before, during, and after genetic modification of micro-organs.

In another embodiment, micro-organs are incubated at 85-100% humidity, which in one embodiment is 95% humidity, in another embodiment, 90% humidity, and in another embodiment, 98% humidity.

In one embodiment, the levels of therapeutic nucleic acids or polypeptides may be detected using any method known in the art. The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. In one embodiment, ELISA, Western blots, or radioimmunoassay may be used to detect proteins. If the gene product of interest to be expressed by a cell is not readily assayable, an expression system can first be optimized using a reporter gene linked to the regulatory elements and vector to be used. The reporter gene encodes a gene product which is easily detectable and, thus, can be used to evaluate efficacy of the system. Standard reporter genes used in the art include genes encoding β-galactosidase, chloramphenicol acetyl transferase, luciferase and human growth hormone.

Thus, in one embodiment, therapeutic polypeptide or nucleic acid expression levels are measured in vitro, while in another embodiment, therapeutic polypeptide or nucleic acid expression levels are measured in vivo. In one embodiment, in vitro determination of polypeptide or nucleic acid expression levels, which in one embodiment, is EPO levels and in another embodiment, IFN-alpha levels, allows a determination of the number of micro organs to be implanted in a patient via determining the secretion level of a therapeutic agent by a micro-organ in vitro; estimating a relationship between in vitro production and secretions levels and in vivo serum levels of the therapeutic agent; and determining an amount of the therapeutic formulation to be implanted, based on the determined secretion level and the estimated relationship.

In another preferred embodiment of this invention, polynucleotide(s) can also include trans-, or cis-acting enhancer or suppresser elements which regulate either the transcription or translation of endogenous genes expressed within the cells of the micro-organs, or additional recombinant genes introduced into the micro-organs. Numerous examples of suitable translational or transcriptional regulatory elements, which can be utilized in mammalian cells, are known in the art.

For example, transcriptional regulatory elements comprise cis- or trans-acting elements, which are necessary for activation of transcription from specific promoters [(Carey et al., (1989), J. Mol. Biol. 209:423-432; Cress et al., (1991), Science 251:87-90; and Sadowski et al., (1988), Nature 335: 5631-564)].

Translational activators are exemplified by the cauliflower mosaic virus translational activator (TAV) [see for example, Futterer and Hohn, (1991), EMBO J. 10:3887-3896]. In this system a bi-cistronic mRNA is produced. That is, two coding regions are transcribed in the same mRNA from the same promoter. In the absence of TAV, only the first cistron is translated by the ribosomes, however, in cells expressing TAV, both cistrons are translated.

The polynucleotide sequence of cis-acting regulatory elements can be introduced into cells of micro-organs via commonly practiced gene knock-in techniques. For a review of gene knock-in/out methodology see, for example, U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson, Methods in Enzymology, 194:251-270, 1991; Capecchi, Science 244: 1288-1292, 1989; Davies et al., Nucleic Acids Research, 20 (11) 2693-2698, 1992; Dickinson et al., Human Molecular Genetics, 2(8):1299-1302, 1993; Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742-750 1991; Jakobovits et al., Nature, 362:255-261 1993; Lamb et al., Nature Genetics, 5: 22-29, 1993; Pearson and Choi, Proc. Natl. Acad. Sci. USA, 1993, 90:10578-82; Rothstein, Methods in Enzymology, 194:281-301, 1991; Schedl et al., Nature, 362: 258-261, 1993; Strauss et al., Science, 259:1904-1907, 1993, WO 94/23049, WO 93/14200, WO 94/06908 and WO 94/28123 also provide information.

Down-regulation of endogenous sequences may also be desired, in order to assess production of the recombinant product exclusively. Toward this end, antisense RNA may be employed as a means of endogenous sequence inactivation. Exogenous polynucleotide(s) encoding sequences complementary to the endogenous mRNA sequences are transcribed within the cells of the micro-organ. Down regulation can also be effected via gene knock-out techniques, practices well known in the art ("Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988)).

Over expression of the recombinant product may be desired as well. Over expression may be accomplished by providing a high copy number of one or more coding sequences in the respective vectors. These exogenous polynucleotide sequences can be placed under transcriptional control of a suitable promoter of a mammalian expression vectors to regulate their expression. In another embodiment, multiple copies of the same gene or of several related genes may be used as a means to increase polypeptide or nucleic acid expression. In one embodiment, expression is stabilized by DNA elements, which in one embodiment are matrix-associating regions (MARs) or scaffold-associating regions (SARs).

In one embodiment, an adenoviral vector is the vector of the compositions and for use in the methods of the present invention. In an embodiment in which an adenoviral vector is used as a vector, the helper-dependent adenovirus system may be used in one embodiment, to prepare therapeutic polypeptide or nucleic acid-expressing helper-dependent adenovirus vector for transforming micro-organs. In one embodiment, such a helper-dependent adenovirus system comprises a helper-dependent adenovirus, a helper virus, and a producer cell line is used in the preparation of the formulation of the present invention is as described in Palmer and Ng, 2003 Mol Ther 8:846 and in Palmer and Ng, 2004 Mol Ther 10:792, which are hereby incorporated herein by reference in their entirety.

In one embodiment, a helper cell line, designated 293, which was transformed from human embryonic kidney cells by Ad5 DNA fragments and constitutively expresses E1 proteins is used to generate and propagate replication deficient adenoviral vectors. In another embodiment, helper cell lines may be derived from human muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells.

In one embodiment, micro-organs are maintained ex vivo for a period of time, which may range from several hours to several months. In one embodiment, maintenance ex vivo refers to maintenance of a micro-organ following ex vivo genetic manipulation using a viral vector, i.e., maintenance of a GMMO. In another embodiment, maintenance ex vivo refers to maintenance of a micro-organ prior to genetic manipulation thereof.

In one embodiment, genetically modified micro-organs are maintained for several days, and in another embodiment, for several weeks prior to implantation. In one embodiment, micro-organs are maintained for between 9-14 days prior to implantation. In one embodiment, micro-organs are maintained for between two to four weeks prior to implantation. In one embodiment, micro-organs are maintained for three weeks prior to implantation. In one embodiment, micro-organs are maintained for four weeks or more prior to implantation. In yet another embodiment, micro-organs are maintained for at least 9 days.

Without being limited by theory, in one embodiment, said incubation allows cells to process and break down viral proteins, which in one embodiment are viral capsids, present as a result of viral vector transduction. In one embodiment, such a turnover of capsid proteins occurs within 2-3 days, so that, in one embodiment, little if any viral capsid proteins remain by the $10^{th}$ day ex vivo. In one embodiment, the breaking down of viral capsids further reduces the immunogenicity of the formulations of the instant invention and increases the expression levels and expression duration of the gene or genes of interest. In another embodiment, said incubation allows the early HD-Ad vector-induced innate immune responses to occur in vitro, which in one embodiment, will not persist beyond 24 hours in the absence of Adeno gene transcription. In another embodiment, the later adaptive responses that normally follow the administration of transcription-competent first-generation-Ad vectors, which are predominantly characterized in one embodiment, by lymphocyte infiltration and in another embodiment by induction of Ad-specific CTL's, are not be elicited by HD-Ad vectors.

In one embodiment, the ex vivo micro-organ is exposed to viral vector at a dosage of $1.6\text{-}3\times10^9$ infectious particles (ip)/ml, $3\text{-}4\times10^{12}$ viral particles/ml, or $2\times10^{11}$ viral particles/ml. In another embodiment, ex vivo micro-organs are exposed to viral vector at a dosage of $1\times10^3$ to $1\times10^{12}$ viral particles/ml, in another embodiment from $1\times10^3$ to $1\times10^9$, and in another embodiment, from $1\times10^6$ to $1\times10^9$ and in another embodiment, $1\times10^6$ to $1\times10^{12}$ viral particles/ml. In one embodiment, the dosage of viral particles/g body weight of subject that are administered to a subject within a micro-organ is less than $1\times10^3$, and in another embodiment, less than $1\times10^2$, and in another embodiment, less than $1\times10^1$ viral particles/g body weight of subject.

In one embodiment, growth factors are used to increase the number of cells in the micro-organs.

In one embodiment, in vitro expression can be assessed prior to implantation, enabling the possibility for in vitro to in vivo correlation studies of expressed recombinant proteins.

In some embodiments of the invention, the amounts of tissue sample including a genetically modified cell(s) to be implanted are determined from one or more of: corresponding amounts of the therapeutic agent of interest routinely administered to such subjects based on regulatory guidelines, specific clinical protocols or population statistics for similar subjects, corresponding amounts of the therapeutic agent such as protein of interest specifically to that same subject in the case that he/she has received it via injections or other routes previously, subject data such as weight, age, physical condition, clinical status, pharmacokinetic data from previous tissue sample which includes a genetically modified cell administration to other similar subjects, response to previous tissue sample which includes a genetically modified cell administration to that subject, or a combination thereof. Thus, in one embodiment, the level of expression of gene products by one or more micro-organs is determined in vitro, a relationship between in vitro and in vivo therapeutic polypeptide or nucleic acid expression levels is determined or estimated, and the number of micro-organs to be implanted in a particular patient is determined based on the calculated or estimated relationship. The dosage of the therapeutic agent may be adjusted as described previously (WO2004/099363).

In one embodiment, a micro-organ or a genetically modified micro-organ may be maintained in vitro for a proscribed period of time until they are needed for implantation into a host. In one embodiment, a micro-organ or a genetically modified micro-organ may be maintained or stored in culture for between 1-7 days, between 1-8 weeks, or for 1-4 months. In another embodiment, the therapeutic agent, left in the supernatant medium surrounding the tissue sample, can be isolated and injected or applied to the same or a different subject.

Alternatively or additionally, a genetically modified micro-organ can be cryogenically preserved by methods known in the art, for example, without limitation, gradual freezing (0° C., −20° C., −80° C., −196° C.) in DMEM containing 10% DMSO, immediately after being formed from the tissue sample or after genetic alteration.

Administration of the formulation of the invention may be by implanting into the subject in need. In one embodiment, the formulation of the instant invention may be implanted in an organ or system that is affected by a disease or disorder to be treated or prevented by a method or route which results in localization of the micro-organ at a desired site. In another embodiment, the location of the implanted formulation may be distal from an organ or system that is affected by a disease or disorder. Thus, while in one embodiment, the recombinant protein is released locally, in another embodiment, the recombinant protein diffuses to the lymphatic system, which in one embodiment, may ultimately lead to systemic distribution of the recombinant protein. Thus, the present invention provides for the use of therapeutic formulations in various concentrations to treat a disease or disorder manifesting in any part of the subject in need.

According to this aspect and in one embodiment, formulations of the instant invention may be implanted intratumorally. In another embodiment, formulations may be implanted at a site distal from the tumor, which in one embodiment is associated with metastasis of a particular type of tumor. In another embodiment, formulations of the instant invention may be implanted into the kidney of a subject, which in one embodiment is a subcapsular implantation. In another embodiment, formulations of the instant invention are implanted laparascopically.

In one embodiment, the formulations of the invention may be implanted a single time for acute treatment of temporary conditions, or may be implanted more than one time, especially in the case of progressive, recurrent, or degenerative disease. In one embodiment, one or more formulations of the invention may be administered simultaneously, or in another embodiment, they may be administered in a staggered fashion. In one embodiment, the staggered fashion may be dictated by the stage or phase of the disease.

In one embodiment, the micro-organ is implanted at a desired location in the subject in such a way that at least a portion of the cells of the micro-organ remain viable. In one embodiment of this invention, at least about 5%, in another embodiment of this invention, at least about 10%, in another embodiment of this invention, at least about 20%, in another embodiment of this invention, at least about 30%, in another embodiment of this invention, at least about 40%, and in another embodiment of this invention, at least about 50% or more of the cells remain viable after administration to a subject. The period of viability of the cells after administration to a subject can be as short as a few hours, e.g., twenty-four hours, to a few days, to as long as a few weeks to months or years.

Micro-organ implantation within a recipient subject provides for a sustained dosage of the recombinant product. The micro-organs may be prepared, prior to implantation, for efficient incorporation within the host facilitating, for example, formation of blood vessels within the implanted tissue. Recombinant products may therefore be delivered immediately to peripheral recipient circulation, following production. Alternatively, micro-organs may be prepared, prior to implantation, to prevent cell adherence and efficient incorporation within the host. Examples of methods that prevent blood vessel formation include encasement of the micro-organs within commercially available cell-impermeant diameter restricted biological mesh bags made of silk or nylon, or others such as, for example GORE-TEX bags (Terrill P J, Kedwards S M, and Lawrence J C. (1991) The use of GORE-TEX bags for hand burns. Burns 17(2): 161-5), or other porous membranes that are coated with a material that prevents cellular adhesion, for example Teflon.

Gene products produced by micro-organs can then be delivered via, for example, polymeric devices designed for the controlled delivery compounds, e.g., drugs, including proteinaceous biopharmaceuticals. A variety of biocompatible polymers (including hydrogels), including both biodegradable and non-degradable polymers, can be used to form an implant for the sustained release of a gene product of the micro-organs in context of the invention at a particular target site. The generation of such implants is generally known in the art (see, for example, Concise Encyclopedia of Medical & Dental Materials, ed. By David Williams (MIT Press: Cambridge, Mass., 1990); Sabel et al. U.S. Pat. No. 4,883,666; Aebischer et al. U.S. Pat. No. 4,892,538; Aebischer et al. U.S. Pat. No. 5,106,627; Lim U.S. Pat. No. 4,391,909; and Sefton U.S. Pat. No. 4,353,888). In one embodiment, a GMMO is encapsulated. In another embodiment, a GMMO is not encapsulated.

Implantation of genetically modified micro-organs according to the present invention can be effected via standard surgical techniques or via injecting micro-organ preparations into the intended tissue regions of the mammal utilizing specially adapted syringes employing a needle of a gauge suitable for the administration of micro-organs. In another embodiment, a catheter is employed for implanted micro-organs. In one embodiment, any of the implantation methods described in PCT Publication WO2 04/099363 may be used and is considered an embodiment of this invention.

In one embodiment, micro-organs are implanted subcutaneously, intradermally, subdermally, intramuscularly, intraperitoneally or intragastrically. In one embodiment, the term implanted excludes being grafted as a split-thickness or full-thickness skin graft. In one embodiment of the present invention, the donor micro-organs utilized for implantation are preferably prepared from an organ tissue of the recipient mammal (i.e. autologous), or a syngeneic mammal, although allogeneic and xenogeneic tissue can also be utilized for the preparation of the micro-organs providing measures are taken prior to, or during implantation, so as to avoid graft rejection and/or graft versus host disease (GVHD). As used herein, GVHD refers to graft versus host disease, a consequence of tissue transplantation (the graft) caused by the transplant immune response against the recipient host. More specifically, graft-versus-host disease is caused by donor T-lymphocytes (T cells), recognizing the recipient as being foreign and attacking cells of the recipient. Numerous methods for preventing or alleviating graft rejection or GVHD are known in the art and may be used in the methods of this invention. In one embodiment, to facilitate transplantation of the cell populations within a tissue which may be subject to immunological attack by the host, e.g., where xenogenic grafting is used, such as swine-human transplantations, the micro-organ may be inserted into or encapsulated by biocompatible immunoprotected material such as rechargeable, non-biodegradable or biodegradable devices and then transplanted into the recipient subject. In another embodiment, the micro-organ is not inserted into or encapsulated by biocompatible immunoprotected material such as rechargeable, non-biodegradable or biodegradable devices.

In another embodiment, the donor micro-organs utilized for implantation are preferably prepared from a donor who is human leukocyte antigen (HLA)-matched with the recipient, where in one embodiment, HLA is the major histocompatibility complex in humans. In one embodiment, donor and recipient are matched for class I major histocompatibility complex (MHC) genes, class II MHC genes, or a combination thereof. In one embodiment, class I MHC genes comprise HLA-A, HLA-B, and HLA-C, wherein in one embodiment, a mismatch of class I MHC genes increases the risk of graft rejection, and in one embodiment, class II MHC genes comprise HLA-DPA1, HLA-DPB1, HLA-DQA1, HLA-DQB1, HLA-DRA, HLA-DRB1, wherein in one embodiment, a mismatch of class II MHC genes increases the risk of GVHD. In another embodiment, donor and recipient are matched for HLA-DM and HLA-DO genes.

In one embodiment, viral turnover or elimination from cells ex vivo is enhanced via techniques know in the art, such as physical methods, which in one embodiment is heating, use of antiviral agents, agents which stimulate viral turnovers by cells, etc.

In one embodiment, while the long-lasting formulations of the present invention increase the level and duration of nucleic acid or polypeptide expression, the levels of nucleic acid or polypeptide expression do not remain elevated indefinitely.

In contrast to other methods involving transient transduction of cells, or cells that turn over rapidly, the long-lasting EPO formulation of the instant invention comprises cells that are no longer replicating. Therefore, the EPO formulation produces a stable protein from a stable construct and is expected to continue producing the protein already characterized.

EXAMPLES

Experimental Materials and Methods

Materials and Equipment List

Production medium was used to grow micro-organs and comprises DMEM-HEPES Medium (High glucose 4,500 mg/L and 25 mM HEPES; Hi-Clone Cat#SH3A1448.02) comprising 1% glutamine and supplemented with 50 µg/ml Gentamycin (RAFA labs, for injection) and 0.1% Amphotericin B (BMS, Fungizone I.V.) (final concentration in the media 2.5 µg/ml Amphotericin B). In some experiments, 10% serum substitute supplement (SSS, Irvine Scientific, Cat #99193), 10% autologous human serum, or 10% Fetal bovine serum (FBS or FCS) was added to the production medium.

Harvesting of Dermal Micro-Organs

A. Method I.

Human dermal micro-organs were harvested from an area of skin from a region of the donor's lower abdomen. In certain instances, the dimensions of the dermal micro-organs harvested were approximately 1.5-2.5 mm in width and 30 mm in length. In some cases, to prevent the harvest of the epidermis, a shallow slit (1-2 mm deep) passing through the stratum cornea into the dermis was cut along a straight line at one side of the skin region from which the micro-organs were to be harvested, and a similar slit was cut 30 mm away from and parallel to the first slit. The distance between the slits determined the micro-organ length and was consistent throughout the experiments.

In certain cases, a thin gauge (typically 22GA) hypodermic needle attached to a 1 ml syringe filled with sterile saline was inserted into the exposed dermis at the first slit and slid along the dermis of the harvesting site towards the opposite slit, with the needles angled as necessary so that it exited through the dermis at the opposite slit.

Next, in some cases, the outer skin along the length of the guiding needle was pinched with a surgical clamp. The needle embedded in the dermis was lifted slightly to raise the area of skin surrounding it and sometimes a hook shaped device beneath the inserted hypodermic needle's point was used to assist in lifting the skin before it's pinched. The tip of the guide needle protruding from its point of exit, was inserted into the sharp leading end of a coring needle (1-3 mm in diameter, Point Technologies, Colo. USA), which was held by a commercially available drill (such as Aesculap Micro Speed GD 650, GD 657). A small amount of sterile saline was injected from the syringe into the coring needle. The drill is activated to rotate the coring needle at high speed (typically 3000-7000 RPM) and while rotating, the drill and coring needle are manually urged forward along the axis of the guide needle to cut a 30-40 mm long cylindrical dermal core (dermal micro-organ) having an outer diameter approximately that of the inner diameter of the coring needle. The dermal micro-organ usually remained attached to the guide needle, which was withdrawn from within the coring needle and placed in Production media (as described hereinabove), and the coring needle was removed from the skin.

In many cases, using tweezers, each micro-organ was transferred to a labeled single well in a 24 well plate containing 1000 µl Production Medium. To remove the debris, two additional media changes of 1000 µl were performed for each micro-organ. The plates containing the micro-organs in 1000 µl production media were then transferred to an incubator that had been equilibrated to 32° C., 10% $CO_2$, and ~95% humidity for a 24 hr recovery period.

B. Method II.

Micro-organs (MOs) are harvested under local anesthesia from the dermis of the lower abdomen or the upper or lower back of the patient that will be treated, with dimensions of approximately 1.5-2.5 mm in width, and 30 mm in length. Their dimensions and appearance remain essentially the same during the entire hEPO-GMMO Biopump ex-vivo production process.

The dermis micro-organs are transported under controlled conditions to a contract cGMP (current Good Manufacturing Practice) processing facility. Upon receipt at the cGMP processing center, the MOs are divided into two subsets: those to be processed immediately into Biopumps, and those that will be cryopreserved for later processing, if required, into Biopumps. The decision as to how many will be processed immediately will be based on an estimate of the EPO dose needed for that patient and an estimate of average secretion levels from typical Biopumps based on thousands of processed Biopumps in pre-clinical and clinical testing.

For the MOs that are processed immediately, the HDAd-EPO vector is used to perform the transduction. After transduction, residual viral particles are removed by several media exchanges. The Biopumps (transduced micro-organs) are maintained in culture for approximately one week in order to assay for protein secretion levels and sterility. Release criteria of processed Biopumps are listed in Table 1.

TABLE 1

| Test | Sampled | Release Criteria |
|---|---|---|
| Sterility | Day of release | No growth of bacteria or fungi at 14 days. |
| Gram Stain | Day of release | Negative |
| Mycoplasma | 3 days prior to release | Negative |
| Endotoxin | 3 days prior to release | Less than 0.5 EU/mL |
| EPO identity | 3 days prior to release and day of release | Positive for EPO secretion |
| EPO activity | 3 days prior to release and day of release | EPO secretion >100 U/Biopump/day |
| Glucose consumption | 3 days prior to release and day of release | Total glucose consumed >150 µg/Biopump/3 days |

The Biopumps are then transported under controlled conditions back to the treatment center for subcutaneous implantation under local anesthesia in the abdominal wall or the upper or lower back of the same patient.

Micro-organs retrieved from cryostorage for processing, if required, into Biopumps are first thawed prior to undergoing the transduction and maintenance procedures, as detailed above. Data demonstrate the comparability of Biopumps produced from fresh and cryopreserved MOs.

The decision as to how many dermal micro-organs are transduced at any given time, is based upon the estimated dose needed for the patient and an estimate of average secretion levels from typical genetically modified dermal micro-organs. Dermal micro-organs not used immediately for transduction are cryopreserved for later processing Virus Transduction Each micro-organ was transferred for transduction into a well of a 48-well plate, which have smaller wells requiring smaller total fluid volume, to conserve virus. The medium was carefully removed from each well without disturbing the micro-organ inside. During the preclinical experiments, three different vectors were tested: $1.6-3\times10^9$ infectious particles (ip)/ml of first generation adenovirus (Molecular Medicine), approximately $3-4\times10^{12}$ viral particles/ml helper-dependent adenovirus (Baylor), or approximately $2\times10^{11}$ viral particles/ml adeno-associated virus (University of Pennsylvania), each comprising recombinant human EPO gene, optimized recombinant human EPO gene, or optimized IFN-alpha gene, were each diluted 1:10, 1:25, 1:50, 1:100, 1:500, or 1:1000 in DMEM-HEPES (Gibco Cat#42430-025) with or without FCS. Each well of the 48-well plates was filled with 100 µL of one of the diluted titers of a virus. The plate was placed in a $CO_2$ incubator and transduction was assisted by agitation on a digital microtiter shaker at 300 rpm for a period of 2 hours and an additional 16-22 hour incubation without shaking.

The transduced micro-organs were transferred to a 24-well plate after transduction and then washed three times with 1 mL production media (without FCS) to remove the non-transduced viral particles. After washing, the biopumps were maintained in 1 mL production media in a standard high humidity $CO_2$ incubator at 95% humidity, 10% $CO_2$, and 32° C. Seventy-two hours after the removal of the viral vector, the production medium was replaced with fresh medium, and aliquots of the spent medium were assayed for secreted recombinant protein levels.

HDAd-EPO Vector for Clinical Trials

The delivery vector for the clinical trials described below in Examples 3 and 4, which is used ex-vivo to transduce the cells of the micro-organ tissue samples which are biopsied from the dermis of the patient being treated, is a non-replicating helper-dependent Adenoviral (HDAd) vector.

The HDAd vector may provide sustained protein expression and may prevent immune rejection. HDAd vectors lack all viral protein coding sequences and contain only the cis-acting elements required to replicate and package the vector DNA. Consequently, HDAd vectors may avoid the adaptive immune response that normally follows the administration of first-generation Adeno vectors, thus giving the HDAd vectors an immunological advantage [Muruve D A, et al, Helper-dependent adenovirus vectors elicit intact innate but attenuated adaptive host immune responses in vivo. J Virol 2004; 78 (11):5966-5972. In addition, the results of Examples 1, 2 and 5 demonstrated that HDAd vectors exhibit stable long-term transgene expression ex vivo. HDAd retain all the first-generation adenovirus advantages including high titer production, efficient infection of a broad range of cell types, and the ability to infect dividing and nondividing cells. Moreover, they express no viral proteins, can accommodate up to 36 kb of foreign DNA, and exhibit reduced tissue toxicity and prolonged transgene expression as compared with first-generation adenoviral vectors.

Figure 17:
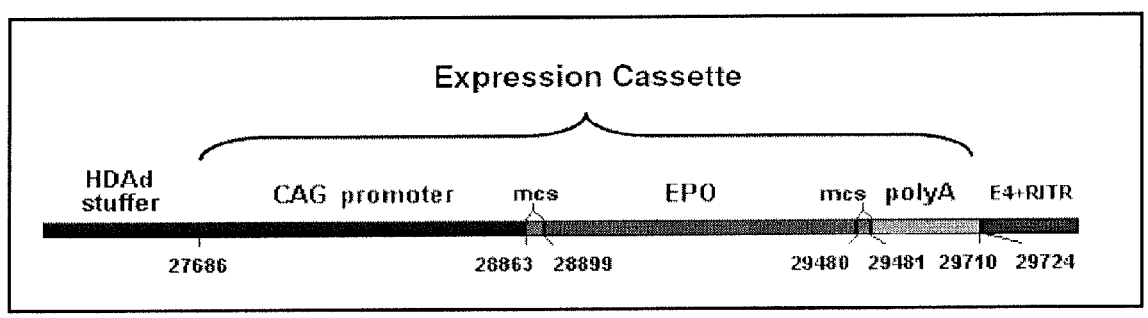
FIG. 17 presents an expression cassette for HDAd-hEPO vector.

The expression cassette within the HDAd vector includes the gene for erythropoietin and a CAG promoter. FIG. 17 presents a map of the elements of the expression cassette. The nucleic acid sequence of the CAG-EPO expression cassette for Examples 3 and 4 is presented as SEQ ID No. 11. Included are multiple cloning site sequences (SEQ ID Nos. 14 and 15); a CAG promoter sequence (SEQ ID No. 12); human EPO intron-less gene from ATG to the stop codon (SEQ ID No. 7); and SV40 poly A sequence (SEQ ID No. 13).

The major steps in the derivation of the HDAd construct were as follows: pAd-CMV-EPO→pAd-CAG-EPO→pΔ28E4-CAG-EPO→HDAd-CAG-EPO.

Construction of pAd-CAG-EPO plasmid was as follows. The pAD-CMV-EPO vector was provided by Dr. Paul Robbins from the University of Pittsburgh (Hardy S., et al., 1997, J. Virol. 71(3):1842-1849, Lippin Y. et al., 2005, Blood 106 (7): 2280-2286). In order to achieve higher levels of transgene expression, traditional cloning techniques have been used to replace the CMV promoter with the CAG promoter, in order to arrive at the pAd-CAG-EPO plasmid.

Construction of pΔ28E4-CAG-EPO plasmid was as follows: pΔ28E4 (Toietta et al., 2002, Mol. Ther. 5: 204-210) was used as the backbone to create the pΔ28E4-CAG-EPO plasmid. This pΔ28E4 plasmid contains two genomic human DNA stuffer sequences: the first corresponds to chromosome x HPRT1 (accession#AC004383 nt 60989-44991), and the second fragment corresponds to chromosome x clone CTD-2537J14 map q28 (accession#AC109994 nt 66942-78052). These DNA fragments were inserted into pΔ28E4 as stuffer DNA in order to achieve the correct vector size that will enable the efficient generation of HDAd viral particles.

Figure 18:
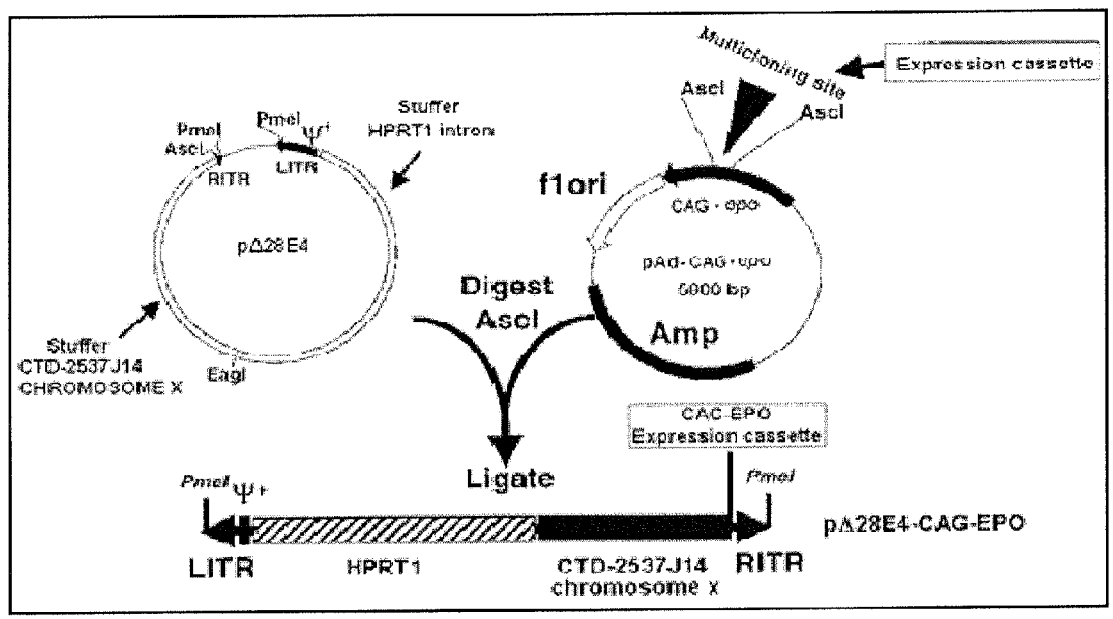
FIG. 18 illustrates schematically construction of pΔ28E4-CAG-EPO plasmid.

The pΔ28E4-CAG-EPO plasmid was constructed by conventional cloning techniques. The CAG-EPO expression cassette from pAd-CAG-EPO plasmid was inserted into the AscI unique site of the HDAd cloning shuttle vector, pΔ28E4, generating the pΔ28E4-CAG-EPO construct, which has the appropriate size for efficient and stable viral packaging. FIG. 18 illustrates the cloning steps for the pΔ28E4-CAG-EPO plasmid.

In addition to the HDAd-CAG-EPO sequences, the pΔ28E4-CAG-EPO contains bacterial sequences of Kanamycin resistance and origin of replication, which are necessary for the DNA amplifying in bacteria (size 32.5 kb).

Figure 19:
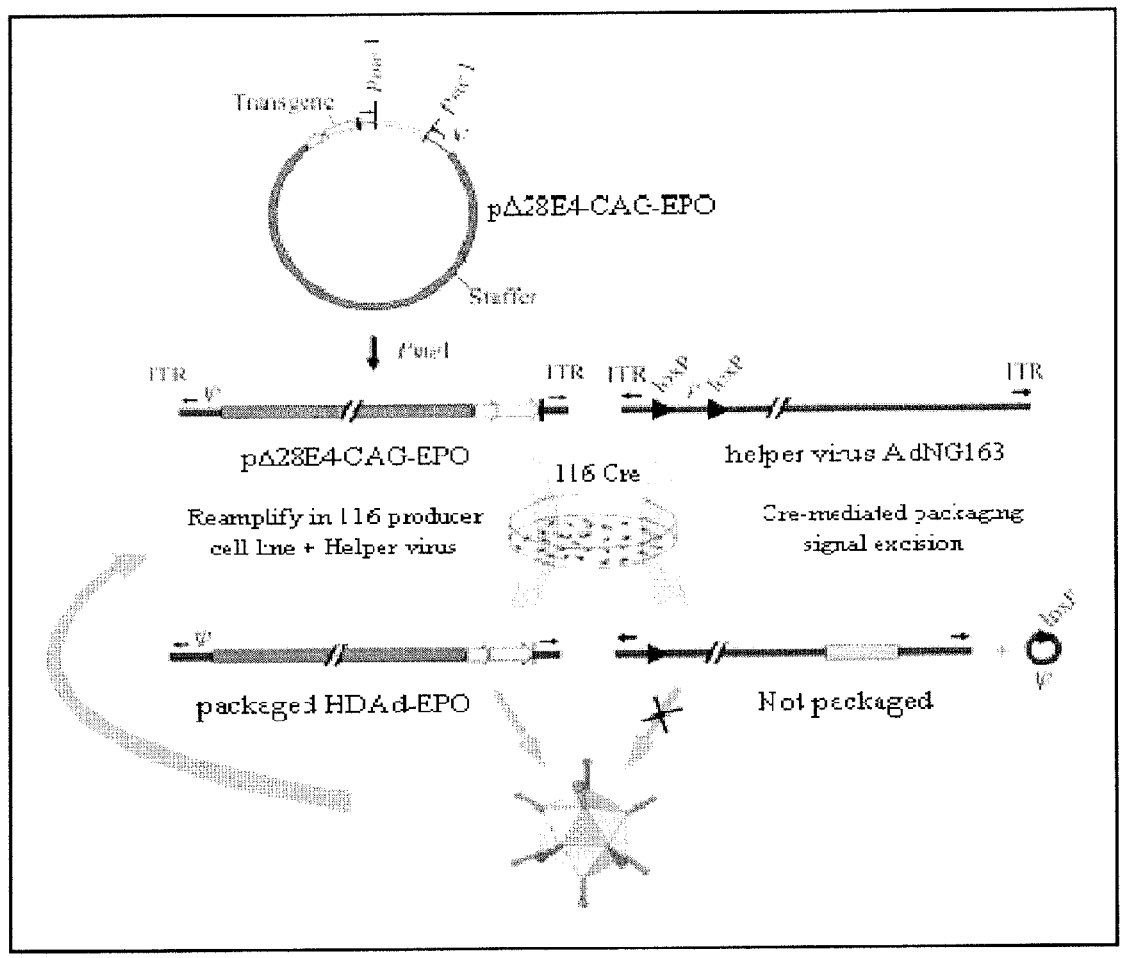
FIG. 19 illustrates schematically construction/production of the HDAd-EPO vector.

The construction of HDAd-EPO vector was as follows: In order to produce the HDAd-CAG-EPO (size 29.9 kb), the pΔ28E4-CAG-EPO plasmid was cut with the PmeI restriction enzyme and the linearized vector was transfected into the 116 Cre-expressing producer cell line (see schematic of FIG. 19). When the plasmid is linearized, the bacterial sequences were removed. The HDAd-EPO was then rescued by infecting the cells with the helper virus AdNG163 containing a loxP-flanked packaging signal, which results in the excision of the viral packaging signal, rendering the helper virus DNA un-packagable (Cre-mediated recombination between the two loxP sites of the HV results in ψ excision, rendering the helper virus genome un-packagable). However, the helper virus will still provide all of the trans-acting factors necessary for replication and packaging of pΔ28E4-CAG-EPO, which contains the appropriate cis-acting elements [i.e., viral packaging signal (ψ) and inverted terminal repeats (ITR)]. The titer of the HDAd was increased by serial co-infections (called passages) of 116 cells with the HDAd and the helper virus.

The non-replicating HDAd-EPO vector, is a key material used for the tissue processing, but was not directly administered to the subject. The HDAd-EPO vector was produced in two stages:

1. Starting from the HDAd-EPO, whose derivation was detailed above, further vector batches are manufactured using the following steps: Amplification, in which the quantity of HDAd-EPO was increased by serial co-infections (passages) of the 116 producer cells with the HDAd-EPO and the helper virus.

2. Large-scale production to generate large quantities of HDAd-EPO.

The HDAd vector was produced by co-infection of the 116 cells with AdNG163Helper Virus and HDAd-EPO vector in 10-layer Cell Factories. After a growth period with one media exchange, the 116 cells were harvested by centrifugation, lysed by 3 freeze/thaw cycles, and DNA/RNA was digested with use of benzonase. HDAd-EPO viral particles were separated from the Helper virus particles and other host cell components by use of a CsCl gradient followed by two CsCl isopyenic runs.

The HDAd-EPO vector produced was analyzed, the results of which are presented in Table 2 below:

TABLE 2

| Test | Protocol Number | Specifications | Results |
|---|---|---|---|
| Safety | | | |
| Mycoplasma Detection | 30200 Direct | Negative | Negative |
| | 30200 Indirect | Negative | Inconclusive on harvest; Negative on final filled vials |
| Biologics-Sterility Test, Immersion, USP/ 21 CFR 610.12 | 30744 30744A | No Growth | Negative (no growth) |
| Biologics-Sterility Test (Bacteriostasis/Fungistasis), Immersion, USP/21 CFR 610.12 | 30736 | No Inhibition | PASS (no Inhibition) |
| Bacterial Endotoxin Test | 37653 | <5 EU/mL | <0.500 EU/mL |
| In vitro Assay for Adventitious Viral Contamination: MRC-5, VERO and Hs68 Cells (Extended Duration) | 30521 | No evidence of viral contamination | No evidence of viral contamination |
| In vivo Assay for Viral Contamination (USFDA) Inculation of Embryonated Hen Eggs, adult and Newborn Mice | 30027 | No evidence of viral contamination | No evidence of viral contamination |
| Detection of Human Parovirus B19 DNA by Quantitative Polymerase Chain Reaction (qPCR): GLP | 30761 | Negative | Negative |

TABLE 2-continued

| Test | Protocol Number | Specifications | Results |
|---|---|---|---|
| Detection of Human Cytomegalovirus (CMV) DNA by Quantitative Polymerase Chain Reaction (qPCR): GLP | 30705 | Negative | Negative |
| Detection of Human Epstein-Barr Virus (EBV) DNA Quantitative Polymerase Chain Reaction (qPCR): GLP | 30713 | Negative | Negative |
| Detection of Simian Virus 40 (SV40) by DNA by Quantitative Polymerase Chain Reaction (qPCR): (GLP) | 30715 | Negative | Negative |
| Detection of Human T-cell Lymphotropic Virus 1 and 2 (HTLV-1 and -2) RNA by Reverse Transcriptase Quantitative Polymerase Chain Reaction (RT-qPCR): (GLP) | 30985 | Negative | Negative |
| Detection of Human Herpesvirus 6, Variant A (HHV-6 A) and Human Herpesvirus 6, Variant B (HHV-6 B) DNA by Quantitative Polymerase Chain Reaction (qPCR): (GLP) | 30863 | Negative | Negative |
| Detection of Human Herpesvirus 7 DNA by Quantitative polymerase Chain Reaction (qPCR): (GLP) | 30361 | Negative | Negative |
| Detection of Human Herpesvirus 8 DNA by Quantitative polymerase Chain Reaction (qPCR): (GLP) | 30913 | Negative | Negative |
| Detection of Hepatitis B Virus (HBV) DNA by Quantitative Polymerase Chain Reaction (qPCR): (GLP) | 30703 | Negative | Negative |
| Detection of HIV-1 RNA by Reverse Transcriptase Polymerase Transcriptase Quantitative polymerase Chain Reaction (RT-qPCR): GLP | 30635 | Negative | Negative |
| Detection of HIV-2 RNA by Reverse Transcriptase-Polymerase Chain Reaction (RT-qPCR): LightCycler Amplification and Fluorescence Probe Hybridiztion (GLP) | 30770 | Negative | Negative |
| Detection of Human Hepatitis C Virus (HCV) RNA by Reverse Transcriptase Quantitative polymerase Chain Reaction (RT-qPCR): (GLP) | 30730 | Negative | Negative |
| Detection of Human adeno-Associated Virus Type 1, 2, 3, 4, 6, 7, 8, 10, 11 (AAV-Pan) DNA by Quantitative Polymerase Chain Reaction (qPCR): GLP | 30415 | Negative | Negative |
| Detection of Adventitious Bovine Viruses: Extended Screening for Non-Bovine Cell Lines Growth in Bovine Serum or Products | 30236 | Negative | Negative |
| Detection of Adventitious Porcine Viruses by 9 CFR Regulations: GLP | 30674 | Negative | Negative |
| Detection of Hepatitis A Virus (HAV) RNA by RT-qPCR | 30665 | Negative | Negative |
| Purity | | | |
| Detection of RCA | 30698 | <1 VP in 3 × $10^{10}$ vp | 0 VP in 3 × $10^{10}$ vp |
| % Helper virus in HD-Ad-CAG-EPO final vialed product by qPCR (R & D) | 39283 | <0.5%* | 0.013% |
| Residual Host cell DNA by TaqMan Technology: GLP | 30699 | <10 ng/150 μl | <50 pg per 150 μl |
| Residual for 3 Amplicons Using Taqman Technology: GLP | 30369 | <10 ng/150 μl | PASS: 1523.58 pg DNA per 150 μl for the 102 bp amplicon. PASS: 706.68 pg DNA per 150 μl for the 401 bp amplicon. PASS: 623.75 pg DNA per 150 μl for the 765 bp amplicon. |
| Immunoenzymetric assay for the Determination of HEK 293 Host Cell Proteins | 38068 | Report | PASS: <1 ng/ml of residual HEK HCP, below the limit of the assay |
| Immunological Detection of Benzonase Endonuclease | 38067 | Report | PASS: <1.25 ng/ml of Benzonase ® endonuclease, below the limit of the assay |

TABLE 2-continued

| Test | Protocol Number | Specifications | Results |
|---|---|---|---|
| Fluorescent Polymerase Chain Reaction (PCR) - based reverse transcription (F-PBRT) assay: (GLP) Strength | 30357 | Negative | Negative |
| Adenovirus Particle Number by HPLC Identity and Potency/Activity | 30783 | Report | PASS: >1.4 × 10^12 VP/ml |
| DNA Sequencing | 30903 | Report | Confirmed as anticipated |
| Gene Expression | | Protein expression following in vitro transduction | >200 IU/bp/day In house tests show 700 IU/BP/day on average |
| Other | | | |
| Determination of pH and Appearance (GMP) | 38026 | Clear, colorless | Clear, colorless solution. No visible particulates present. |

HDAd Vector Stability

In order to check vector stability, vector was aliquoted and stored at −80° C. for 17 months. At different time-points, one aliquot was thawed and 4 micro-organs (freshly harvested from human tummy tuck slabs) were transduced with the same protocol and the same vector titer used to produce genetically modified micro-organs. EPO production per day was assessed during a period of 12-17 days post transduction for potency assessment of the HDAd vector. In a retrospective analysis, the range of EPO secretion per day (average of the 4 Biopumps on days 12-17) was reviewed for each such experiment and they were grouped by the number of months since the preparation of the frozen aliquots: 1-2 months, 6-9 months, and 15-17 months post-aliquoting. The results are summarized in Table 3 below.

TABLE 3

HDAd-EPO lot#1 Test groups of 4 Biopumps were transduced with 3.4 × 10^10 VP per BP, and EPO production measured days 12-17

| Post-production time of experiments: time from vector production in months. | Number of experiments in group | Avg IU/BP/day Highest obtained | Lowest obtained |
|---|---|---|---|
| Months 1-2 | 7 | 721.6 | 214.5 |
| Months 6-9 | 9 | 634.3 | 246.2 |
| Months 15-17 | 2 | 1201.7 | 355.4 |

Results from the table above suggested that there was no evidence of reduced potency in genetically modified micro-organs prepared 15-17 months after production of the vector.

Transduction Efficiency

Figure 22:
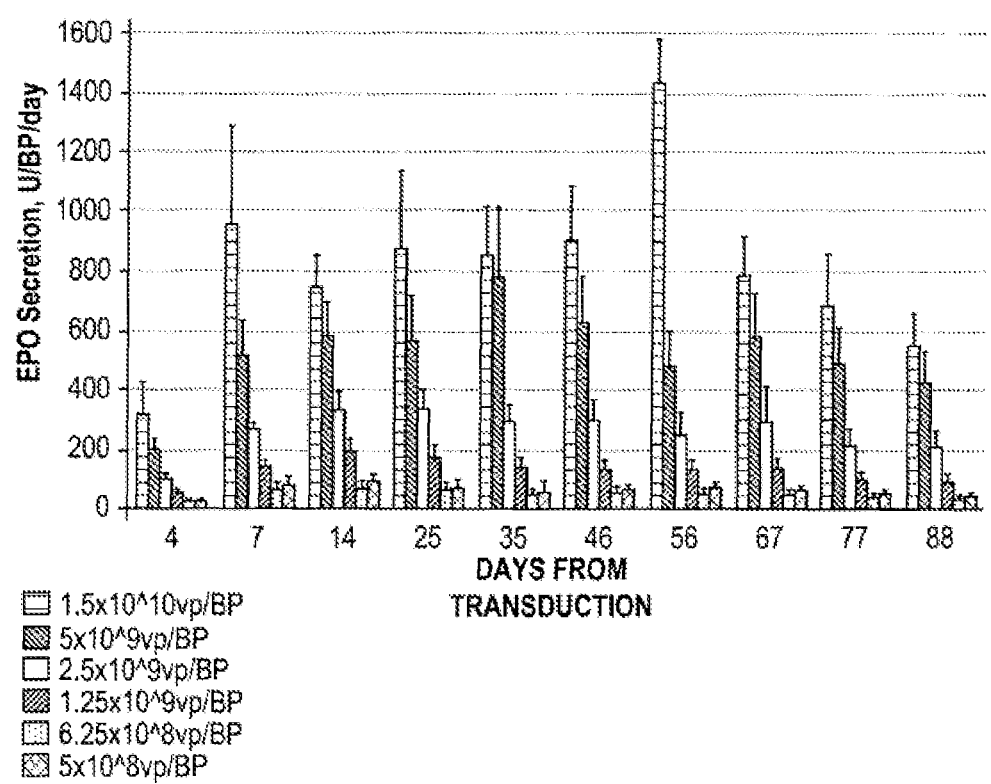
FIG. 22 presents dermal GMMO-EPO titration analysis.

The transduction efficiency with the HDAd-EPO vector is presented in FIG. 22. FIG. 22 illustrates that increasing the virus particle titer in the transduction solution, causes an increase in EPO secretion from the genetically modified micro-organs. Note that when titer was doubled from $1.25 \times 10^9$ to $2.50 \times 10^9$, and then again to $5.00 \times 10^9$, the EPO concentration in the media also proportionally doubled. This increase probably relates to an increase in the number of cells transduced or to an increase in the copy number of VP per cell, indicating improved transduction efficiency. When VP titer was increased above $1.5 \times 10^{10}$ per Biopump, no significant increase in EPO secretion was detected (data not shown), suggesting that the system under the current conditions is close to optimal.

Ex Vivo Micro-Organ Maintenance

Every 3-4 days, used production media was collected, and the level of the secreted recombinant protein and glucose level were assessed along with the viability of the biopumps. Fresh Production media was added to the 24-well plate.

Secreted Protein Measurements

Human EPO (hEPO) and IFNα concentration and secretion levels were assayed using an enzyme-linked immunosorbent assay (ELISA) kit (Quantikine human erythropoietin; R&D Systems; Human interferon alpha ELISA kit, PBL Biomedical Laboratories), according to the manufacturer's instructions.

Figure 20:
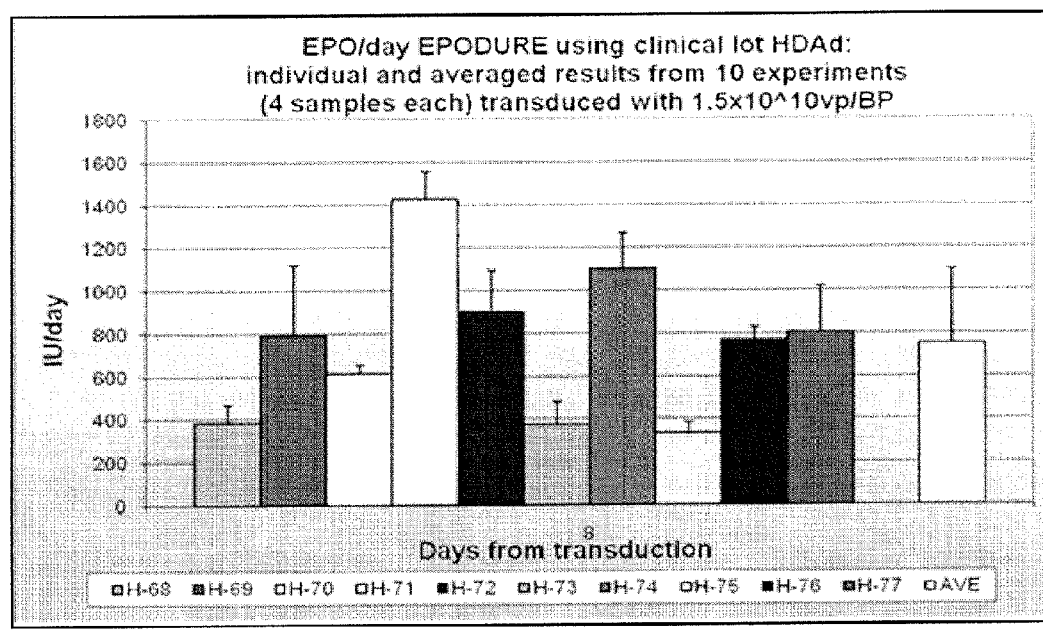
FIG. 20 presents EPO secretion ex vivo from transduced micro-organs obtained from different subjects.

In general, use of a genetically modified dermal micro-organ expressing and secreting EPO required that measurements 8-10 days after transduction of a group of 10 transduced dermal micro-organs, showed secretion levels exceeding 200 U/BP/day. FIG. 20 represents the results of a test for EPO daily production from skins of different donors on day 8 after transduction, all of which secrete in excess of the threshold value of 200 U/BP/day.

Glucose Measurements

Glucose metabolism is used as a non-destructive assay to determine in vitro genetically modified micro-organ viability. Tissue glucose consumption was evaluated using either Sigma-Aldrich Corporation's GAGO20 Glucose (GO) Assay Kit, according to manufacturer's instructions and/or a Glucose Meter (Accu-Check Sensor/Performa, Roche or equivalent).

Hematocrit Measurements

Hematocrit levels were assayed using centrifugation using the reference method recommended by The National Committee for Clinical Laboratory Standards (NCCLS), as is known in the art. To determine the hematocrit, whole blood in a tube was centrifuged at 10-15,000×g for 5 minutes to pellet the red cells (called packed erythrocytes), and the ratio of the column of packed erythrocytes to the total length of the sample in the capillary tube was measured with a graphic reading device within 10 minutes of centrifugation.

Hemoglobin Measurements

Hb concentration levels were measured as part of over all laboratory hematology assessments, which measured Hb, hematocrit, leukocytes, erythrocytes, MCV, MCH, reticulocyte, and platelet count. For instance, an automated Seimens ADVIA platform may be used to measure the Complete Blood Counts. Hb was evaluated by two methods, a standard cyan methemoglobin colorimetric method and flow cytometry.

Micro-Organ Implantation-SCID

In some experiments, genetically modified or control micro-organs were implanted subcutaneously in Severe Combined ImmunoDeficiency (SCID) mice after assaying tissue glucose consumption to ascertain that micro-organs were viable. Male and female SCID mice weighing around 25 grams were anaesthetized with 140 µl of diluted Ketaset (ketamine HCl) (400 µl Ketaset and 600 µl saline) and control or EPO-expressing micro-organs were implanted subcutaneously ten days following micro-organ transduction.

Micro-Organ Implantation-Human

During the clinical trials, genetically modified or control micro-organs were implanted subcutaneously or intradermally under local anesthesia in the lower abdomen, abdominal wall or the upper or lower back of the same human patients from which they were derived, after a patient screening period which included signing the informed consent, laboratory tests, medical history, physical examination, ECG, and concomitant medication documentation. In the results shown herein for the human clinical trials, day "0" is the day of implantation. In addition, GMMO and control micro-organs were assayed for tissue glucose consumption to ascertain that micro-organs were viable. Control or EPO-expressing micro-organs were implanted subcutaneously or intradermally.

Example 1

EPO and IFNα Levels Produced In Vitro by GMMOs

Micro-organs were prepared as described above and transduced with a helper-dependent adenoviral vector expressing an optimized IFNα gene linked to a CAG promoter, as described above. GMMOs were then maintained in culture, and the levels of IFNα produced were evaluated by ELISA. Optimized IFNα-expressing micro-organs produced greater than 1000 ng/day of IFNα in vitro (FIG. 1) for at least 40 days post-harvesting, and recombinant hEPO-expressing micro-organs produced greater than 1000 ng/day of hEPO in vitro (FIGS. 2A-B) for at least 142 days post-harvesting.

Figure 5:
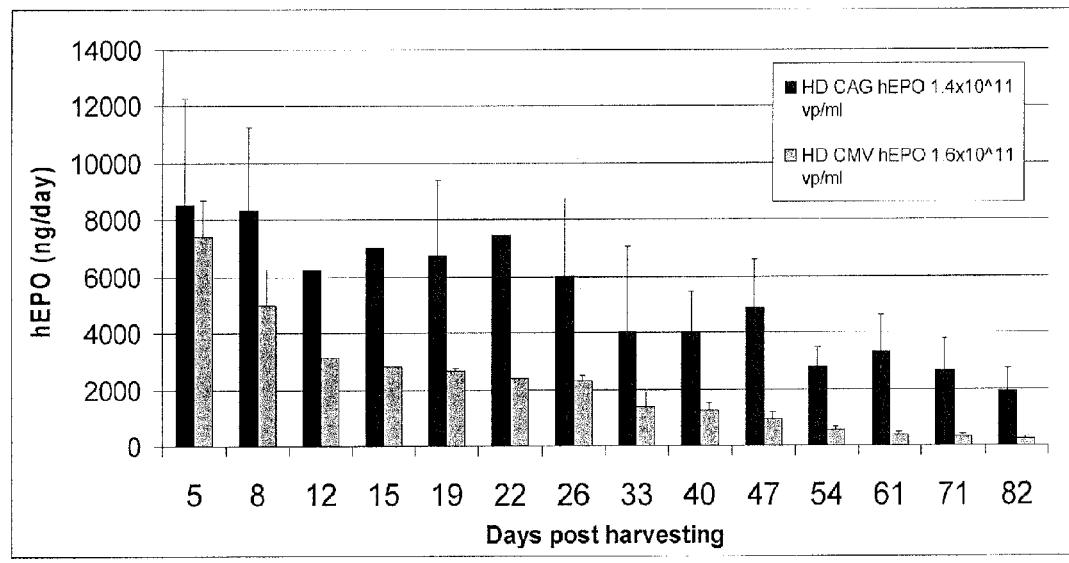
FIG. 5 presents erythropoietin (EPO) expression levels in vitro from formulations comprising EPO-expressing gutless adenovirus downstream of a CAG or CMV promoter.

GMMOs comprising a gutless adenovirus vector encoding optimized hEPO maintained higher percentages of peak expression for more than 200 days compared to micro-organs comprising an adenovirus-5 vector encoding hEPO (FIG. 3). Micro-organs comprising a gutless adenovirus vector encoding optimized hEPO also maintained a higher percentage of peak expression for a longer period of time than micro-organs comprising a gutless adenovirus vector encoding non-optimized hEPO (FIG. 4). Finally, micro-organs comprising a gutless adenovirus vector encoding hEPO downstream of a CAG promoter showed higher levels of hEPO expression, which grew more pronounced as a function of post-transduction day, compared to micro-organs comprising a gutless adenovirus vector encoding hEPO downstream of a CMV promoter (FIG. 5).

Example 2

Figure 6A:
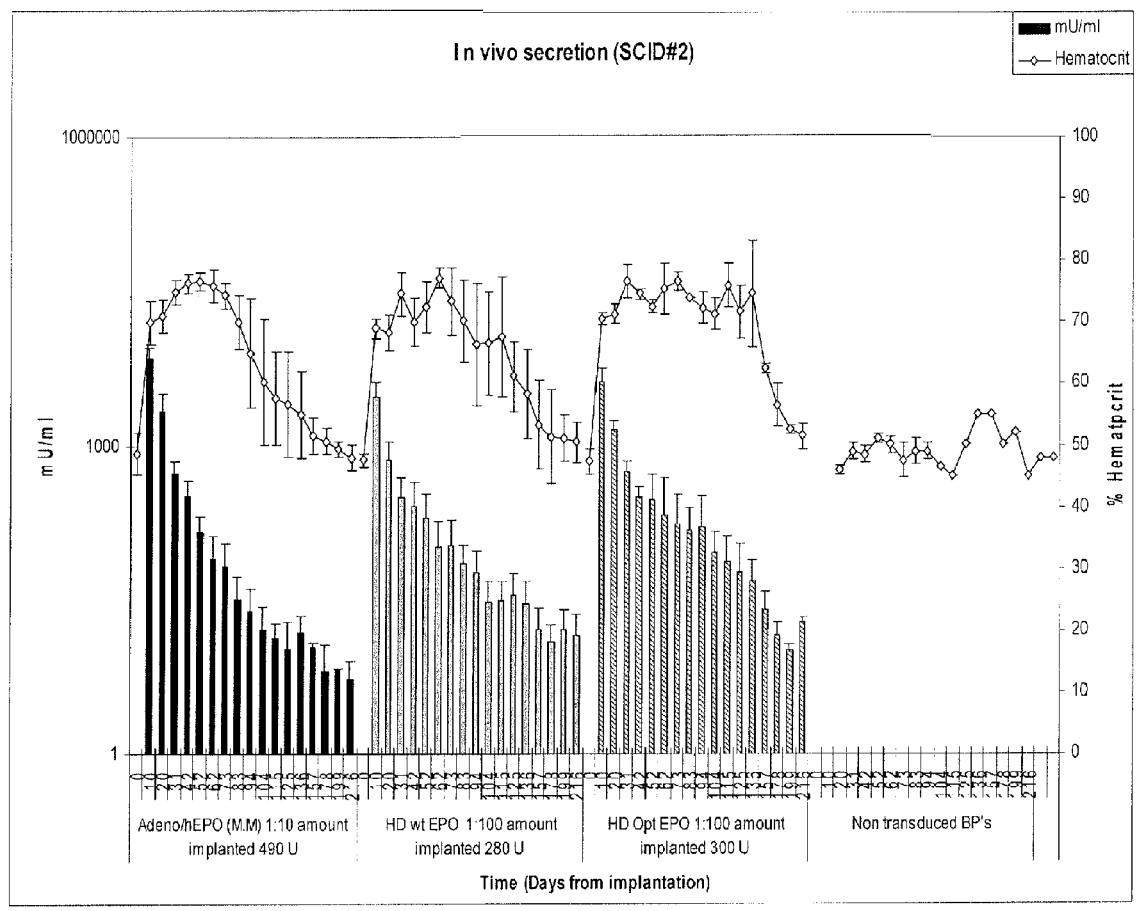
FIG. 6 presents levels of recombinant human erythropoietin produced in vivo in SCID mice (A) and in vitro (B) by the formulations of the instant invention in vitro and the associated changes in hematocrit (A). Ten mice/group were implanted subcutaneously with GMMOs. The hEPO levels (mU/ml) and the corresponding % hematocrit that were measured in the serum of mice that were implanted with GMMOs transduced with adenovirus-hEPO, helper-dependent adenovirus-hEPO, and helper-dependent adenovirus-optimized hEPO and with non-transduced GMMOs are presented. Bleeds were done every 10 days (A). Hematocrit was measured by the centrifugation method and serum hEPO levels in the blood were measured by a hEPO ELISA kit. Non-implanted GMMOs were maintained in culture and levels of EPO were measured (B).
Figure 6B:
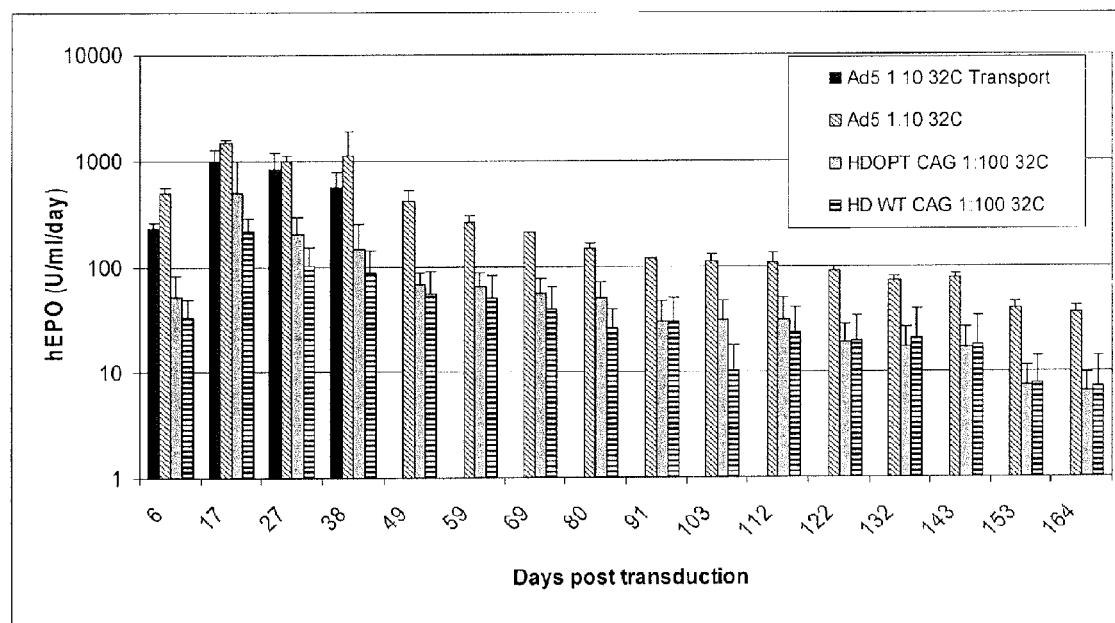

EPO Levels Produced by Human EPO-Expressing GMMOs Maintained In Vitro and in Serum of Implanted SCID Mice EPO-expressing micro-organs were prepared as described above. After a total of nine days in culture, the amount of EPO produced per micro-organ was measured, and this value was used to determine that each mouse was implanted with micro-organs expressing equivalent levels of EPO. On the tenth day, two micro-organs were implanted subcutaneously into each SCID mouse and on the first measurement taken after ten days, levels of hEPO measured in the serum of the SCID mice were significantly above baseline levels. The levels remained high at least 216 days post-implantation and significantly raised hematocrit levels in SCID mice for at least 157 days (FIG. 6A). Non-implanted EPO-expressing micro-organs produced from the same donor at the same time as the implanted EPO-expressing micro-organs but maintained in vitro continuously maintained high levels of EPO production (FIG. 6B). Micro-organs transduced with vectors comprising optimized hEPO gene produced higher levels of EPO than those transduced with recombinant hEPO gene both in vivo (FIG. 6A) and in vitro (FIG. 6B). Control SCID mice implanted with non-EPO-producing micro-organs showed no increase of serum EPO levels and no significant changes in hematocrit levels after micro-organ implantation compared to pre-implantation (FIG. 6A). Micro-organs comprising EPO-expressing adenovirus-5, which was used as a positive control, was used at a titer of 1:10 compared to a titer of 1:100 for micro-organs comprising EPO-expressing optimized or non-optimized gutless adenovirus.

Example 3

Increased Hemoglobin (Hb) Levels Produced by Implanting Human EPO-Expressing

GMMO—Human Clinical Trials—

Clinical Studies Overview

The clinical studies below enlisted anemic, pre-dialysis chronic kidney disease (CKD stage 3-4) patients The CKD stage is based on MDRD-GER [Modification of Diet in Renal Disease (MDRD) Study equation for estimating Glomerular Filtration Rate (GFR) from serum creatinine]. Patients participating were not iron deficient using measurements of transferrin saturation % (TSAT %) and ferritin (ng/ml) as criteria. Patients were either naïve with respect to EPO-dependency or if EPO-dependent, they are withdrawn from erythropoiesis stimulating agents (ESA) for a period of at least 4 weeks. The term "patient" as used herein may also be referred to herein as a "subject".

Figure 11A:
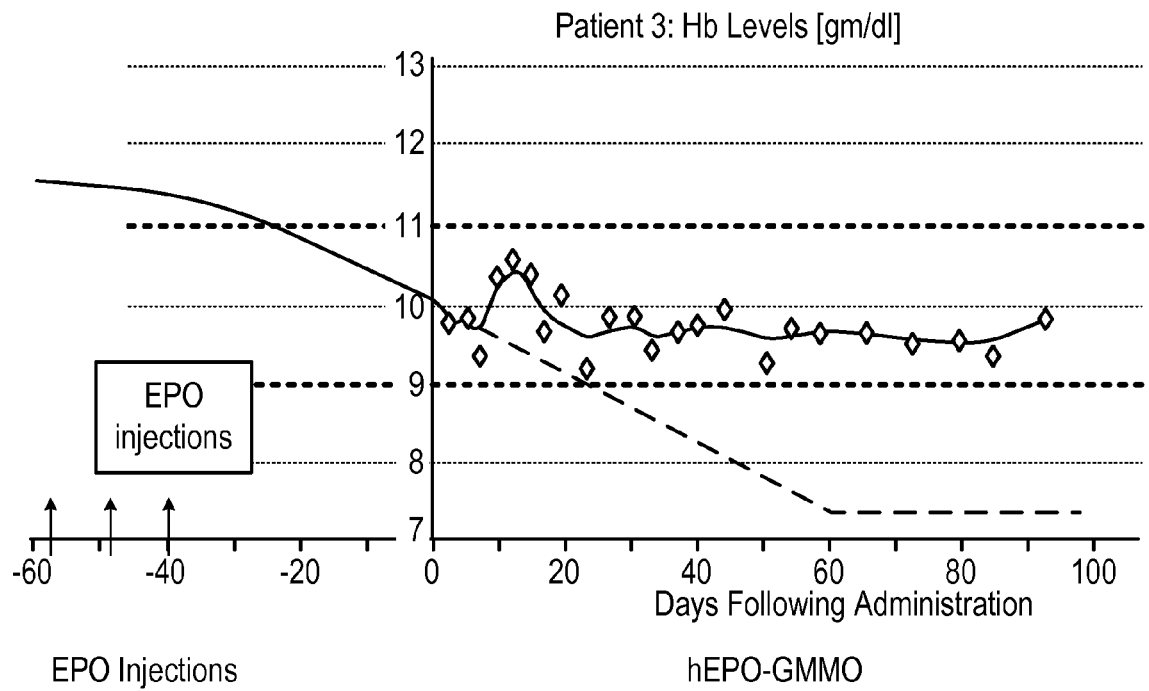
FIG. 11A presents hemoglobin response of Patient 3.
Figure 11B:
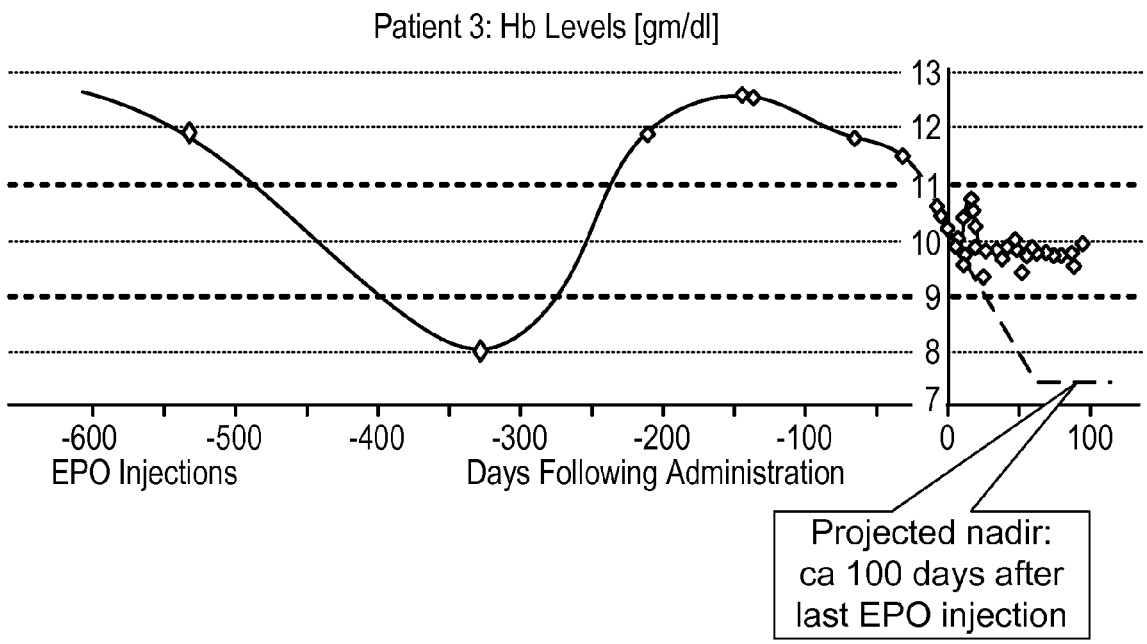
FIG. 11B presents hemoglobin levels prior to hEPO-GMMO implantation with the projected nadir.

For determination of Hb baseline, a baseline Hb average of values was determined from the previous 30 days in naïve participants or baseline was determined from the projected nadir 100 days post last ESA injection and if available compared to historical Hb values. FIGS. 11A and 11B show Hb values prior to implantation and the projected nadir. Hb values after implantation are also shown. Basal measurements: RBC count, Hb, Hct (%), absolute reticulocytes count, serum EPO level (mU/ml), iron status on day −30, day −9, and the day of implantation (day 0) were collected.

Assessment of efficacy was performed by measuring EPO levels, Hb and hematocrit, and taking reticulocytes counts three times per week for the first 2 weeks, thereafter twice per week until the sixth week, and once weekly thereafter. Criteria for assessment included Hb response and duration of effect.

Figures 14, 15:
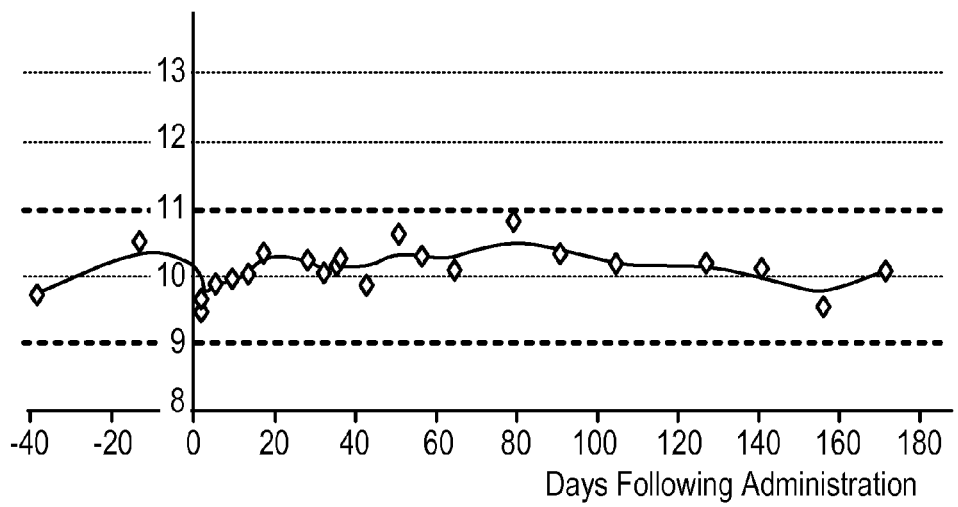
FIG. 14 presents sustained hemoglobin response of Patient 7.
FIG. 15 presents base-line demographics of clinical study patients.

FIG. 15 presents Demographic data for participants in the studies described below.

Safety results of the clinical trials support the advantages of use of genetically modified micro-organs in a clinical setting. Specifically, safety results showed: (a) no adverse events in any patients treated; (b) the procedure was brief and well tolerated; (c) no evidence of anti-EPO antibody formation (blood samples were tested prior to, during, and after treatment and no increase in EPO antibodies was observed as a result of treatment); and (d) no serum EPO levels to date exceeded 60 mU/ml.

Clinical Trial—Single Administration

Phase I clinical trials were performed in Israel, in which pre-dialysis anemic patients with chronic kidney disease (CKD), stage III and stage IV, were implanted with autologous hEPO-GMMOs of the sustained type (a long-lasting therapeutic formulation) of the present invention. A single implantation treatment with GMMO-hEPO provided between 3 to greater than 16 months of effective EPO therapy. Approval for the Phase I/II GMMO hEPO trial was approved by Israel's Ministry of Health and was conducted at the Hadassah Medical Center and the Sourasky Tel Aviv Medical Center. The clinical trial was conducted according to regulatory and clinical standards of the FDA, in order to facilitate later US based clinical trials.

Figure 7:
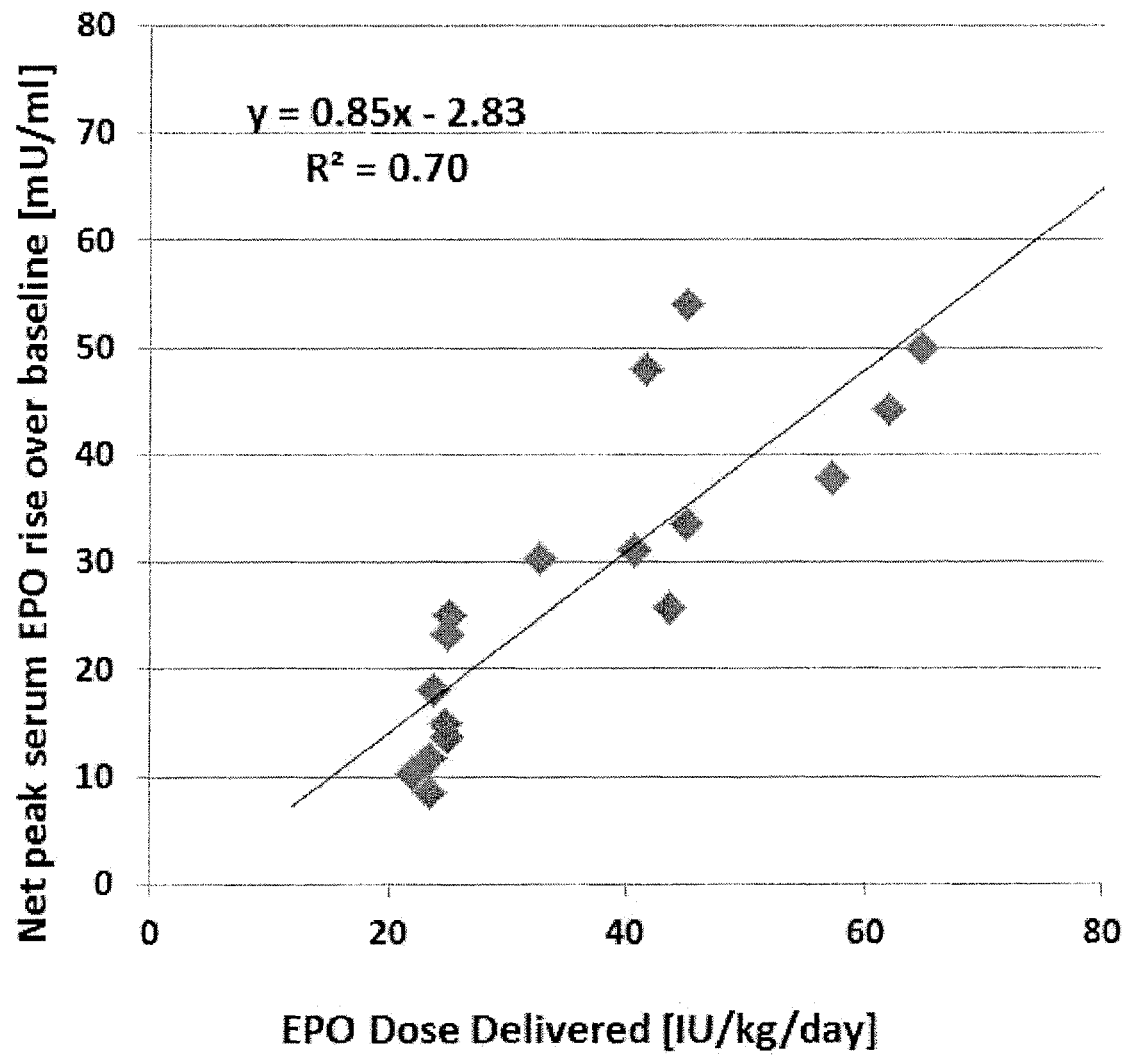
FIG. 7 presents the correlation of peak serum EPO levels to delivered dose in vivo, in human patients.

Patients were treated at 18-25 IU/kg/day (low dose) or at 35-45 IU/kg/day (mid dose) or at 55-65 IU/kg/day (high dose). FIG. 7 shows the correlation of Net Peak serum EPO rise over baseline to the EPO dose administered (IU/kg/day).

Figure 8A:
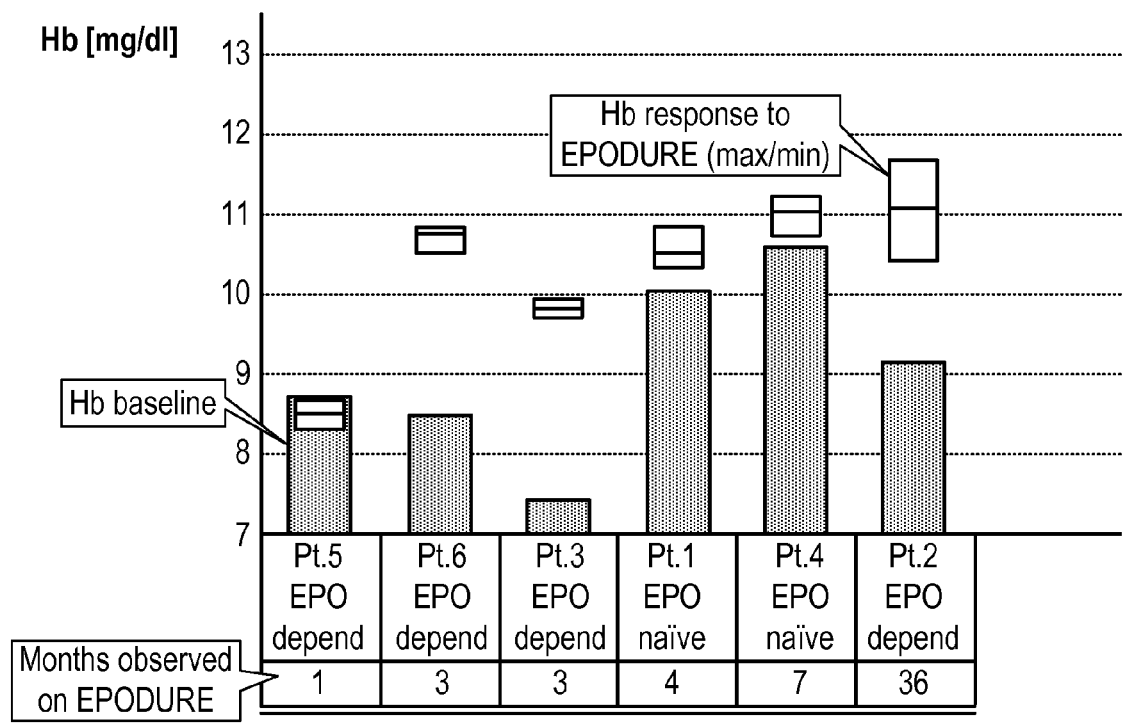
FIG. 8A presents summary results of hEPO-GMMO low dose clinical group, illustrating a sustained hemoglobin response within a therapeutic window (10-12 g/dl) in 5 of 6 patients for periods of 1-36 months without injections.
Figure 8B:
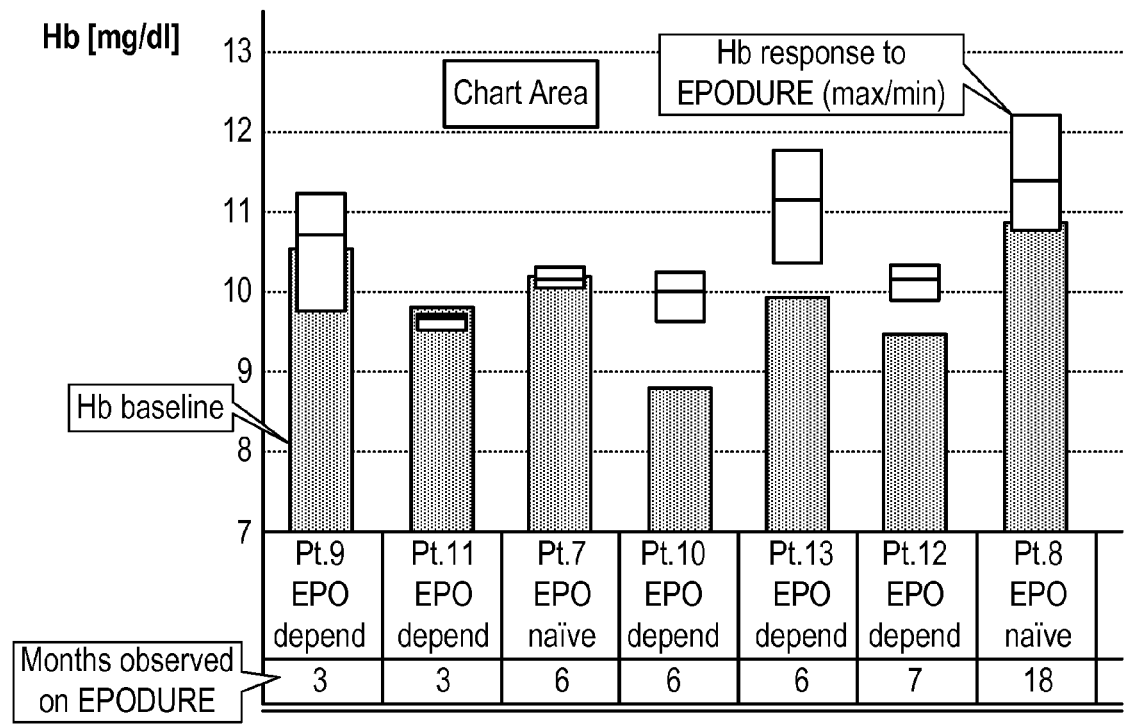
FIG. 8B presents summary results of hEPO-GMMO mid dose clinical group, illustrating a sustained hemoglobin response within the therapeutic window (10-12 g/dl) in 6 of 7 patients, for periods of 3-18 months without injections.
Figure 8C:
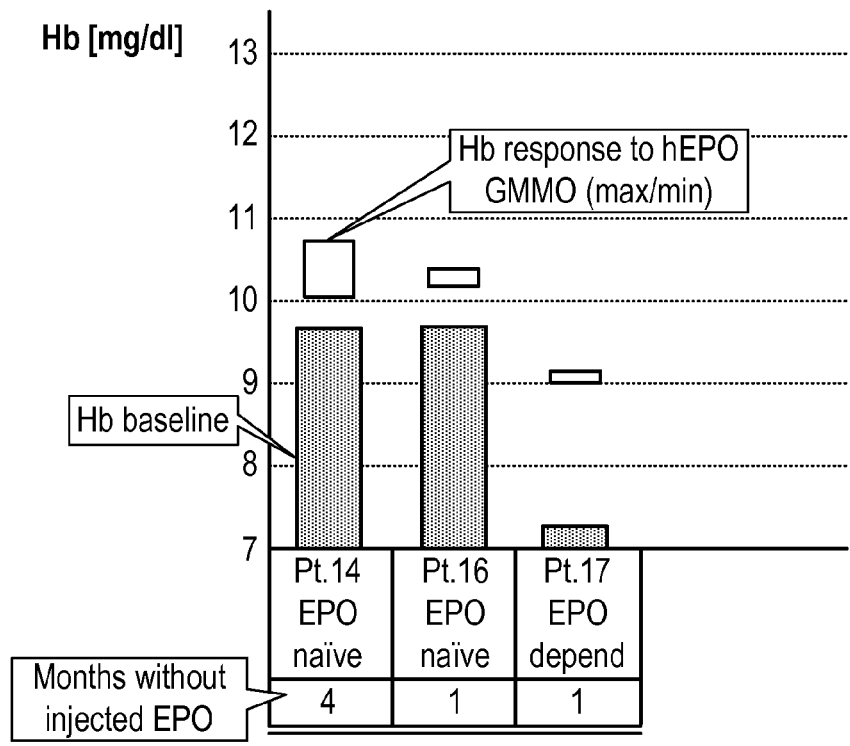
FIG. 8C presents summary results of hEPO-GMMO high dose clinical group, illustrating a sustained hemoglobin response within the therapeutic window (10-12 g/dl) in 3 patients for periods of 1-4 months without injections.

Results showed that Hb levels (Hb) were maintained in the 10-12 g/dl range (therapeutic window) in the majority of patients using low dose administration of 18-25 IU/kg/day, mid dose administration of 35-45 IU/kg/day or high dose administration of 55-65 IU/kg/day. FIGS. 8A, 8B and 8C illustrates that the sustained Hb response within the therapeutic window, persisted for between 1-24 months. This sustained Hb response result is independent of any injections of EPO.

Male and female patients ranging in age from 21-82 were included in the study.

Patient 1 was an EPO naïve patient. Clinical statistics and details of EPO trial for Patient 1 include: 82 year old male; Stage 4 CKD patient; GFR 21 ml/min, adequate iron stores (Transferrin saturation 33%, ferritin 340 ng/ml); and received low EPO dose (18-25 IU/kg/day)—2 hEPO-GMMO administered.

Comments on treatment included: No adverse events; good Hb response; and satisfied with treatment though tired of frequent blood sampling and follow up visits for the study protocol—requested early termination after 4.5 months.

Figure 9:
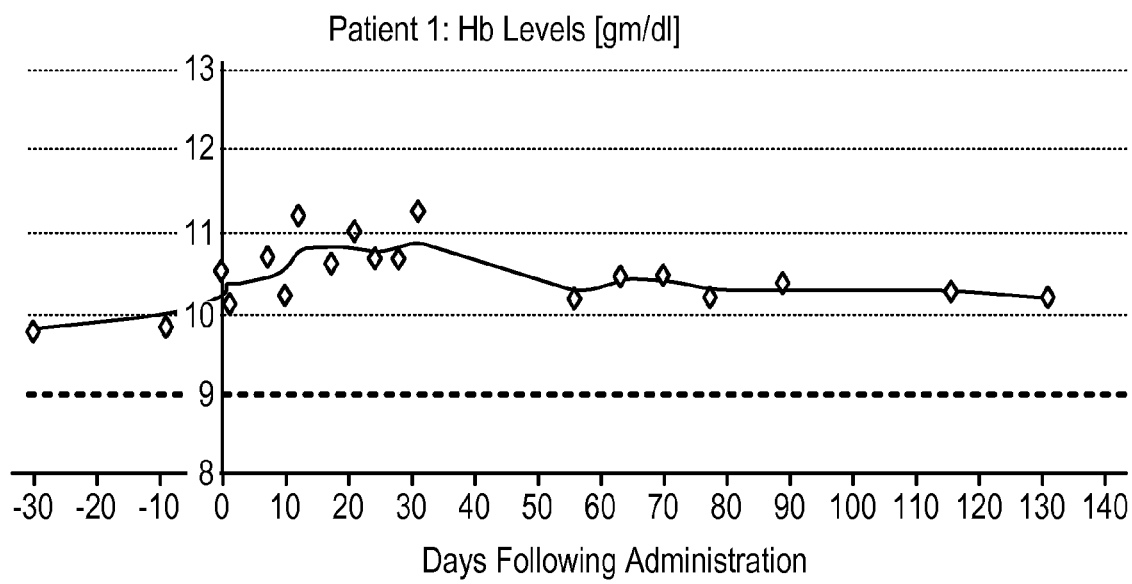
FIG. 9 presents hemoglobin response of Patient 1.

FIG. 9 shows sustained Hb response in patient 1, for a period of 131 days.

Patient 2 was an EPO dependent patient. Clinical statistics and details of EPO trial for Patient 2 include: 71 year old male, Stage 3 CKD patient; EPO dependent for 18 months, received 6000 IU every 10 days, last administered 40 days prior to EPO treatment; GFR 57 ml/min, adequate iron stores (Transferrin saturation 26%, ferritin 105 ng/ml); received low EPO dose (18-25 IU/kg/day)—3 hEPO-GMMOs administered Comments on treatment included: No adverse events; satisfied with treatment; good Hb response; and successfully completed over 12 months of follow-up. Patient is physically active and requests re-enrollment for higher dose after current treatment.

Figure 10A:
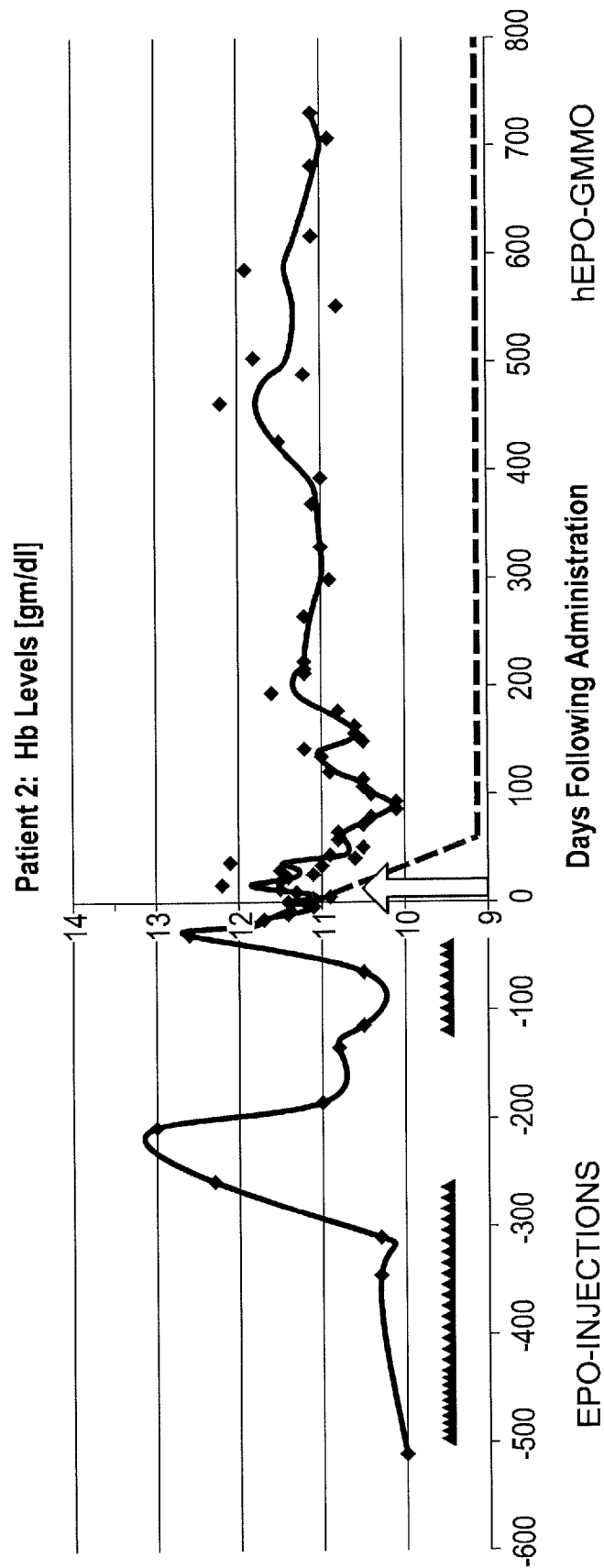
FIG. 10A presents sustained hemoglobin response of Patient 2.
Figure 10B:
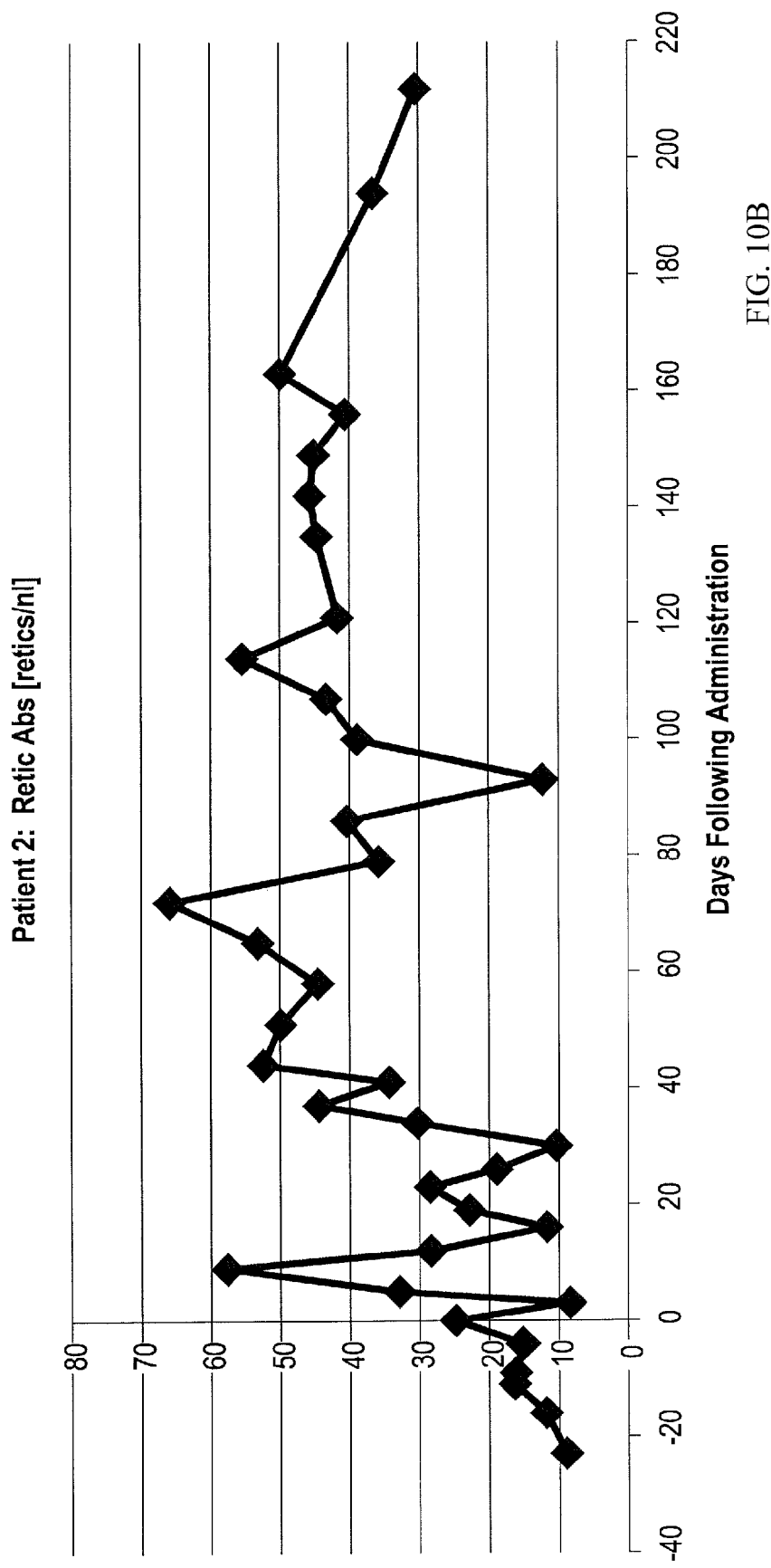
FIG. 10B presents reticulocytes count in response to hEPO-GMMO administration in Patient 2.
Figure 10C:
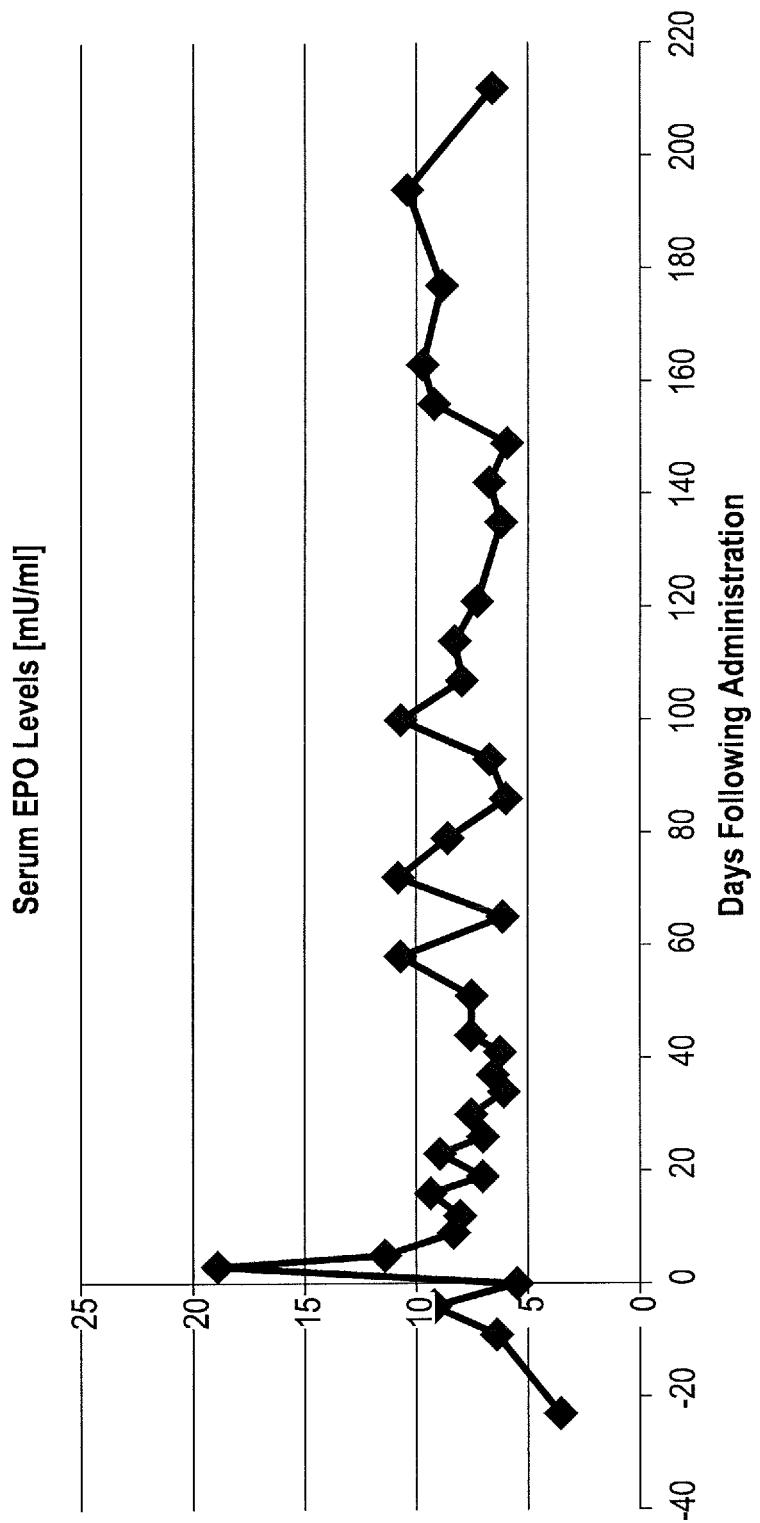
FIG. 10C presents serum EPO levels in response to hEPO-GMMO in Patient 2.

FIG. 10A shows sustained Hb response was maintained within the therapeutic window in patient 2 for two years. FIGS. 10B and 10C show reticulocyte count and serum EPO levels, respectively, over a period of greater than 200 days for patient 2.

Patient 3 was an EPO dependent patient. Clinical statistics and details of EPO trial for Patient 3 include: 58 year old male, Stage 4 CKD patient; EPO dependent for 16 months, received 5000 IU once per week, last administered 39 days prior to EPO treatment; GFR 26 ml/min, adequate iron stores (Transferrin saturation 23%, ferritin 243 ng/ml); and received low EPO dose (18-25 IU/kg/day)—4 hEPO-GMMOs administered Comments on treatment included: No adverse events; good Hb response: elevation of ~2 gm/dl over baseline Hb level. The target level not sustained at current dose. Patient's inclusion in study was terminated to receive supplemental EPO injections.

FIG. 11A shows sustained Hb response was maintained just under the target therapeutic window in patient 3 for 92 days.

Patient 4 was an EPO naïve patient. Clinical statistics and details of EPO trial for Patient 4 include: 57 year old female, Stage 3 CKD patient; EPO naïve; GFR 32 ml/min, adequate iron stores; and received low EPO dose (18-25 IU/kg/day)—5 hEPO-GMMOs administered.

Comments on treatment included: No adverse events and good Hb response.

Figure 12:
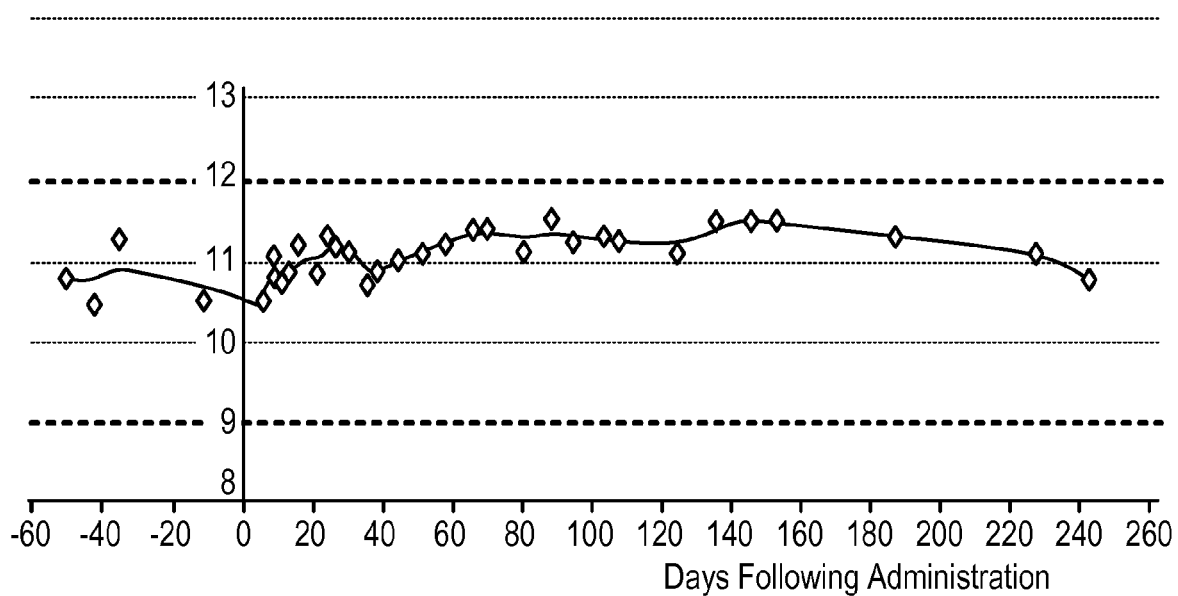
FIG. 12 presents sustained hemoglobin response of Patient 4.

FIG. 12 shows sustained Hb response within the therapeutic window in patient 4, for a period of 224 days.

Patient 5 was an EPO dependent patient. Clinical statistics and details of EPO trial for Patient 5 include: 51 year old female, Stage 4 CKD patient, polycystic kidney disease; EPO dependent, received 60 µg of Aranesp once per 3 weeks, last administered 113 days prior to EPO treatment; GFR 18 ml/min, adequate iron stores (Transferrin saturation 39%, ferritin 371 ng/ml); and received low EPO dose (18-25 IU/kg/day)—6 hEPO-GMMOs administered.

Comments on treatment included: No adverse events; transient Hb response, insufficient; and discontinued from trial on day 35

Patient 6 was an EPO dependent patient. Clinical statistics and details of EPO trial for Patient 6 include: 40 year old female, Stage 4 CKD patient, polycystic kidney disease—candidate for transplant; EPO dependent for 6 weeks, received 2000 IU twice per week, last administered 29 days prior to EPO treatment; GFR 25 ml/min, adequate iron stores (Transferrin saturation 33%); and received low EPO dose (18-25 IU/kg/day)—4 hEPO-GMMOs administered.

Comments on treatment included: No adverse events; good initial Hb response; deterioration in renal function; supplemental EPO injections given. Patient discontinued from study to go on dialysis.

Figure 13:
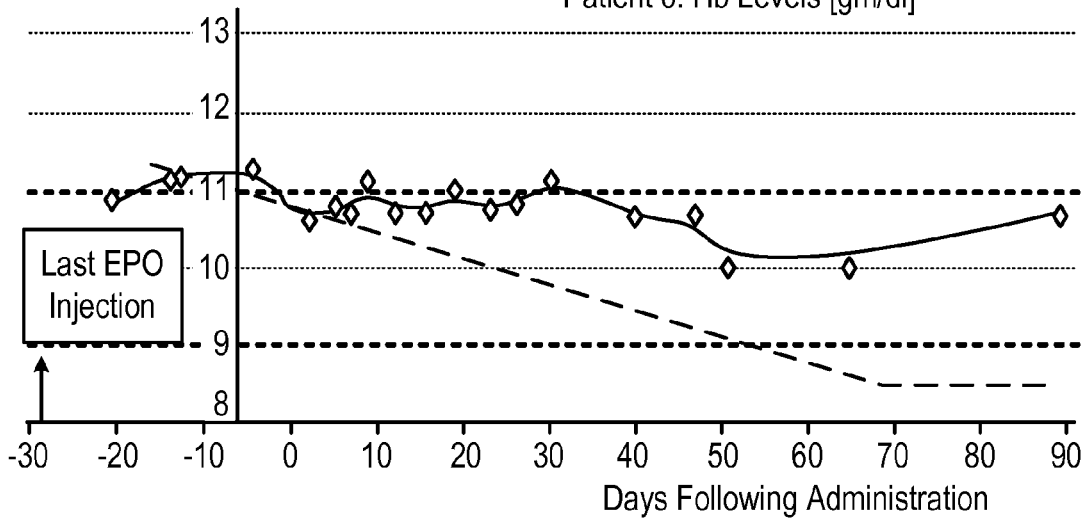
FIG. 13 presents sustained hemoglobin response of Patient 6.

FIG. 13 shows sustained Hb response within the therapeutic window in patient 6, for a period of 89 days.

Patient 7 was an EPO naïve patient. Clinical statistics and details of EPO trial for Patient 7 include: 77 year old male, Stage 4 CKD patient; EPO naïve; GFR 19 ml/min, adequate iron stores; and received medium EPO dose (35-45 IU/kg/day)—8 hEPO-GMMOs administered.

Comments on treatment included: No adverse events and was a low responder.

FIG. 14 shows sustained Hb response mostly within the therapeutic window in patient 7, for a period of 172 days.

Results of this study showed blood of patients receiving low and medium doses of hEPO-GMMOs show sustained Hb levels within the therapeutic window for an extended period of time. Further, patients had no serious, product related adverse events and did not report major discomfort during or after the procedures.

Clinical Trial—Dose Augmented by a Second Administration

Patient 10 was an EPO dependent patient treated with two low-dose administrations. The first administration was at day 0 followed by a second administration at day 70. FIG. 16 illustrates that the first dose sustained elevation of EPO at between 2-5 mU/ml above the baseline of 10 mU/ml and Hb at 10.2 g/dl versus a nadir of 8.8 g/dl. Following the administration of the second dose a similar peak response was observed in EPO serum levels and reticulocytes, with an apparent increase in Hb.

Results with a second administration show that retreatment is feasible, safe and effective.

Safety Results

This study was initiated in August 2008 and has been conducted at two clinical sites. It was a Phase I/II, open label, single center, uncontrolled, dose escalation study, comprising three dosage groups (approximately 20, 40, and 60 EPO IU/kg/day). Table 4 below lists individual demographics, dose, and previous EPO exposure of each of the 17 patients treated through May 8, 2011.

TABLE 4

| Patient | Age, Sex | EPO naïve | Weight [kg] | Target dose [IU/kg/day] | Actual dose [IU/kg/day] | Biopumps implanted |
|---|---|---|---|---|---|---|
| 1 | 82, M | Yes | 84 | 18-25 | 21.4 | 2 |
| 2 | 72, M | No | 75 | 18-25 | 25.0 | 3 |
| 3 | 58, M | No | 84 | 18-25 | 24.7 | 4 |
| 4 | 68, F | Yes | 62 | 18-25 | 23.5 | 5 |
| 5 | 50, F | No | 70 | 18-25 | 24.9 | 6 |
| 6 | 42, F | No | 75 | 18-25 | 23.4 | 4 |
| 7 | 77, M | Yes | 85 | 35-45 | 40.7 | 8 |
| 8 | 48, F | Yes | 62 | 35-45 | 45.1 | 3 |
| 9 | 76, M | No | 67 | 35-45 | 45.0 | 4 |
| 10 (a) | 64, F | No | 88 | 18-25 | 25.2 | 6 |
| 10 (b) | | | | 18-25 | 23.8 | 3 |
| 11 | 70, F | No | 98 | 35-45 | 43.7 | 5 |
| 12 | 21, F | No | 82 | 35-45 | 32.8 | 8 |
| 13 | 52, M | No | 70 | 35-45 | 41.6 | 9 |
| 14 | 52, M | Yes | 53 | 55-65 | 64.7 | 3 |
| 15 | 60, F | No | 84 | — | — | — |
| 16 | 73, F | Yes | 87 | 55-65 | 57.2 | 9 |
| 17 | 69, M | No | 58 | 55-65 | 62.0 | 9 |
| 18 | 44, F | No | 60 | 55-65 | 65.1 | 7 |

The patient procedures of harvesting and implantation have been well tolerated by the patients in the trial, for doses up to 65 U/kg/day. Erythema and edema have been noticed in some of the cases, and subcutaneous hematoma was usually mild, with no observable correlation to the dose. Signs of the local subcutaneous hematoma disappear after approximately two weeks after the procedure. Local pain, reported in some cases, was usually mild and lasted only one day or slightly longer if no analgesic was taken.

Summary

Clinical trials presented show that hEPO-GMMO is safe and treatments are amenable to varying dosages, with feasibility demonstrated at dosages of about 18-25 IU/kg/day, 35-45 IU/kg/day and 55-65 IU/kg/day. Surprisingly, a single administration of an hEPO-GMMO provided a sustained Hb response in the therapeutic window (10-12 g/dl blood Hb) for at least 3 months to more than 24 months for most patients.

Repeat administration had been shown to be safe and efficacious. At the same time, it has been shown here that subcutaneous implantation of an hEPO-GMMO provided a sustained source of EPO for subjects in need thereof. Thus, subcutaneous implantation of hEPO-GMMO is a significant advance in providing an effective sustained treatment alternative to patients in need, compared to months of frequent bolus injections of ESAs.

Example 4

Preclinical Toxicology and Physiological Function Studies in SCID Mice

A Good Laboratory Practice (GLP) toxicology study was performed at Harlan Biotech Israel. The objective of this study was to assess the potential toxic effects of the Test Product Biopump HDAd-hEPO following a single subcutaneous implantation in the NOD-SCID mouse for a maximal exposure period of 12 weeks in respect to its intended use as a constant source for prolonged drug delivery in chronic renal failure disease.

The design of the toxicology study was reviewed in detail and agreed upon with the Head of FDA's Preclinical Division, and implemented accordingly.

In view of the relatively short lifespan of SCID mice (ca 18 mo), the durations presented in Table 5 were judged reasonable for testing toxicological safety to support the proposed clinical trial.

TABLE 5

Experimental Design

| BP Dose | Total # of mice | # sacrificed @ 2 wks | # sacrificed @ 8 wks | # sacrificed @ 12 wks |
|---|---|---|---|---|
| 300-450 IU Epo/day | 30 (15M, 15F) | 5M, 5F | 5M, 5F | 5M, 5F |
| Control - non transduced | 18 (9M, 9F) | 3M, 3F | 3M, 3F | 3M, 3F |
| Control - no micro-organ | 18 (9M, 9F) | 3M, 3F | 3M, 3F | 3M, 3F |

In the first group, each animal received a portion of a Biopump (GMMO) that secreted in the range of 300-450 IU EPO/day.

The second group was an implanted control group, in which each animal received a similar sized portion of a dermal non-transduced micro-organ.

The third group as a "no micro-organ" control group, in which each animal was treated with identical subcutaneous related procedures as in the control group but with no implant Clinical Signs:

Throughout the entire observation period, careful clinical examinations were carried out and recorded for all the animals in the study at least once daily. Observations include changes in skin, fur, eyes, mucous membranes, occurrence of secretions and excretions (e.g. diarrhea) and autonomic activity. Changes in gait, posture and response to handling, as well as the presence of bizarre behavior, tremors, convulsions, sleep and coma were also observed and were recorded.

Body Weights:

Determination of individual body weights of all the animals in the study was carried out at the randomization procedure, followed by body weight determination prior to the single subcutaneous implantation/sham operation, 2 days later and thereafter on a weekly basis.

Food Consumption:

Measurements of food consumption was carried out during the acclimation period, followed by weekly basis measurements throughout the entire observation period for all the animals in the study.

Collection of Blood Samples (Interim Bleeding Sessions):

All animals were subjected to interim bleeding sessions for Hematology & Biochemistry parameters, carried out every 13-15 days from the day of the single subcutaneous implantation. In order to keep the uniformity within the study, all the animals in the study were subjected to the interim bleeding sessions. The blood samples served, among others, for the purpose of measuring the Hematocrit (HCT) levels.

Necropsy Procedures & Macroscopic Examination:

All the animals originally assigned to the potential toxicity assessments were subjected to a full detailed necropsy and gross pathological examination.

Organ/Tissue Collection, Weighing & Fixations:

All the organs/tissues were collected during the respective scheduled necropsy session.

Results:

A test Product-treated female mouse was found dead in its cage on Day 7 of the study. In addition, a Test Product-treated male mouse was found dead on Day 52. No further mortality occurred in any of the Test Product, Control Item or Sham-operated groups (including spares).

No obvious treatment-related reactions were observed among the Test Product, Control Item or Sham-operated surviving animal throughout the entire observation period.

Elevated HCT levels were recorded throughout the entire observation period within the Test Product—treated animals in view of the continuous secretion of hEPO by the Test Product itself. Statistically significant increased (p, 0.05 & p, 0.01) HCT values were revealed within the Test Product—treated group on Days 15, 28, 43, 57 & 70 vs. the respective Sham-Operated mean group values.

In view of the histopathological findings obtained under the conditions of this study, it can be concluded that the Test Product Biopump HDAd-hEPO, subcutaneously implanted in the NOD-SCID mouse as a constant source for prolonged drug delivery at the dose of 300-450 IU/animal/day for a maximal exposure period of 12 weeks, is associated only with pharmacological-related changes, observed in all three scheduled termination time points.

Figure 24:
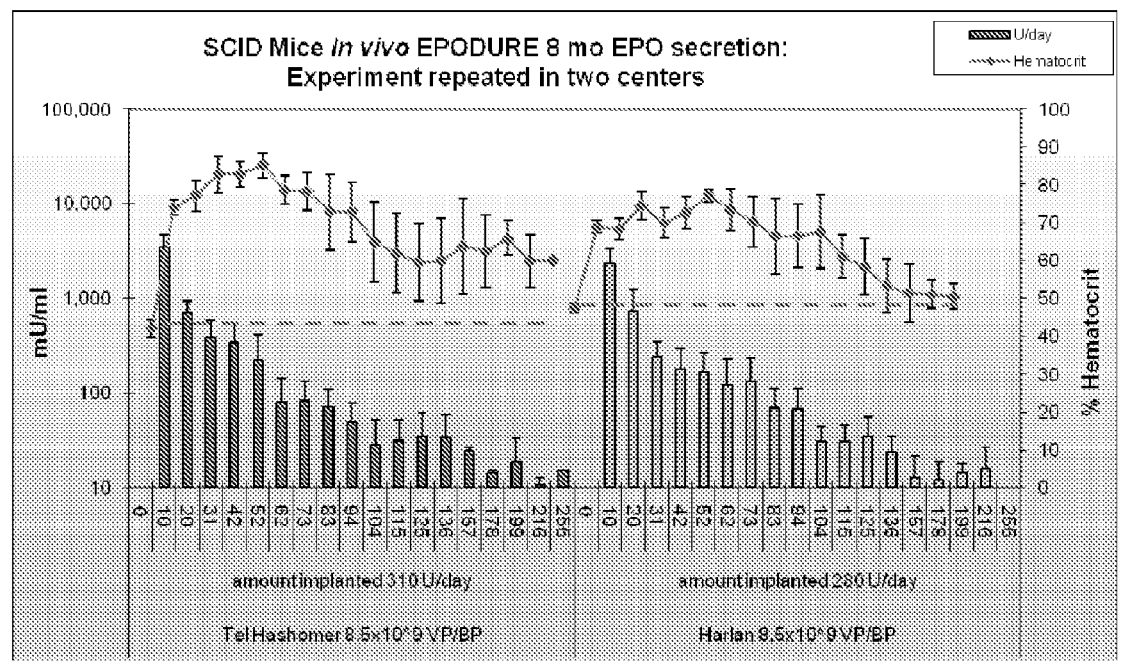
FIG. 24 presents elevated serum EPO and subsequent rise in hematocrit in SCID mice.

Further, long-term erythrostimulatory activities of Biopump HDAd-hEPO in two comparable groups of SCID mice were run in parallel at two well established animal facilities. Four mice of each group were implanted subcutaneously with two Biopump HDAd-hEPO per mouse, secreting a total of approximately 300 IU/day. The mice were bled every 10 days and hematocrit was measured by the centrifugation method and serum EPO levels using a clinical grade EPO ELISA kit (note: EPO levels in the mice serum were measured by an ELISA kit which is specific to human EPO, with no cross-reactivity to mice EPO). As seen in the FIG. 24, elevated serum EPO levels and subsequent rise in hematocrit were found in both experimental groups, which maintained high levels of hematocrit for several months. The control mice did not have elevated serum EPO levels or elevated hematocrit (data not shown).

Overall, these studies showed long-term elevation of serum EPO and elevation of hematocrit for up 8 months, which comprises a significant portion of the typical lifespan of the SCID mice.

Example 5

Long Term Ex Vivo EPO Secretion

Dermal micro-organs were prepared as described above and transduced with a helper-dependent adenoviral vector comprising SEQ ID No. 11 and expressing EPO. The dermal GMMOs were then maintained in culture, and the levels of EPO produced were evaluated by ELISA.

Figure 23:
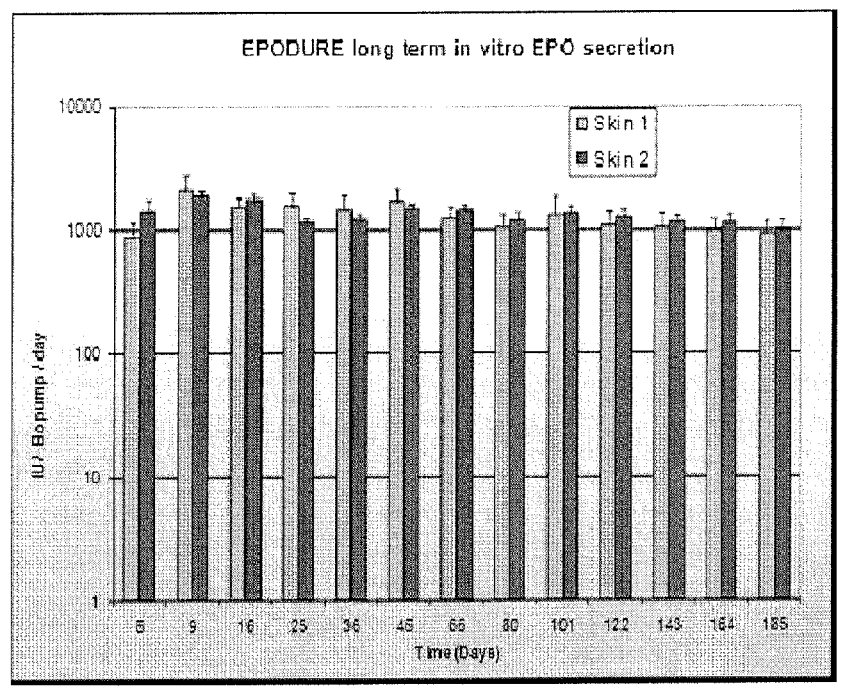
FIG. 23 presents sustained long-lasting in vitro EPO secretion.

Results:

The bar graph presented in FIG. 23 shows long term ex-vivo EPO secretion after transduction. Dermal GMMOs produced from dermis of two different subjects were monitored for over 6 months. In both cases, steady secretion was observed, attesting to the continued presence of the transgene, its structural stability and long-lasting consistent expression of EPO.

Example 6

Preclinical Cell Count and Viability Cell Count Studies

The dermal micro-organ samples were maintained ex-vivo under culture conditions which ensured optimal viability and wherein the dermal micro-organ stays intact throughout the ex-vivo process.

Figure 21:
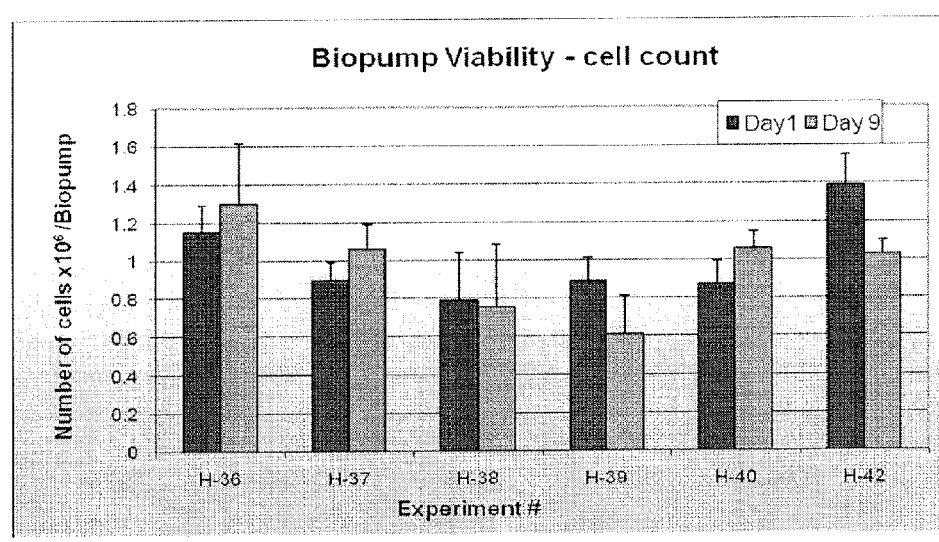
FIG. 21 presents GMMO-EPO viability by cell count at different times during maintenance.

To confirm that dermal micro-organs remain intact and viable and to assess the typical number of cells that can be expected in a genetically modified dermal micro-organ, sample genetically modified dermal micro-organs were broken down into individual cells in order to count the number of viable cells. The genetically modified dermal micro-organs were broken down by collagenase digestion followed by trypan blue staining at day 1 and after 9 days of maintenance. The results showed no significant change in the number of cells during the maintenance period (FIG. 21 and Table 6), with approximately 1 million viable cells in each genetically modified dermal micro-organ.

TABLE 6

| | NUMBER OF CELLS (x10^6)/BIOPUMP | | | | | |
|---|---|---|---|---|---|---|
| Days from transduction | Experiment H-36 | Experiment H-37 | Experiment H-38 | Experiment H-39 | Experiment H-40 | Experiment H-42 |
| 1 | 1.15 | 0.895 | 0.787 | 0.89 | 0.87 | 1.39 |
| 9 | 1.3 | 1.06 | 0.753 | 0.61 | 1.058 | 1.025 |

Since the micro-organs were transduced ex-vivo and the genetically modified micro-organs undergo several media exchanges during the ex-vivo processing over the course of 9-10 days, the residual viral load to the patient was very low. Testing of the residual vector concentration in the tissue before implantation showed 4 logs reduction below the initial virus load in the transduction fluid (approximately 2.36 E10/BP for transduction. In support, the clinical trial presented in Example 3 demonstrated no patient safety issues were encountered in relationship to the HDAd EPO vector.

Example 7

Phase II Human Clinical Trials

Clinical Study Overview

This is a Phase II, open-label, multi-center, controlled, randomized, tailored and titrated dose study. The trial is enrolling about 100 candidate subjects (randomized into treatment or control groups) at approximately 5-10 medical centers.

Subjects in the 2 arms undergo similar study evaluations. Each patient randomized for treatment with dermal GMMO-hEPO undergoes harvesting of 15 dermal tissue biopsies (micro-organs) from the lower abdomen under local anesthesia.

The required portion of these micro-organs are processed and sent back to the treatment facility within 14 days of harvesting for subcutaneous implantation back to the patient, also in the lower abdomen under local anesthesia. The number of micro-organs processed into dermal GMMO-hEPO is based on the targeted initial dose required by the patient derived from the dosage of previous EPO injections. Unprocessed micro-organs are cryo-preserved for possible later use if additional EPO is required by the patient during the titration period, defined as the first two months after initial administration.

During the titration period, if the hemoglobin consistently declines during the first month after treatment, additional dermal GMMO-hEPO are prepared from cryo-preserved micro-organs in order to perform a second administration during the two-month titration period. The number of dermal GMMO-hEPO to prepare is based on the rate of decline of hemoglobin and clinical judgment.

In the case of excessive response, defined as hemoglobin rise above 12 g/dl for 4 consecutive weeks, dose reduction by excision of one or more dermal GMMO-hEPO is performed. Dermal GMMO-hEPO are removed in order to decrease the total administered dose (in U) to the patient based on the rate of elevation of the hemoglobin and clinical judgment. Further dermal GMMO-hEPO excision can be performed at any period if further excessive response is observed in the patient.

The efficacy assessment period commences either after the dose adjustment (second administration of dermal GMMO-hEPO or resection of dermal GMMO-hEPO), if performed, or from the initial administration. The duration of the efficacy assessment period is 4 months. Following the 4 months of efficacy assessment period, an additional period of 4 months of follow-up commences, during which the patient is further monitored for longer-term safety and duration of hemoglobin maintenance.

The objective of the trial is to maintain the patient's hemoglobin levels in the range of 9-11 g/dl for 4 months or more with significant reduction in the need for erythropoietin-stimulating agent (ESA) injections. Laboratory parameters are used to evaluate the response of the treatment. Measurements blood parameters include complete blood count, EPO levels (by clinical ELISA kit), reticulocytes levels (an initial sign of bone marrow response) and hemoglobin levels.

Patients who are in the control arm continue to receive their regular ESA injections per the standard of care and will be evaluated similarly to the treatment arm.

Clinical Trial

Subjects:

A total of about 100 human subjects are in this study. Two-thirds of the subjects will be in the dermal GMMO-hEPO treatment group, and one-third of the subjects will be in the control arm that is treated by Standard of Care. Subjects may include end stage renal disease patients on dialysis.

Inclusion Criteria include at least: Adult male or female subjects between 18 to 75 years of age at the time of screening visit; Subject diagnosed with anemia due to chronic renal failure CKD stage 5 and being treated with hemodialysis for at least 3 months; Patients treated with recombinant erythropoietin to treat their anemia for at least 3 months; Stable Hb and EPO levels due to ESA injections, e.g., patient receiving ESA injection therapy for at least 3 months, wherein hemoglobin levels have been stable at physiological levels for at least one month; Efficient dialysis defined as: Kt/V>1.2; Subjects who are clinically stable; Serum albumin >3.5 g/dl; 8. Subjects with adequate iron stores (transferrin saturation >20.0% and/or ferritin >200 ng/mL); and Willing to provide written informed consent to participate in the study.

Subjects requiring more than 65 IU/kg/day are excluded from the study.

Harvesting:

Fifteen dermal tissue samples (1.5-2.5 mm in diameter and approximately 30 mm long) are harvested from the lower abdomen under local anesthesia. The harvest procedure utilizes a vacuum positioning device and a symmetrically sharpened coring needle attached to a commercially available medical drill. The tissue samples are primarily dermis (containing approximately 1 million fibroblasts on average) with potentially trace amounts of epidermis and fat. The tissue samples remain intact (are not broken down into individual cells) throughout the entire ex-vivo processing and even after implantation back into the same patient.

The harvest process is performed only once. The initial administration of dermal GMMO-hEPO is based on the previous dosage of EPO that the patient received by injections prior to dermal GMMO-hEPO treatment. Micro-organs that are not processed into dermal GMMO-hEPO are cryo-preserved. If the initial dosage by dermal GMMO-hEPO is found to be insufficient during the titration period (defined as the first two months after administration) further dermal GMMO-hEPO will be processed from the cryo-preserved micro-organs. A second administration will be performed after the processing.

Implantation:

The micro-organ tissue samples (containing approximately 1 million cells on average) remain intact throughout the ex-vivo processing, including the transduction with the HDAd-EPO vector. These same tissue samples are then administered back to the patient.

The implantation procedure utilizes a vacuum positioning device and an implantation needle. Each dermal GMMO-hEPO is loaded into the cannula of the implantation needle, and the needle is inserted subcutaneously, guided by the vacuum device, in the area of the lower abdomen under local anesthesia. A maximum of 15 dermal GMMO-hEPO can be implanted, depending on required dose of the patient being treated, which would be a total of approximately 15 million cells.

A second administration of dermal GMMO-hEPO may be performed during the titration period, defined as the first two months after initial administration, based on the hemoglobin response of the patient to dermal GMMO-hEPO.

Analysis:

Each dermal GMMO-hEPO is characterized for daily secretion rate of EPO, and glucose consumption, ex vivo, which gives an indication of tissue viability. In order to assess the presence and effects of contaminants, during ex vivo maintenance, the spent medium is assayed for sterility, gram stain, mycoplasma and endotoxin. Individual dermal GMMO-hEPO will be rejected if they fail the release criterion.

In addition, EPO concentration in the patient's serum is measured prior to and after implantation in order to determine elevation of serum EPO level above baseline after dermal GMMO-hEPO administration. Follow-up and measurements will be for between seven and thirteen months from the last of implantation date.

Results:

It is expected that patients will show maintenance of hemoglobin within the range of 9-11 g/dl for 4 months or more with a single administration of dermal GMMO-hEPO, adjusted to dose, with significant reduction in the need for ESA injections.

Secondarily, it is expected that implantation will result in the avoidance of supra-physiological elevations of serum EPO levels defined as above 200 mU/ml, and reduction of exogenous EPO administration in comparison to standard of care (SOC).

Measurement of the hemoglobin level is the primary indication of the progression of the anemia. The hemoglobin levels of the patients are monitored on a weekly basis throughout the treatment. In addition, laboratory parameters are used to evaluate the response of the treatment. Measurements are of blood parameters including complete blood count, EPO levels, and reticulocytes levels (an initial sign of bone marrow response).

Patients in the trial will be in the study for about 10 months after initial administration of dermal GMMO-hEPO.

Summary:

The major anticipated clinical benefit of the clinical trial is the maintenance of the hemoglobin within the target therapeutic window of 9-11 g/dl with significantly reduced need for additional injections of ESAs and/or blood transfusions. It is anticipated that a continuous steady delivery of EPO will enable better hemoglobin control in comparison to EPO injections and will result in less hemoglobin cycling which has been linked to increased morbidity and mortality in renal anemia patients.

It will be appreciated by a person skilled in the art that the present invention is not limited by what has been particularly shown and described hereinabove. Rather, the scope of the invention is defined by the claims that follow:

What is claimed is:

1. A method of treating anemia in a human subject in need over a sustained time period comprising the steps of:
   (a) providing at least one autologous erythropoietin secreting genetically modified dermal micro-organ that comprises a helper-dependent adenovirus vector comprising the nucleic acid sequence encoding erythropoietin operably linked to one or more regulatory sequences, wherein said nucleic acid comprises SEQ ID NO: 11,
   (b) determining the erythropoietin secretion levels of the at least one genetically modified dermal micro-organ in step (a) in vitro,
   (c) implanting the autologous genetically modified dermal micro-organ of step (b) in said human subject at an effective dosage at a site selected from the group consisting of subcutaneously, subdermally and intradermally,
   (d) measuring hemoglobin levels in the blood of said human subject from step (c); and
   (e) maintaining hemoglobin levels in said human subject at 9-11 g/dl in at least 50% of the measurements for at least one month, thereby treating anemia in a human subject.

2. The method of claim 1, wherein the autologous genetically modified dermal micro-organ to be implanted provides said an effective dosage of 18-150 U erythropoietin/Kg body weight of said subject/day, as determined by in vitro secretion of erythropoietin from the genetically modified micro-organ.

3. The method of claim 2, wherein the autologous genetically modified dermal micro-organ to be implanted provides said an effective dosage of 18-30 U erythropoietin/Kg body weight of said subject/day, as determined by in vitro secretion of erythropoietin from the genetically modified micro-organ.

4. The method of claim 2, wherein the autologous genetically modified dermal micro-organ to be implanted provides said an effective dosage of 30-50 U erythropoietin/Kg body weight of said subject/day, as determined by in vitro secretion of erythropoietin from the genetically modified micro-organ.

5. The method of claim 2, wherein the autologous genetically modified dermal micro-organ to be implanted provides said an effective dosage of 50-65 U erythropoietin/Kg body weight of said subject/day, as determined by in vitro secretion of erythropoietin from the genetically modified micro-organ.

6. The method of claim 2, wherein said effective dosage is determined based on:
   a. said subject's weight;
   b. said subject's historical hemoglobin levels; and
   c. the average amount of erythropoientin administered to said subject in the one month prior said implanting step.

7. The method of claim 1, wherein said measured hemoglobin levels are 9-11 g/dl in at least 50% of the measurements for at least six months.

8. The method of claim 1, further comprising a step of implanting at a later date to said human subject, at least one additional autologous erythropoietin secreting genetically modified dermal micro-organ that comprises a helper-dependent adenovirus vector comprising the nucleic acid sequence encoding erythropoietin operably linked to one or more regulatory sequences, wherein said nucleic acid comprises SEQ ID NO: 11.

9. The method of claim 1, further comprising a step of maintaining said at least one genetically modified dermal micro-organ in vitro for at least 9 days, prior to said implantation step.

10. The method of claim 1, wherein said subject is selected from a group consisting of:
    a. a subject suffering from: renal failure, chronic renal failure, chemotherapy induced anemia, anemia as a result of HIV treatments, microangiopathic haemolytic anemia, anemia as a result of prematurity, an inflammatory condition including rheumatoid arthritis, an infection, anemia associated with cancers including multiple myeloma and non-Hodgkin lymphoma, hematopoietic stem cell disorders, sickle cell anemia or thalassemia; and
    b. a subject in need of accelerated erythroid repopulation after bone marrow transplantation;
or any combination thereof.

11. The method of claim 10, wherein said subject suffering from chronic renal failure is suffering from chronic kidney disease (CKD) or end stage renal disease (ESRD).

12. A method of increasing or maintaining physiological hemoglobin levels in a human subject in need over a sustained time period comprising the steps of:
    (a) providing at least one autologous erythropoietin secreting genetically modified dermal micro-organ that comprises a helper-dependent adenovirus vector comprising the nucleic acid sequence encoding erythropoietin operably linked to one or more regulatory sequences, wherein said nucleic acid comprises SEQ ID NO: 11,
    (b) determining the erythropoietin secretion levels of the at least one genetically modified dermal micro-organ in step (a) in vitro,
    (c) implanting the autologous genetically modified dermal micro-organ of step (b) in said human subject at an effective dosage at a site selected from the group consisting of subcutaneously, subdermally and intradermally,
    (d) measuring hemoglobin levels in the blood of said human subject from step (c); and
    (e) maintaining hemoglobin levels in said human subject at 9-11 g/dl in at least 50% of the measurements for at least one month, thereby increasing or maintaining physiological hemoglobin levels in a human subject.

13. The method of claim 12, wherein the autologous genetically modified dermal micro-organ to be implanted provides said an effective dosage of 18-150 U erythropoietin/Kg body weight of said subject/day, as determined by in vitro secretion of erythropoietin from the genetically modified micro-organ.

14. The method of claim 13, wherein the autologous genetically modified dermal micro-organ to be implanted provides said an effective dosage of 18-30 U erythropoietin/Kg body weight of said subject/day, as determined by in vitro secretion of erythropoietin from the genetically modified micro-organ.

15. The method of claim 13, wherein the autologous genetically modified dermal micro-organ to be implanted provides said an effective dosage of 30-50 U erythropoietin/

Kg body weight of said subject/day, as determined by in vitro secretion of erythropoietin from the genetically modified micro-organ.

16. The method of claim 13, wherein the autologous genetically modified dermal micro-organ to be implanted provides said an effective dosage of 50-65 U erythropoietin/Kg body weight of said subject/day, as determined by in vitro secretion of erythropoietin from the genetically modified micro-organ.

* * * * *